US009828351B2

(12) United States Patent
Flynn et al.

(10) Patent No.: US 9,828,351 B2
(45) Date of Patent: Nov. 28, 2017

(54) ENZYME INTERACTING AGENTS

(71) Applicants: MONASH UNIVERSITY, Clayton, Victoria (AU); UNIVERSITY OF SOUTH AUSTRALIA, Adelaide, South Australia (AU); CENTRAL ADELAIDE LOCAL HEALTH NETWORK INCORPORATED, Adelaide, South Australia (AU)

(72) Inventors: Bernard Luke Flynn, Donvale (AU); Luigi Aurelio, Eltham (AU); Carmen Vittoria Scullino, Moonee Ponds (AU); Bing Hui Wang, Camberwell (AU); Stuart Maxwell Pitson, Glenside (AU); Melissa Rose Pitman, Blackwood (AU)

(73) Assignees: MONASH UNIVERSITY, Clayton (AU); UNIVERSITY OF SOUTH AUSTRALIA, Adelaide (AU); CENTRAL ADELAIDE LOCAL HEALTH NETWORK INCORPORATED, Adelaide (AU)

( * ) Notice: Subject to any disclaimer, the term of this patent is extended or adjusted under 35 U.S.C. 154(b) by 0 days.

(21) Appl. No.: 15/321,693

(22) PCT Filed: Jun. 26, 2015

(86) PCT No.: PCT/AU2015/050358
§ 371 (c)(1),
(2) Date: Dec. 22, 2016

(87) PCT Pub. No.: WO2015/196258
PCT Pub. Date: Dec. 30, 2015

(65) Prior Publication Data
US 2017/0190698 A1 Jul. 6, 2017

(30) Foreign Application Priority Data

Jun. 26, 2014 (AU) .............................. 2014902459

(51) Int. Cl.
*C07D 271/113* (2006.01)
*C07D 285/08* (2006.01)
*C07D 419/12* (2006.01)
*C07D 285/135* (2006.01)
*C07D 271/07* (2006.01)
*C07D 277/56* (2006.01)
*C07D 271/10* (2006.01)
*C07D 413/12* (2006.01)
*C07D 413/10* (2006.01)
*C07D 271/107* (2006.01)

(52) U.S. Cl.
CPC ......... *C07D 285/08* (2013.01); *C07D 271/07* (2013.01); *C07D 271/10* (2013.01); *C07D 271/107* (2013.01); *C07D 271/113* (2013.01); *C07D 277/56* (2013.01); *C07D 285/135* (2013.01); *C07D 413/10* (2013.01); *C07D 413/12* (2013.01); *C07D 419/12* (2013.01)

(58) Field of Classification Search
CPC .................................................. C07D 271/113
See application file for complete search history.

(56) References Cited

U.S. PATENT DOCUMENTS

| 3,752,819 A | 8/1973 | Philippe |
| 5,998,424 A * | 12/1999 | Galemmo, Jr. ...... C07D 231/14 514/269 |
| 2009/0291967 A1 | 11/2009 | Gupta et al. |
| 2009/0306396 A1 | 12/2009 | Toyoshima et al. |
| 2011/0172186 A1 * | 7/2011 | Behnke ................. A61K 31/69 514/64 |

FOREIGN PATENT DOCUMENTS

| DE | 2065430 A1 | 10/1973 |
| KR | 10-2015-0049698 | 5/2015 |
| KR | 1559883 B1 * | 10/2015 |
| WO | WO-2003028641 A2 | 4/2003 |
| WO | WO-2003105840 A2 | 12/2003 |
| WO | WO-2007043400 A1 | 4/2007 |
| WO | WO-2007149395 A2 | 12/2007 |
| WO | WO-2009011850 A2 | 1/2009 |
| WO | WO-2009126691 A1 | 10/2009 |

OTHER PUBLICATIONS

Xiang et al. Synthetic Metals 2006, 156, 270-275.*
Bhat et al., "Synthesis and Biological Screening of Some 1,3,4-Oxadiazoles," *Indian Journal of Heterocyclic Chemistry*, 21(2):183-184, 2011.
CAS Registry No. 881990-28-9, Entered STN Apr. 26, 2006.
CAS Registry No. 1293122-96-9, Entered STN May 11, 2011.
CAS Registry No. 904282-33-3, Entered STN Aug. 24, 2006.
CAS Registry No. 1223611-41-3, Entered STN May 14, 2010.
CAS Registry No. 799275-69-7, Entered STN Dec. 17, 2004.
CAS Registry No. 1431359-79-3, Entered STN May 15, 2013.
CAS Registry No. 1223377-21-6, Entered STN May 14, 2010.
CAS Registry No. 904307-71-7, Entered STN Aug. 24, 2006.
CAS Registry No. 1328332-74-6, Entered STN Sep. 5, 2011.
CAS Registry No. 1322341-28-5, Entered STN Aug. 24, 2011.
CAS Registry No. 1300284-03-0, Entered STN May 25, 2011.
CAS Registry No. 1298915-60-2, Entered STN May 22, 2011.
CAS Registry No. 1202977-15-8, Entered STN Jan. 24, 2010.
CAS Registry No. 1051308-31-6, Entered STN Sep. 21, 2008.
CAS Registry No. 1042829-58-2, Entered STN Aug. 22, 2008.

(Continued)

*Primary Examiner* — Matthew Coughlin
(74) *Attorney, Agent, or Firm* — Marshall, Gerstein & Borun LLP

(57) ABSTRACT

The present disclosure relates generally, but not exclusively, to compounds and their use as enzyme interacting agents, in particular, agents which interact with one or more enzymes in the sphingolipid biosynthesis pathway. The disclosure further relates to the use of such compounds as research tools, use in therapy, to compositions and agents comprising said compounds, and to methods of treatment using said compounds.

17 Claims, 1 Drawing Sheet

(56) References Cited

OTHER PUBLICATIONS

CAS Registry No. 955737-39-0, Entered STN Nov. 23, 2007.
CAS Registry No. 953861-30-8, Entered STN Nov. 15, 2007.
CAS Registry No. 931613-67-1, Entered STN Apr. 22, 2007.
M. Maceyka et al., "Sphingosine-1-phosphate signaling and its role in disease," *Trends in Cell Biology*, 22:50-60, 2012.
S. Pyne et al., "Sphingosine Kinase Inhibitors and Cancer: Seeking the Golden Sword of Hercules," *Cancer Research*, 71:6576-82, 2011.
D. Salvemini et al., "Therapeutic targeting of the ceramide-to-sphingosine 1-phosphate pathway in pain," *Trends in Pharmacological Sciences*, 34:110-118, 2013.
W-Q. Lai et al., "Sphingosine kinase and sphingosine 1-phosphate in asthma," *Bioscience Reports*, 31:145-50, 2011.
Y. Kong et al., "Structure-Based Discovery of a Boronic Acid Bioisostere of Combretastatin A-4," *Chemistry & Biology*, 12:1007-1014, 2005.
D. Pchejetski et al., "Therapeutic potential of targeting sphingosine kinase 1 in prostate cancer," *Nat. Rev. Urol.*, 8:569-578, 2011.
B. Ogretmen et al., "Biologically Active Sphingolipids in Cancer Pathogenesis and Treatment," *Nature Reviews*, 4:604-616, 2004.
International Search Report for Application No. PCT/AU2015/050358, dated Oct. 1, 2015.

\* cited by examiner

ENZYME INTERACTING AGENTS

FIELD

The present disclosure relates generally, but not exclusively, to compounds and their use as enzyme interacting agents, in particular, agents which interact with one or more enzymes in the sphingolipid biosynthesis pathway. The disclosure further relates to the use of such compounds as research tools, use in therapy and manufacture of medicaments, to compositions and agents comprising said compounds, and to methods of treatment using said compounds.

BACKGROUND

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Sphingolipids, a class of compounds defined by their common 18 carbon amino alcohol backbones, mediate cell-cell and cell-substratum interactions, modulate the behavior of cellular proteins and receptors, and participate in signal transduction. They are therefore important regulators of cell growth, differentiation and survival. The sphingolipids are synthesised de novo from palmitoyl-CoA and serine via a pathway whereby the carbon backbone, alcohol and amino groups are modified to form the various bioactive compounds, such as ceramide, sphingosine and sphingosine-1-phosphate (Scheme 1). Perturbations in the sphingolipid biosynthetic pathway are implicated in many physiological and pathophysiological processes, including cancer, diabetes, inflammation, and Alzheimer's disease.

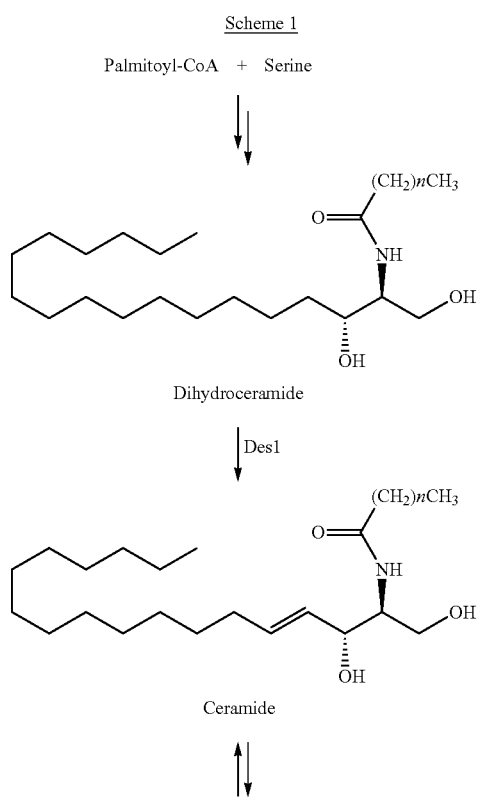

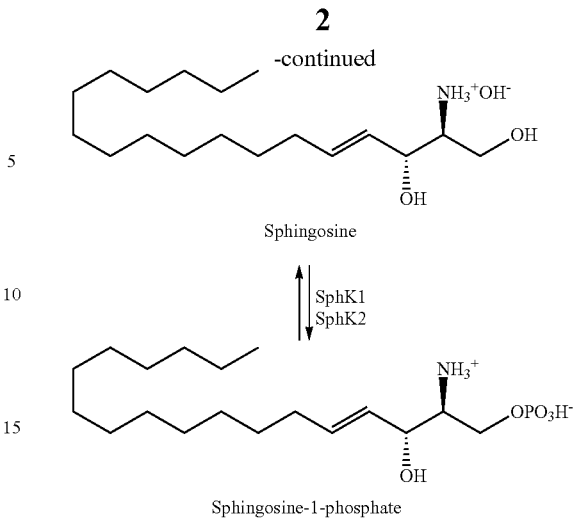

One of the most studied sphingolipids is sphingosine-1-phosphate (S1P) which is formed by the phosphorylation of sphingosine (Sph) by two kinases: sphingosine kinase 1 (SphK1), located mainly in the cytosol, and sphingosine kinase 2 (SphK2), located in several intracellular compartments. S1P levels are controlled by numerous factors, including the SphKs, and by enzymes that degrade S1P (see M Maceyka et al, *Trends in Cell Biology*, 2012, 22, 50-60 and references cited therein).

S1P plays a key role in cancer progression, regulating cell growth, suppression of apoptosis, tumour angiogenesis, metastasis and chemoresistance, and is capable of up-regulating a variety of pro-survival pathways and down-regulating apoptotic pathways. Accordingly, an increase in SphK1 expression and activity leads to a marked shift in the Sph:S1P ratio, in favour of S1P. This in turn triggers a series of pro-survival pathways (glycolysis, angiogenesis, metastasis etc) and cell growth and down regulates apoptotic pathways, promoting the survival and spread of cancer cells. Numerous model studies indicate that over-expression of SphK1 promotes tumour growth whereas inhibition reduces tumour growth, angiogenesis and chemoresistance (resistance is often associated with sustained SphK1 expression). Down regulation of SphK2 has also been shown to inhibit cancer cell growth and enhance chemotherapy induced apoptosis. (M Maceyka et al, supra, and S Pyne et al, *Cancer Res.* 2011, 71, 6576-82, and references cited therein).

S1P also plays important roles in fibrotic disease. Fibrosis is a pathologic condition involving aberrant and uncontrolled extracellular matrix production by the connective tissue as a result of injury or disease, leading to excessive scarring. This leads to increasing tissue dysfunction and, ultimately, organ failure. Fibrosis is a key cause of heart, lung, liver and kidney failure in diseases such as heart attack, diabetic nephropathy, idiopathic pulmonary fibrosis and cirrhosis of the liver. Heightened levels of S1P have been detected in fibrotic tissue and S1P has been shown to be a promoter of a number of the cellular processes that contribute to fibrosis: cell differentiation into fibroblasts and myofibroblasts (scar forming cells), extracellular matrix (ECM) production by myofibroblasts, hypertrophy and mast cell activation (Takuwu N. et al. Sphingosine-1-phosphate in cardiac fibrosis. *Inflammation and Regeneration*, 2013, 33(2), 96-108).

Asthma is a chronic inflammatory disorder leading to wheezing, breathlessness and coughing and its incidence in developed nations is increasing. Studies have demonstrated the key role of the SphK1 and 2/S1P pathway in the development of asthma by regulating pro-inflammatory responses where blockade of SphK1/2 activity has been shown to supress airway inflammation (W-Q. Lai, et al, *Bioscience Reports*, 2011, 31, 145-50, and references cited therein).

Evidence also implicates the role of S1P in both neuropathic and nociceptive pain in diverse etiologies and regulation of the activity of SphK1 and/or SphK2 has been suggested as offering potential for the development of analgesics (D. Salvemini et al, *Trends in Pharmacological Sciences*, 2013, 34, 110-118, and references cited therein).

Small molecules inhibitors of SphK1 and SphK2 can bind to either the substrate (sphingosine) binding domain or the ATP binding domain (C. Loveridge et al. *J. Biol. Chem.* 2010, 285, 38891; K. G. Lim et al. *J. Biol. Chem.* 2011, 286, 18633). A third site on SphK1 has also been identified from competitive binding studies and is termed the allosteric site. In extracellular studies on SphK1 activity, compounds that bind to the allosteric site may either enhance or inhibit enzymatic activity. In cells, however, these compounds may also promote to polyubiquination and proteasomal degradation of the protein (SphK1). It has been proposed that this allosteric site may indeed be an autoregulatory domain where S1P binds to down-regulate SphK1 through both enzymatic inhibition and down-expression (proteasomal degradation). Exogenous ligands that bind to this site may also block the enzyme through both processes (enzymatic inhibition and degradation) or, alternatively, may block S1P binding and fix the enzyme in an active conformation, promoting S1P production. Thus, exogenous allosteric binders may either act as allosteric blockers or enhancers of SphK1 activity.

Another enzyme in the sphingolipid signalling pathway, dihydroceramide desaturase-1 (Des1), has also been implicated in disease. Des1 is active in an earlier stage of the biosynthetic pathway and mediates the conversion of dihydroceramide (dhCer) (e.g. n=16) to ceramide (Cer) (e.g. n=16) by the introduction of the 4,5-double bond into the carbon backbone (see Scheme 1, supra). Since both dhCer and Cer are metabolised into other sphingolipids by the same enzymes, Des1 is responsible for the overall relative levels of all dihydrosphingolipids compared to their Δ4-unsaturated counterparts. The accumulation of dhCer and other dihydrosphingolipids that results from blocking Des1 has been shown to have therapeutic potential in cancer, metabolic disease and viral and bacterial infection (Gagliostro V et al. *Prog. Lipid Res.* 2012, 51. 82-94). The anticancer effects of Des1 inhibition are linked to a combination of apoptotic and autophagic cancer cell death. While the mechanistic details of this remain to be discerned, it is possible that by inhibiting Des1 the downstream S1P is decreased and the upstream dihydrosphingosine-1-phosphate (dhS1P) is increased. Recent studies have shown that dhS1P has opposing effects to S1P in cancer and fibrosis (Bu, S. et al. *J. Biol. Chem.* 2008, 283(28), 19563-19602). DhS1P is able to block the activation of fibroblast that is mediated by S1P and other growth factors such as transforming growth factor-β (TGFβ). Also, in cancer, injections of S1P and dhS1P have opposing effects on tumour growth in xenograft models, S1P promotes growth and dhS1P suppresses it (Barth B. M. et al. *ACS Nano.* 2013, 7, 2132-2144).

Notwithstanding their importance in cellular function and survival, the study of these sphingolipid enzymes has thus far been limited at least in part due to the paucity of suitable exogenous agents which target or interact with them. Therefore, a need exists for the identification of new agents which can interact with SphK1 and/or SphK2 and/or Des1.

SUMMARY

Throughout this specification and the claims which follow, unless the context requires otherwise, the word "comprise" and variations such as "comprises" and "comprising" will be understood to imply the inclusion of a stated integer or step or group of integers but not the exclusion of any other integer or step or group of integers or steps.

Throughout this specification and the claims which follow, unless the context requires otherwise, the phrase "consisting essentially of", and variations such as "consists essentially of" will be understood to indicate that the recited element(s) is/are essential i.e. necessary, elements of the invention. The phrase allows for the presence of other non-recited elements which do not materially affect the characteristics of the invention but excludes additional unspecified elements which would affect the basic and novel characteristics of the method defined.

All aspects, embodiments and examples described herein are encompassed and contemplated by the term "invention".

The singular forms "a", "an" and "the" as used throughout are intended to include plural aspects where appropriate unless the context clearly dictates otherwise.

It has now been discovered that some non-sphingolipid-like heteroaromatic compounds can interact with certain binding sites of one or more enzymes in the sphingolipid biosynthetic pathway. By virtue of their interaction with one or more of the sphingolipid biosynthetic pathway enzymes, such as sphingosine kinase 1 and/or 2 and/or Des1 these compounds may be useful as research tools, for example in the investigation of the role and activity of the sphingolipid enzymes, as comparison or control molecules, or, in some embodiments, in therapeutic applications.

Accordingly, in a first aspect, the disclosure provides a compound of Formula (I);

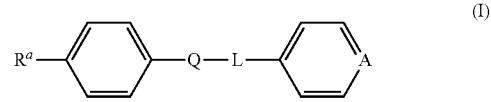

wherein

Q is a 5-membered heteroaromatic ring having 2 or 3 ring heteroatoms, at least one of which must be N and the remaining selected from N, O and S;

L is absent or a bivalent linker group selected from —NH—, —*NH—CH$_2$—, —*CH$_2$—NH—, *NH—NH—, and —*C(=O)—NH—, wherein the linker atom labelled * is bonded to Q;

$R^a$ is selected from hydrogen, halo, haloalkyl, haloalkoxy, alkyl, alkoxy, alkoxyalkyl, alkoxyalkoxy, carbocyclyl, carbocyclylalkyl, carbocyclyloxy, heterocyclyl, heterocyclylalkyl, heterocyclyloxy, aryl, arylalkyl, heteroaryl, heteroarylalkyl, aryloxy or heteroaryloxy, and wherein each of carbocyclyl, carbocyclylalkyl, carbocyclyloxy, heterocyclyl, heterocyclylalkyl, heterocyclyloxy, aryl, arylalkyl, heteroaryl, heteroarylalkyl, aryloxy or heteroaryloxy may be optionally substituted;

A is N or C—$R^b$, wherein $R^b$ is selected from OH, B(OH)$_2$, BF$_3$.M (M=Na, K, Ca, or Mg), C(=NR$^c$)NHR$^d$, and, —C(=O)NHR$^d$;

wherein $R^c$ and $R^d$ are independently selected from hydrogen, hydroxy, alkyl, aryl, heteroaryl, carbocyclyl, heterocyclyl or acyl, each of which may be optionally substituted; or $R^b$ is a cyclic group selected from formulae (i)-(iii):

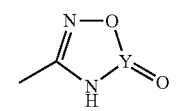
(i)

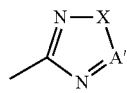
(ii)

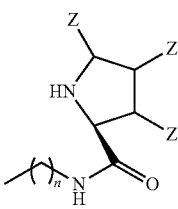
(iii)

wherein
Y is C or S,
X is O, S or NH;
A' is C—R' or N;
R' is hydrogen or alkyl, such as $C_1$-$C_6$ alkyl
each Z is independently H or OH; and
n is an integer from 0-6
or a pharmaceutically acceptable salt or solvate thereof;
provided that:
(i) when L is absent, then $R^b$ is not OH or C(=O)NHR$^d$;
(ii) when L is absent, and $R^b$ is C(=NR$^c$)NH$^d$, then $R^a$ must be a heteroatom or attached to the phenyl ring via a heteroatom, and Q is not

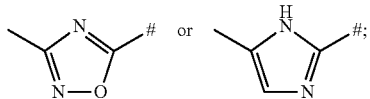

(iii) when L is absent and $R^b$ is a cyclic group of formula (iii) then Q is not

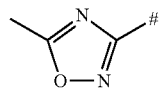

(iv) when L is NH, and A is N, then Q is not

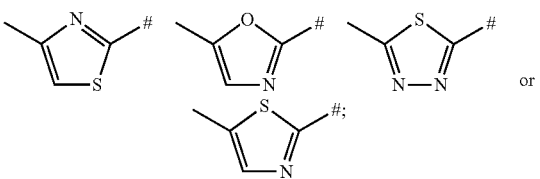

(v) when L is NH and $R^b$ is OH, then Q is not

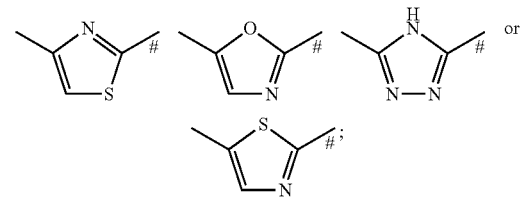

(vi) when L is NH and $R^b$ is C(=O)NHR$^d$, then Q is not

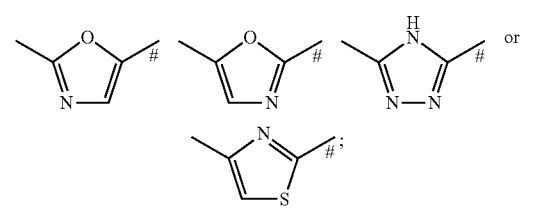

(vii) when L is *C(=O)—NH and A is N, then Q is not

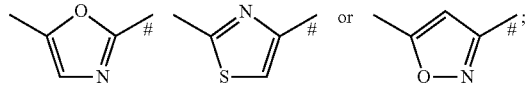

(viii) when L is *C(=O)—NH, then $R^b$ is not a cyclic group of formula (ii);

(ix) when L is *C(=O)—NH and $R^b$ is OH, then Q is not

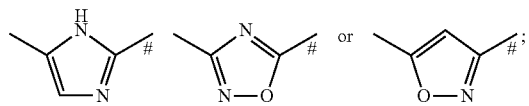

(x) when L is *C(=O)—NH and $R^b$ is C(=O)NHR$^d$, then Q is not

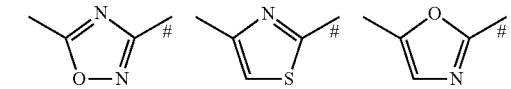

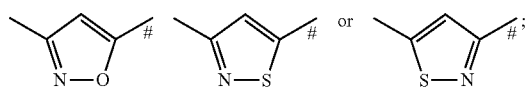

(xi) when L is *CH$_2$—NH and $R^b$ is OH, then Q is not

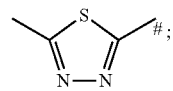

(xii) when L is *CH₂—NH, then $R^b$ is not C(=O)NHR$^d$;
(xiii) when L is *NH—CH₂ and A is N, then Q is not

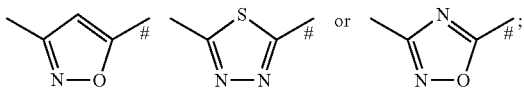

(xiv) when L is *NH—CH₂ and $R^b$ is OH, then Q is not

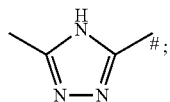

and
(xv) when L is *NH—CH₂ and $R^b$ is C(=O)NHR$^d$, then Q is not

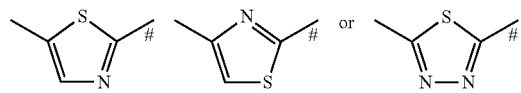

wherein in the Q groups depicted in (i)-(xv) the bond labelled # is attached to L.

In another aspect, the disclosure provides a composition comprising a compound of Formula (I), or a pharmaceutically acceptable salt or solvate thereof, and a pharmaceutically acceptable additive.

The disclosure also provides a compound of Formula (I), or a pharmaceutically acceptable salt or solvate thereof, or a composition comprising said compound or a pharmaceutically acceptable salt or solvate thereof, for use as an agent for interacting with an enzyme in the sphingolipid pathway. In some embodiments, the enzyme may be sphingosine kinase SphK1 and/or SphK2 and/or Des1.

The disclosure also provides a compound of Formula (I), or a pharmaceutically acceptable salt or solvate thereof, or a composition comprising said compound or a pharmaceutically acceptable salt or solvate thereof, for use in therapy, such as for inhibiting undesirable cell proliferation, or treating a fibrotic disease, or treating a disease or condition in which excessive or undesirable sphingolipid enzyme activity is implicated.

A further aspect disclosed herein provides a method of inhibiting undesirable cell proliferation in a subject in need thereof comprising administering to said subject, a compound of Formula (I), or a pharmaceutically acceptable salt or solvate thereof.

A further aspect disclosed herein provides a method of treating a fibrotic disease in a subject in need thereof comprising administering to said subject, a compound of Formula (I), or a pharmaceutically acceptable salt or solvate thereof.

Also disclosed herein is a method of treating a disease or condition in which excessive or undesirable sphingolipid enzyme activity is implicated in a subject in need thereof comprising administering to said subject, a compound of Formula (I), or a pharmaceutically acceptable salt or solvate thereof.

Yet another aspect disclosed herein provides use of a compound of Formula (I), or a pharmaceutically acceptable salt or solvate thereof, in the manufacture of a medicament.

Yet another aspect disclosed herein provides use of a compound of Formula (I), or a pharmaceutically acceptable salt or solvate thereof, in the manufacture of a medicament for inhibiting undesirable cell proliferation.

Yet another aspect disclosed herein provides use of a compound of Formula (I), or a pharmaceutically acceptable salt or solvate thereof, in the manufacture of a medicament for treating a fibrotic disease.

Yet another aspect disclosed herein provides use of a compound of Formula (I), or a pharmaceutically acceptable salt or solvate thereof, in the manufacture of a medicament for treating a disease or condition in which excessive or undesirable sphingolipid enzyme activity is implicated.

Diseases or conditions in which excessive or undesirable sphingolipid enzyme activity is implicated may include cancer, asthma, fibrotic diseases, inflammation, pain and metabolic disorders.

DESCRIPTION

Figure 1:
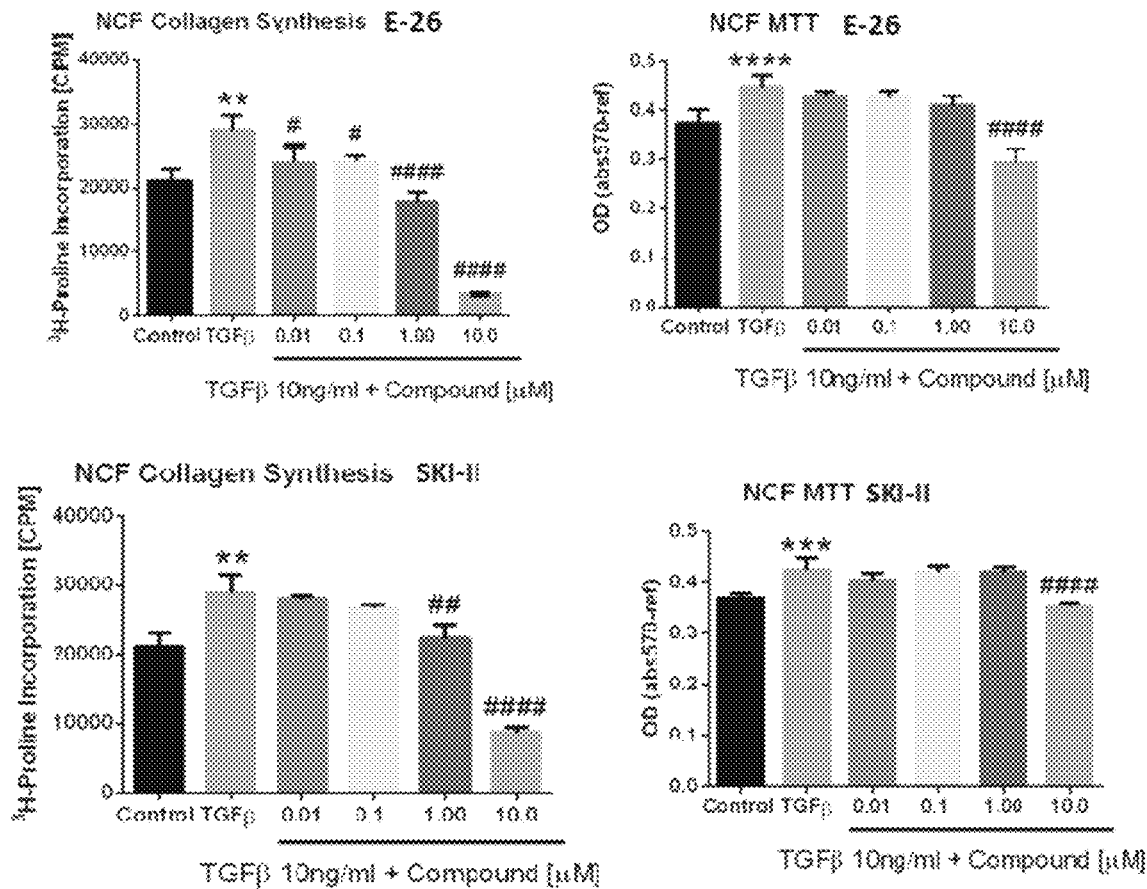
FIG. 1 graphically depicts inhibition of collagen synthesis and cell viability in NCF cells by Compound E-26 and reference compound SK-II.

The term "halogen" ("halo") denotes fluorine, chlorine, bromine or iodine (fluoro, chloro, bromo or iodo).

As used herein, the term "alkyl" or "alk", used either alone or in compound words denotes straight chain, or branched alkyl, including $C_{1-20}$, such as $C_{1-10}$ or $C_{1-6}$ alkyl. Examples of straight chain and branched alkyl include methyl, ethyl, n-propyl, isopropyl, n-butyl, sec-butyl, t-butyl, n-pentyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2,-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyl-octyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propylocytl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. Where an alkyl group is referred to generally as "propyl", butyl" etc, it will be understood that this can refer to any of straight or branched isomers where appropriate. An alkyl group may be optionally substituted by one or more optional substituents as herein defined.

Terms written as "groupAgroupB" are intended to refer to a groupA when linked by a divalent form of groupB. For example, "hydroxyalkyl" is a hydroxy group when linked by an alkylene group, "haloalkyl" is a halo group when linked by an alkylene group, "alkoxyalkyl" is an alkoxy group when linked by an alkylene group, etc. Similarly, "alkoxy" denotes alkyl, as herein defined, when linked by an oxygen atom, "aryloxy" denotes aryl, as herein defined, when linked by an oxygen atom, etc.

The term "aryl" denotes any of mono-, bi- or polcyclic, (including conjugated and fused) hydrocarbon ring systems containing an aromatic residue. Examples of aryl include phenyl, biphenyl, terphenyl, quaterphenyl, naphthyl, tetrahydronaphthyl (tetralinyl), anthracenyl, dihydroanthracenyl, benzanthracenyl, dibenzanthracenyl, phenanthrenyl, fluorenyl, pyrenyl, idenyl, isoindenyl, indanyl, azulenyl and chrysenyl. Particular examples of aryl include phenyl and naphthyl. An aryl group may be optionally substituted by one or more optional substituents as herein defined.

The term "carbocyclyl" includes any of non-aromatic monocyclic, bicyclic and polycyclic, (including fused, bridged or conjugated) hydrocarbon residues, e.g. $C_{3-20}$ (such as $C_{3-10}$ or $C_{3-8}$). The rings may be saturated, for example cycloalkyl, or may possess one or more double bonds (cycloalkenyl) and/or one or more triple bonds (cycloalkynyl). Examples of carbocyclyl are monocyclic 5-6-membered or bicyclic 9-10 membered ring systems. Suitable examples include cyclopropyl, cyclobutyl, cyclopentyl, cyclohexyl, cycloheptyl, cyclooctyl, cyclononyl, cyclodecyl, cyclopentenyl, cyclohexenyl, cyclooctenyl, cyclopentadienyl, cyclohexadienyl, cyclooctatetraenyl and decalinyl. A carbocyclyl group may be optionally substituted by one or more optional substituents as herein defined. A monocarbocyclyl group may be substituted by a bridging group to form a bicyclic bridged group.

The term "heterocyclyl" when used alone or in compound words includes any of monocyclic, bicyclic or polycyclic, (including fuse, bridged or conjugated) hydrocarbon residues, such as $C_{3-20}$ (e.g. $C_{3-10}$ or $C_{3-8}$) wherein one or more carbon atoms are independently replaced by a heteroatom so as to provide a group containing a non-aromatic heteroatom containing ring. Suitable heteroatoms include, O, N, S, P and Se, particularly O, N and S. Where two or more carbon atoms are replaced, this may be by two or more of the same heteroatom or by different heteroatoms. The heterocyclyl group may be saturated or partially unsaturated, e.g. possess one or more double bonds. Particularly preferred heterocyclyl are monocyclic 5-6- and bicyclic 9-10-membered heterocyclyl. Suitable examples of heterocyclyl groups may include azridinyl, oxiranyl, thiiranyl, azetidinyl, oxetanyl, thietanyl, 2H-pyrrolyl, pyrrolidinyl, 1-, 2- and 3-pyrrolinyl, piperidyl, piperazinyl, morpholinyl, indolinyl, imidazolidinyl, imidazolinyl, pyrazolidinyl, thiomorpholinyl, dioxanyl, tetrahydrofuranyl, tetrahydropyranyl, tetrahydropyrrolyl, tetrahydrothiophenyl (tetramethylene sulfide), pyrazolinyl, dioxalanyl, thiazolidinyl, isoxazolidinyl, dihydropyranyl, oxazinyl, thiazinyl, thiomorpholinyl, oxathianyl, dithianyl, trioxanyl, thiadiazinyl, dithiazinyl, trithianyl, thiadiazolinyl, azepinyl, oxepinyl, thiepinyl, indenyl, indanyl, 3H-indolyl, isoindolinyl, 4H-quinolazinyl, chromenyl, chromanyl, isochromanyl, benzoxazinyl (2H-1,3, 2H-1,4-, 1H-2,3-, 4H-3, 1-4H-1,4) pyranyl and dihydropyranyl. A heterocyclyl group may be optionally substituted by one or more optional substituents as defined herein.

The term "heteroaryl" includes any of monocyclic, bicyclic, polycyclic, (fused or conjugated) hydrocarbon residues, wherein one or more carbon atoms are replaced by a heteroatom so as to provide a residue having at least one aromatic heteroatom-containing ring. Some exemplary heteroaryl have 3-20 ring atoms, e.g. 3-10. Further examples of heteroaryl are 5-6 monocyclic and 9-10 membered bicyclic ring systems. Suitable heteroatoms include, O, N, S, P and Se, particularly O, N and S. Where two or more carbon atoms are replaced, this may be by two or more of the same heteroatom or by different heteroatoms. Suitable examples of heteroaryl groups may include pyridyl, pyrrolyl, thienyl, imidazolyl, furanyl, benzothienyl, isobenzothienyl, benzofuranyl, isobenzofuranyl, indolyl, isoindolyl, pyrazolyl, pyrazinyl, pyrimidinyl, pyridazinyl, indolizinyl, quinolyl, isoquinolyl, phthalazinyl, 1,5-naphthyridinyl, quinozalinyl, quinazolinyl, quinolinyl, oxazolyl, thiazolyl, isothiazolyl, isoxazolyl, triazolyl, oxadialzolyl, oxatriazolyl, triazinyl, tetrazolyl and furazanyl. A heteroaryl group may be optionally substituted by one or more optional substituents as defined herein.

The term "acyl" either alone or in compound words denotes a group containing the moiety C=O (in some examples, not being a carboxylic acid, ester or amide) Preferred acyl includes C(O)—R, wherein R is hydrogen or an alkyl, alkenyl, alkynyl, aryl, heteroaryl, carbocyclyl, or heterocyclyl residue. Examples of acyl include formyl, straight chain or branched alkanoyl (e.g. $C_{1-20}$) such as, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; cycloalkylcarbonyl such as cyclopropylcarbonyl cyclobutylcarbonyl, cyclopentylcarbonyl and cyclohexylcarbonyl; aroyl such as benzoyl, toluoyl and naphthoyl; aralkanoyl such as phenylalkanoyl (e.g. phenylacetyl, phenylpropanoyl, phenylbutanoyl, phenylisobutylyl, phenylpentanoyl and phenylhexanoyl) and naphthylalkanoyl (e.g. naphthylacetyl, naphthylpropanoyl and naphthylbutanoyl]; aralkenoyl such as phenylalkenoyl (e.g. phenylpropenoyl, phenylbutenoyl, phenylmethacryloyl, phenylpentenoyl and phenylhexenoyl and naphthylalkenoyl (e.g. naphthylpropenoyl, naphthylbutenoyl and naphthylpentenoyl); aryloxyalkanoyl such as phenoxyacetyl and phenoxypropionyl; arylthiocarbamoyl such as phenylthiocarbamoyl; arylglyoxyloyl such as phenylglyoxyloyl and naphthylglyoxyloyl; arylsulfonyl such as phenylsulfonyl and napthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolyglyoxyloyl and thienylglyoxyloyl. The R residue may be optionally substituted as described herein.

The term "alkenyl" as used herein denotes groups formed from straight chain or branched hydrocarbon residues containing at least one carbon to carbon double bond including ethylenically mono-, di- or poly-unsaturated alkyl groups as previously defined, preferably $C_{2-20}$ alkenyl (e.g. $C_{2-10}$ or $C_{2-6}$). Examples of alkenyl include vinyl, allyl, 1-methylvinyl, butenyl, iso-butenyl, 3-methyl-2-butenyl, 1-pentenyl, 1-hexenyl, 3-hexenyl, 1-heptenyl, 3-heptenyl, 1-octenyl, 1-nonenyl, 2-nonenyl, 3-nonenyl, 1-decenyl, 3-decenyl, 1,3-butadienyl, 1-4,pentadienyl, 1,3-hexadienyl and 1,4-hexadienyl. An alkenyl group may be optionally substituted by one or more optional substituents as herein defined.

As used herein the term "alkynyl" denotes groups formed from straight chain or branched hydrocarbon residues containing at least one carbon-carbon triple bond including ethynically mono-, di- or poly-unsaturated alkyl groups as previously defined. Unless the number of carbon atoms is specified the term preferably refers to $C_{2-20}$ alkynyl (e.g. $C_{2-10}$ or $C_{2-6}$). Examples include ethynyl, 1-propynyl, 2-propynyl, and butynyl isomers, and pentynyl isomers. An alkynyl group may be optionally substituted by one or more optional substituents as herein defined.

"Optionally substituted" is taken to mean that a group may or may not be further substituted with one or more (e.g. 2, 3, 4 or 5 as permitted), same or different, optional substituents including those selected from:

alkyl, (e.g. $C_{1-6}$alkyl such as methyl, ethyl, propyl, butyl), cycloalkyl (e.g. $C_{3-6}$cycloalkyl, such as cyclopropyl, cyclobutyl, cyclopentyl or cyclohexyl), hydroxyalkyl (e.g. hydroxy$C_{1-6}$alkyl, such as hydroxymethyl, hydroxyethyl, hydroxypropyl), alkoxyalkyl (e.g. $C_{1-6}$alkoxy$C_{1-6}$alkyl, such as methoxymethyl, methoxyethyl, methoxypropyl, ethoxymethyl, ethoxyethyl, ethoxypropyl), alkoxy (e.g. $C_{1-6}$alkoxy, such as methoxy, ethoxy, propoxy, butoxy), alkoxyalkoxy (e.g. $C_{1-6}$alkoxy$C_{1-6}$alkoxy, such as methoxymethoxy, methoxyethoxy, methoxypropoxy, ethoxymethoxy, ethoxyethoxy, ethoxypropoxy, propoxymethoxy, propoxyethoxy, propoxypropoxy), cycloalkoxy (e.g. cyclopropoxy, cyclobutoxy, cyclopentoxyl, cyclohexyloxy), halo, haloalkyl (which includes, mono-, di-, and trihalo, e.g. halo$C_{1-6}$alkyl, such as trifluoromethyl, trichloromethyl, tribromomethyl), haloalkoxy (which includes, mono-, di-, and trihalo, e.g. halo$C_{1-6}$alkoxy, such as trifluoromethoxy, trichloromethoxy, tribromomethoxy), hydroxy, thiol (—SH), alkylthio (e.g. —S$C_{1-6}$alkyl), phenyl (which itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, —OC(O)$C_{1-6}$alkyl, —NH$_2$, —NH$C_{1-6}$alkyl, —NHC(O)$C_{1-6}$alkyl and —N($C_{1-6}$alkyl)($C_{1-6}$alkyl)), benzyl (wherein benzyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, —OC(O)$C_{1-6}$alkyl, —NH$_2$, —NH$C_{1-6}$alkyl, —NHC(O)$C_{1-6}$alkyl and —N($C_{1-6}$alkyl)($C_{1-6}$alkyl)), phenoxy (wherein phenyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, —OC(O)$C_{1-6}$alkyl, —NH$_2$, —NH$C_{1-6}$alkyl, —NHC(O)$C_{1-6}$alkyl and —N($C_{1-6}$alkyl)($C_{1-6}$alkyl)), benzyloxy (wherein benzyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, —OC(O)$C_{1-6}$alkyl, —NH$_2$, —NH$C_{1-6}$alkyl, —NHC(O)$C_{1-6}$alkyl and —N($C_{1-6}$alkyl)($C_{1-6}$alkyl)),

NH$_2$, alkylamino (e.g. —NH$C_{1-6}$alkyl, such as methylamino, ethylamino, propylamino etc), dialkylamino (e.g. —NH($C_{1-6}$alkyl)$_2$, such as dimethylamino, diethylamino, dipropylamino), acylamino (e.g. —NHC(O)$C_{1-6}$alkyl, such as —NHC(O)CH$_3$), phenylamino (i.e. —NHphenyl, wherein phenyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, —OC(O)$C_{1-6}$alkyl, —NH$_2$, —NH$C_{1-6}$alkyl, —NHC(O)$C_{1-6}$alkyl and —N($C_{1-6}$alkyl)$C_{1-6}$alkyl), nitro, cyano, formyl, acyl, including —C(O)-alkyl (e.g. —C(O)$C_{1-6}$alkyl, such as acetyl), —O—C(O)-alkyl (e.g. —OC(O)$C_{1-6}$alkyl, such as acetyloxy), benzoyl (wherein benzyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, —OC(O)$C_{1-6}$alkyl, —NH$_2$, —NH$C_{1-6}$alkyl, —NHC(O)$C_{1-6}$alkyl and —N($C_{1-6}$alkyl)($C_{1-6}$alkyl)), benzoyloxy (wherein benzyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, —OC(O)$C_{1-6}$alkyl, —NH$_2$, —NH$C_{1-6}$alkyl, —NHC(O)$C_{1-6}$alkyl and —N($C_{1-6}$alkyl)($C_{1-6}$alkyl)),

CO$_2$H,

CO$_2$alkyl (e.g. CO$_2C_{1-6}$alkyl such as methyl ester, ethyl ester, propyl ester, butyl ester), CO$_2$phenyl (wherein phenyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, —OC(O)$C_{1-6}$alkyl, —NH$_2$, —NH$C_{1-6}$alkyl, —NHC(O)$C_{1-6}$alkyl and —N($C_{1-6}$alkyl)($C_{1-6}$alkyl)), CO$_2$benzyl (wherein benzyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, —OC(O)$C_{1-6}$alkyl, —NH$_2$, —NH$C_{1-6}$alkyl, —NHC(O)$C_{1-6}$alkyl and —N($C_{1-6}$alkyl)($C_{1-6}$alkyl)),

—CONH$_2$,

—C(O)NHphenyl (wherein phenyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, —OC(O)$C_{1-6}$alkyl, —NH$_2$, —NH$C_{1-6}$alkyl, —NHC(O)$C_{1-6}$alkyl and —N($C_{1-6}$alkyl)($C_{1-6}$alkyl)), —C(O)NHbenzyl (wherein benzyl itself may be further substituted e.g., by one or more of $C_{1-6}$alkyl, halo, hydroxy, hydroxy$C_{1-6}$alkyl, $C_{1-6}$alkoxy, $C_{1-6}$alkoxy$C_{1-6}$alkyl, $C_{1-6}$alkoxy$C_{1-6}$alkoxy, halo$C_{1-6}$alkyl, halo$C_{1-6}$alkoxy, cyano, nitro, —OC(O)$C_{1-6}$alkyl, —NH$_2$, —NH$C_{1-6}$alkyl, —NHC(O)$C_{1-6}$alkyl and —N($C_{1-6}$alkyl)($C_{1-6}$alkyl)), —C(O)NHalkyl (e.g. C(O)NH$C_{1-6}$ alkyl such as methyl ester, ethyl ester, propyl ester, butyl amide), —C(O)NHdialkyl (e.g. C(O)NH($C_{1-6}$alkyl)$_2$), aminoalkyl (e.g., HN$C_{1-6}$alkyl-, $C_{1-6}$alkylHN-$C_{1-6}$alkyl- and ($C_{1-6}$alkyl)$_2$N—$C_{1-6}$alkyl-), thioalkyl (e.g., HS$C_{1-6}$alkyl-), carboxyalkyl (e.g., HO$_2$C$C_{1-6}$alkyl-), carboxyesteralkyl (e.g., $C_{1-6}$alkylO$_2$C$C_{1-6}$alkyl-), amidoalkyl (e.g., H$_2$N(O)C$C_{1-6}$alkyl-, H($C_{1-6}$alkyl)N(O)C$C_{1-6}$alkyl-), formylalkyl (e.g., H(O)C$C_{1-6}$alkyl-), acylalkyl (e.g., $C_{1-6}$alkyl(O)C$C_{1-6}$alkyl-), nitroalkyl (e.g., O$_2$N$C_{1-6}$alkyl-), replacement of CH$_2$ with C═O, and where 2 carbon atoms (1,2 or 1,3) are substituted by one end each of a —O—(CH$_2$)$_n$—O— or —NH—(CH$_2$)$_n$—NH— group, wherein n is 1 or 2.

In further embodiments, optional substitutents are selected from $C_{1-6}$alkyl, $C_{3-6}$cycloalkyl, hydroxy, chloro, bromo, fluoro, iodo, hydroxyC$_{1-6}$alkyl, C$_{1-6}$alkoxy, C$_{1-6}$alkoxyC$_{1-6}$alkyl, haloC$_{1-6}$alkyl, amino, C$_{1-6}$alkylamino, di, cyano, C$_{1-6}$alkylamino, C(=O)C$_{1-6}$alkyl, OC(=O)C$_{1-6}$alkyl, thiol, SC$_{1-6}$alkyl, benzyl (optionally substituted by one or more of C$_{1-6}$alkyl, halo, hydroxy, hydroxyC$_{1-6}$alkyl, C$_{1-6}$alkoxy, C$_{1-6}$alkoxyC$_{1-6}$alkyl, C$_{1-6}$alkoxyC$_{1-6}$alkoxy, haloC$_{1-6}$alkyl, haloC$_{1-6}$alkoxy, cyano, nitro, —OC(O)C$_{1-6}$alkyl, —NH$_2$, —NHC$_{1-6}$alkyl, —NHC(O)-C$_{1-6}$alkyl and —N(C$_{1-6}$alkyl)(C$_{1-6}$alkyl), phenyl, (optionally substituted by one or more of C$_{1-6}$alkyl, halo, hydroxy, hydroxyC$_{1-6}$alkyl, C$_{1-6}$alkoxy, C$_{1-6}$alkoxyC$_{1-6}$alkyl, C$_{1-6}$alkoxyC$_{1-6}$alkoxy, haloC$_{1-6}$alkyl, haloC$_{1-6}$alkoxy, cyano, nitro, —OC(O)C$_{1-6}$alkyl, —NH$_2$, —NHC$_{1-6}$alkyl, —NHC(O)C$_{1-6}$alkyl and —N(C$_{1-6}$alkyl)(C$_{1-6}$alkyl), benzyloxy (optionally substituted by one or more of C$_{1-6}$alkyl, halo, hydroxy, hydroxyC$_{1-6}$alkyl, C$_{1-6}$alkoxy, C$_{1-6}$alkoxyC$_{1-6}$alkyl, C$_{1-6}$alkoxyC$_{1-6}$alkoxy, haloC$_{1-6}$alkyl, haloC$_{1-6}$alkoxy, cyano, nitro, —OC(O)C$_{1-6}$alkyl, —NH$_2$, —NHC$_{1-6}$alkyl, —NHC(O)C$_{1-6}$alkyl and —N(C$_{1-6}$alkyl)(C$_{1-6}$alkyl), phenyloxy, (optionally substituted by one or more of C$_{1-6}$alkyl, halo, hydroxy, hydroxyC$_{1-6}$alkyl, C$_{1-6}$alkoxy, C$_{1-6}$alkoxyC$_{1-6}$alkyl, C$_{1-6}$alkoxyC$_{1-6}$alkoxy, haloC$_{1-6}$alkyl, haloC$_{1-6}$alkoxy, cyano, nitro, —OC(O)C$_{1-6}$alkyl, —NH$_2$, —NHC$_{1-6}$alkyl, —NHC(O)C$_{1-6}$alkyl and —N(C$_{1-6}$alkyl)(C$_{1-6}$alkyl).

The 5-membered heteroaromatic ring having 2 or 3 ring heteroatoms, at least one of which must be N and the remaining selected from N, O and S are selected from heterocyclic rings (a)-(u) (where the bonds labelled # are attached to L):

In some embodiments, Q is selected from Q$_1$, Q$_2$ and Q$_3$:

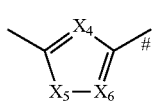

Q2

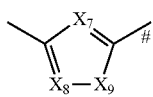

Q3 wherein $X_1$ is O, S or NH and $X_2$ and $X_3$ are independently CH or N, provided both are not CH (formulae (a), (b), (e), (f), (k), (p), (s), (t) and (u));

$X_5$ is O, S or NH and $X_4$ and $X_6$ are independently CH or N, provided both are not CH (formulae (c), (g), (j), (f), (m), (o) and (r)); and $X_9$ is O, S or NH and $X_7$ and $X_8$ are independently CH or N, provided both are not CH (formulae (d), (h), (i), (l), (n) and (q)).

In some embodiments, Q has 3 ring heteroatoms (formulae (c), (d), (g), (h), (k) (p) and (s)). In some examples thereof, Q has two ring nitrogen atoms and one ring oxygen atom. In other examples thereof, Q has two ring nitrogen atoms and one ring sulfur atom.

In other embodiments Q has 2 ring heteroatoms (formulae (a), (b), (e), (f), (i) (j) (l), (m), (n), (o), (q), (r), (t) and (u)). In some examples thereof, Q has one ring nitrogen atom and one ring oxygen atom. In other examples thereof, Q has one ring nitrogen atom and one ring sulfur atom.

In other embodiments, Q has one or two ring nitrogen atoms and one ring oxygen atom (formulae (c), (d), (e), (f), (k) (l) (m), (n) and (o)).

In other embodiments, Q has one or two ring nitrogen atoms and one ring sulfur atom (formulae (a), (b), (g), (h), (i) (j) (p), (q) and (r)).

In other embodiments, Q has two or three ring nitrogen atoms and no O or S ring atoms (formulae (s), (t), and (u)).

In some embodiments, Q is selected from (c), (d),(f), (g), (h), (i), (j), (k) and (p).

In some embodiments, Q is selected from (c), (d),(f), (h), (i), (j), (k) and (p).

In some embodiments, Q is selected from (c), (d),(f), (i), (j), (k) and (p).

In some embodiments, Q is an oxadiazolyl group (formulae (c), (d) and (k)).

It will be understood that where not specified, valencies will be completed by a hydrogen atom.

In some embodiments, L is —NH— or —*C(=O)—NH—, or is absent.

In some embodiments, including any one or more of the embodiments for Q as described above, L is absent. In further embodiments, Q is not (c). In still further embodiments, Q is oxadiazolyl (formula (c), (d) or (k)).

In some embodiments, including any one or more of the embodiments for Q as described above, L is —NH—. In further embodiments thereof, Q is not (b), (e), (f), (i), (p) or (s).

In some embodiments, including any one or more of the embodiments for Q as described in paragraphs above, L is —*C(=O)—NH—. In further embodiments thereof, Q is not (c), (d), (f), (i), (j), (l), (m), (q), (r), or (t).

In some embodiments, including any one or more of the embodiments for Q as described above, L is —*CH$_2$—NH—. In further embodiments thereof, Q is not (p)

In some embodiments, including any one or more of the embodiments for Q as described in paragraphs above, L is —*NH—NH—.

In some embodiments, including any one or more of the embodiments for Q as described in paragraphs above, L is —*NH—CH$_2$—. In further embodiments thereof, Q is not (b), (d), (i), (l), (p) or (s).

Some exemplary embodiments, subject to the provisos of formula (I), are set out below:

Q is (a) and L is NH.
Q is (b) and L is NH.
Q is (c) and L is NH.
Q is (d) and L is NH.
Q is (e) and L is NH.
Q is (f) and L is NH.
Q is (g) and L is NH.
Q is (h) and L is NH.
Q is (i) and L is NH,
Q is (j) and L is NH.
Q is (k) and L is NH.
Q is (l) and L is NH.
Q is (m) and L is NH.
Q is (n) and L is NH.
Q is (o) and L is NH.
Q is (p) and L is NH.
Q is (q) and L is NH.
Q is (r) and L is NH.
Q is (s) and L is NH.
Q is (t) and L is NH.
Q is (u) and L is NH.
Q is (a) and L is *C(=O)—NH.
Q is (b) and L is *C(=O)—NH.
Q is (c) and L is *C(=O)—NH.
Q is (d) and L is *C(=O)—NH.
Q is (e) and L is *C(=O)—NH.
Q is (f) and L is *C(=O)—NH.
Q is (g) and L is *C(=O)—NH.
Q is (h) and L is *C(=O)—NH.
Q is (i) and L is *C(=O)—NH.
Q is (j) and L is *C(=O)—NH.
Q is (k) and L is *C(=O)—NH.
Q is (l) and L is *C(=O)—NH.
Q is (m) and L is *C(=O)—NH.
Q is (n) and L is *C(=O)—NH.
Q is (o) and L is *C(=O)—NH.
Q is (p) and L is *C(=O)—NH.
Q is (q) and L is *C(=O)—NH.
Q is (r) and L is *C(=O)—NH.
Q is (s) and L is *C(=O)—NH.
Q is (t) and L is *C(=O)—NH.
Q is (u) and L is *C(=O)—NH.
Q is (a) and L is *NH—CH$_2$—.
Q is (b) and L is *NH—CH$_2$—.
Q is (c) and L is *NH—CH$_2$—.
Q is (d) and L is *NH—CH$_2$—.
Q is (e) and L is *NH—CH$_2$—.
Q is (f) and L is *NH—CH$_2$—.
Q is (g) and L is *NH—CH$_2$—.
Q is (h) and L is *NH—CH$_2$—.
Q is (i) and L is *NH—CH$_2$—.
Q is (j) and L is *NH—CH$_2$—.
Q is (k) and L is *NH—CH$_2$—.
Q is (l) and L is *NH—CH$_2$—.
Q is (m) and L is *NH—CH$_2$—.
Q is (n) and L is *NH—CH$_2$—.
Q is (o) and L is *NH—CH$_2$—.
Q is (p) and L is *NH—CH$_2$—.

Q is (q) and L is *NH—CH$_2$—.
Q is (r) and L is *NH—CH$_2$—.
Q is (s) and L is *NH—CH$_2$—.
Q is (t) and L is *NH—CH$_2$—.
Q is (u) and L is *NH—CH$_2$—.
Q is (a) and L is *CH$_2$—NH—.
Q is (b) and L is *CH$_2$—NH—.
Q is (c) and L is *CH$_2$—NH—.
Q is (d) and L is *CH$_2$—NH—.
Q is (e) and L is *CH$_2$—NH—.
Q is (f) and L is *CH$_2$—NH—.
Q is (g) and L is *CH$_2$—NH—.
Q is (h) and L is *CH$_2$—NH—.
Q is (i) and L is *CH$_2$—NH—.
Q is (j) and L is *CH$_2$—NH—.
Q is (k) and L is *CH$_2$—NH—.
Q is (l) and L is *CH$_2$—NH—.
Q is (m) and L is *CH$_2$—NH—.
Q is (n) and L is *CH$_2$—NH—.
Q is (o) and L is *CH$_2$—NH—.
Q is (p) and L is *CH$_2$—NH—.
Q is (q) and L is *CH$_2$—NH—.
Q is (r) and L is *CH$_2$—NH—.
Q is (s) and L is *CH$_2$—NH—.
Q is (t) and L is *CH$_2$—NH—.
Q is (u) and L is *CH$_2$—NH—.
Q is (a) and L is *NH—NH—.
Q is (b) and L is *NH—NH—.
Q is (c) and L is *NH—NH—.
Q is (d) and L is *NH—NH—.
Q is (e) and L is *NH—NH—.
Q is (f) and L is *NH—NH—.
Q is (g) and L is *NH—NH—.
Q is (h) and L is *NH—NH—.
Q is (i) and L is *NH—NH—.
Q is (j) and L is *NH—NH—.
Q is (k) and L is *NH—NH—.
Q is (l) and L is *NH—NH—.
Q is (m) and L is *NH—NH—.
Q is (n) and L is *NH—NH—.
Q is (o) and L is *NH—NH—.
Q is (p) and L is *NH—NH—.
Q is (q) and L is *NH—NH—.
Q is (r) and L is *NH—NH—.
Q is (s) and L is *NH—NH—.
Q is (t) and L is *NH—NH—.
Q is (u) and L is *NH—NH—.
Q is (a) and L is absent,
Q is (b) and L is absent,
Q is (c) and L is absent,
Q is (d) and L is absent,
Q is (e) and L is absent,
Q is (f) and L is absent,
Q is (g) and L is absent,
Q is (h) and L is absent,
Q is (i) and L is absent,
Q is (j) and L is absent,
Q is (k) and L is absent,
Q is (l) and L is absent,
Q is (m) and L is absent,
Q is (n) and L is absent,
Q is (o) and L is absent,
Q is (p) and L is absent,
Q is (q) and L is absent.
Q is (r) and L is absent,
Q is (s) and L is absent,
Q is (t) and L is absent,
Q is (u) and L is absent.

In some embodiments, including any one or more of the embodiments for Q and L and combinations thereof, $R^a$ is selected from hydrogen, halo (e.g. chloro, fluoro, bromo, iodo), $C_{1-6}$alkyl, halo$C_{1-6}$alkyl (e.g trihalo$C_{1-6}$alkyl), $C_{1-6}$alkoxy, halo$C_{1-6}$alkoxy, $C_{1-6}$alkoxy $C_{1-6}$alkyl, $C_{1-6}$alkoxy $C_{1-6}$alkoxy, $C_{3-6}$cycloalkyl, $C_{3-6}$cycloalkyl-$C_{1-6}$alkyl, $C_{3-6}$cycloalkoxy, phenyl, phenyl$C_{1-6}$alkyl (e.g. benzyl), 5-6 membered heterocyclyl, and 5-6 membered heteroaryl.

In some embodiments, including any of the embodiments for Q, L and $R^a$, and combinations thereof, A is N.

In some embodiments, including any of the embodiments for Q, L and $R^a$, and combinations thereof, A is C—$R^b$. In some embodiments, where $R^b$ is C(=N$R^c$)NH$R^d$ or —C(=O)NH$R^d$, $R^c$ and $R^d$ are independently selected from hydrogen, hydroxy, $C_{1-6}$alkyl, phenyl, $C_{3-6}$cycloalkyl, C(=O)$C_{1-6}$alkyl, 5-6 ring membered heteroaryl and 5-6 ringmembered heterocyclyl. In some examples thereof, $R^b$ is selected from OH, —C(=N—OH)NH$_2$ and —C(=NH)NH$_2$. In further embodiments, $R^b$ is selected from —C(=N—OH)NH$_2$ and —C(=NH)NH$_2$. In other examples' $R^b$ may be a cyclic group of formula (i), (ii), or (iii). In formula (ii) R' may be methyl, ethyl, propyl (n- and i-), butyl, (n-, sec- and tert-), pentyl (straight and branched) and hexyl (straight and branched). In formula (iii), n can be 0, 1, 2, 3, 4, 5 or 6. In some embodiments of formula (iii), n is 0 or 1. In further embodiments, n is 1. In some embodiments of formula (iii), one of Z is OH. In further examples thereof, two of Z are OH. In still other examples thereof, three of Z are OH. In still other examples of (iii), all Z are hydrogen. It will be appreciated that where a Z group is OH a stereogenic centre is formed. The disclosure includes substantially optically pure forms (for example at least 95%, 96%, 97%, 98%, or 99% optically pure) at any one or more such centres, such as substantially pure enantiomers and diastereomers, as well as mixtures of stereoisomers, including racemates.

Some exemplary embodiments of cyclic $R^b$ described above include:

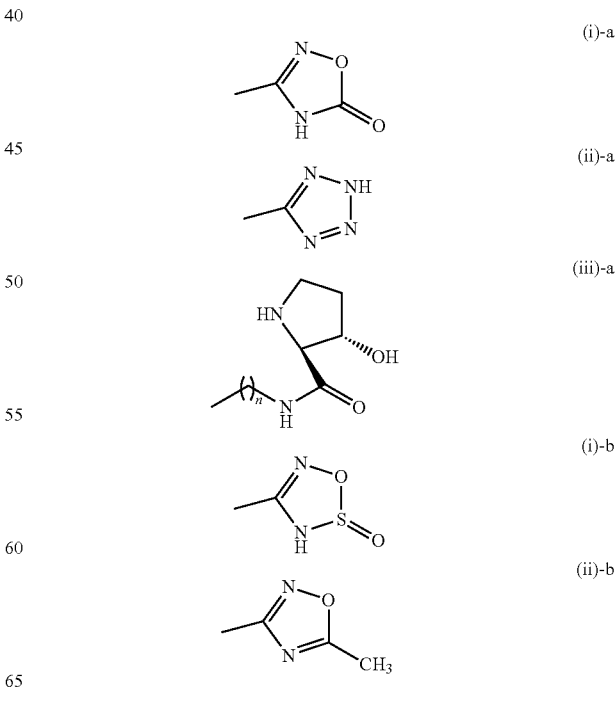

where n is 0 or 1.

In still further embodiments, $R^b$ is selected from —C(=N—OH)NH$_2$, —C(=NH)NH$_2$ and a cyclic group of formula (i), (ii) or (iii), such as (i)-a, (i)-b, (ii)-a, (ii)-b and (iii)-a.

In further embodiments, compounds contemplated herein have an $R^a$ group and an $R^b$ group each selected from the respective paragraphs described immediately above.

In some further embodiments, $R^a$ is halo, and L is NH.

In other embodiments, $R^a$ is halo, and L is *C(=O)NH.

In other embodiments, $R^a$ is halo, and L absent.

In some embodiments, the disclosure contemplates a compound of Formula (Ia)

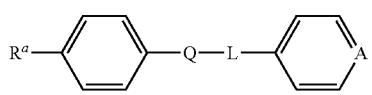

(Ia)

wherein

L is a bivalent linker group selected from —NH—, —*NH—CH$_2$—, —*CH$_2$—NH—, *NH—NH—, and —*C(=O)—NH—, wherein the linker atom labelled * is bonded to Q;

A is C—$R^b$, where $R^b$ is selected from C(=NR$^c$)NHR$^d$ and a cyclic group selected from formula (i)-(iii) above; and where Q, and $R^a$ are as described for formula (I) or any embodiments of Q and $R^a$ as described above.

In further examples of Formula (Ia), $R^b$ is selected from —C(=N—OH)NH$_2$, —C(=NH)NH$_2$ and a cyclic group of formula (i)-a, (i)-b, (ii)-a, (ii)-b and (iii)-a.

In some embodiments, the disclosure relates to compounds of Formula (IA), having Q, L, $R^a$ and $R^b$ as defined for Formula (Ia), but where $R^b$ may also be OH, subject to provisos (v), (ix), (xi) and (xiv) described for Formula (I).

In some embodiments of Formulae (I) and (IA), including any one or more of the embodiments for Q and L, and combinations thereof, as described above, $R^a$ is halo and $R^b$ is OH, C(=NH)NH$_2$, C(=N—OH)NH$_2$, or a cyclic group of formula (i)-a, (i)-b, (ii)-a, (ii)-b or (iii)-a. In further embodiments thereof, L is NH, C(=O)NH, or absent.

In some embodiments, of Formulae (I), and (IA), Q is an oxadiazolyl group selected from (c), (d) and (k), $R^a$ is selected from hydrogen, halo (e.g. chloro, fluoro, bromo, iodo), alkyl (e.g. C$_{1-6}$alkyl), haloalkyl, (e.g trihaloC$_{1-6}$alkyl, such as trifluoromethyl), alkoxy (e.g. C$_{1-6}$alkoxy), aryl, such as phenyl, and heteroaryl, wherein the aryl and heteroaryl groups may be unsubstituted or further substituted by one or more optional substituents as described herein, and $R^b$ is selected from OH, C(=NH)NH$_2$, C(=N—OH)NH$_2$, or a cyclic group of formula (i)-a, (i)-b, (ii)-a, (ii)-b or (iii)-a. In further embodiments thereof, Q is (k).

In some embodiments of Formulae (I), (IA) and (Ia), Q is (k) and L is NH. In still further embodiments, $R^a$ is hydrogen or halo, such as chloro or iodo.

In some embodiments of Formulae (I) and (IA) $R^a$ is a halogen, Q is (k), L is NH and $R^b$ is OH or —C(=NR$^c$)NHR$^d$. In further examples thereof, $R^a$ is chloro or iodo. In still further examples, $R^b$ is selected from OH, —C(=NH)NH$_2$, —C(=N—OH)NH$_2$, or a cyclic group of formula (i)-a, (i)-b, (ii)-a, (ii)-b or (iii)-a.

In some embodiments of Formulae (I) and (IA) $R^a$ is a halogen, Q is (c), (d) or (k), L is absent and $R^b$ is OH, —C(=NR$^c$)NHR$^d$, C(=O)NHR$^d$, or a cyclic group of formula (i)-(iii). In further examples thereof, $R^a$ is chloro or iodo. In still further examples thereof $R^b$ is selected from OH, —C(=NH)NH$_2$, —C(=N—OH)NH$_2$, C(=O)NH$_2$, or a cyclic group of formula (i)-a, (i)-b, (ii)-a, (ii)-b or (iii)-a.

In some embodiments, Q is (k), L is absent and $R^b$ is OH, C(=NOH)NH$_2$, C(=NH)NH$_2$, CONH$_2$, or a group of formula (i)-a, (i)-b, (ii)-a, (ii)-b or (iii)-a, . In further embodiments thereof, $R^a$ as described for any of the embodiments above.

In some embodiments of Formulae (I), (IA) and (Ia), L is *C(=O)—NH and Q is (c), (d), (f), (h), (i) (k).

In some embodiments of Formulae (I), (IA) and (Ia), L is NH and Q is (i) or (c), (h).

In some embodiments of Formulae (I), (IA) and (Ia), L is NH or NH—NH and Q is (d).(g), (k) or (p).

In some embodiments, L is NH or *C(=O)—NH, $R^a$ is halo (e.g. Cl, I Br or F) or halo C$_{1-6}$alkyl (e.g. CF$_3$), and $R^b$ is a group of formula (i)-b or C(=NOH)NH$_2$.

The disclosure also contemplates bioisosteres, which can be defined as compounds or groups which possess near equal molecular shapes and volumes, approximately the same distribution of electrons and which exhibit similar physical properties (*Pro. Drug Res.,* 1991, 37, 287). It will be understood that when $R^b$ is an OH group, this forms a phenol moiety and the disclosure also contemplates compounds having phenol bioisosteres. Some exemplary phenol bioisosteres are formed when the OH radical is replaced by B(OH)$_2$, or BF$_3$.M (M=Na, K, Ca, or Mg). Accordingly, in any one or more of the embodiments described herein, including compounds depicted in Table 2, OH may be replaced by B(OH)$_2$, or BF$_3$.M (M=Na, K, Ca, or Mg), or B(OH)$_2$, and/or BF$_3$.M (M=Na, K, Ca, or Mg) may be included as further alternatives for $R^b$.

In certain embodiments, compounds contemplated herein have any one two, three or more of Q, $R^a$, $R^b$, $R^c$, $R^d$, and L as per any one or more of the Compounds E-1-E-32 depicted in Table 2 herein.

Thus, in further examples, compounds contemplated have Q and $R^a$ as per any one of the Compounds E-1-E-32 depicted in Table 2 herein.

In other examples, the compounds contemplated have Q and A as per any one of the Compounds E-1-E-32 depicted in Table 2 herein.

In other examples, the compounds contemplated have Q and L as per any one of the Compounds E-1-E-32 depicted in Table 2 herein.

In other examples, the compounds contemplated have L and $R^a$ as per any one of the Compounds E-1-E-32 depicted in Table 2 herein.

In other examples, the compounds contemplated have L and $R^b$ as per any one of the Compounds E-1-E-32 depicted in Table 2 herein.

In other examples, the compounds contemplated have Q, L and $R^a$ as per any one of the Compounds E-1-E-32 depicted in Table 2 herein.

In other examples, the compounds contemplated have Q, L and $R^b$ as per any one of the Compounds E-1-E-32 depicted in Table 2 herein.

The compounds contemplated herein may be prepared by any appropriate means known for generating heterocyclic compounds. Some exemplary methods are described in Example 1 hereinafter and graphically depicted in Schemes 1-13 below. The skilled person can extrapolate these to the synthesis of other compounds of Formulae (I), (IA) and (Ia) (for example by replacement of the appropriately substituted phenyl ring (for compounds where A is C—$R^b$) with a pyridyl ring (for compounds where A is N, and vice versa).

Compounds where Q is (i) and L is *C(=O)—NH may be prepared according to Schemes 1.
Compounds where Q is (c) and L is NH may be prepared according to Scheme 3:
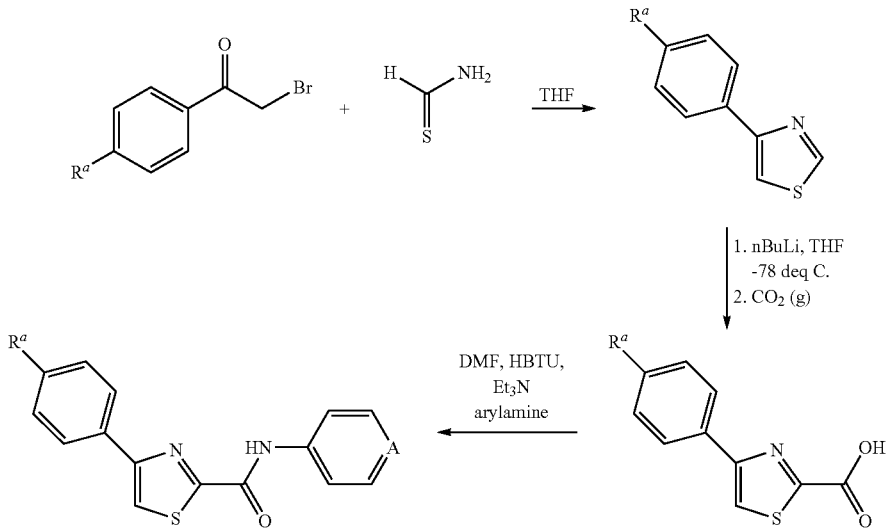
Compounds where Q is (i) and L is NH may be prepared according to Scheme 2:
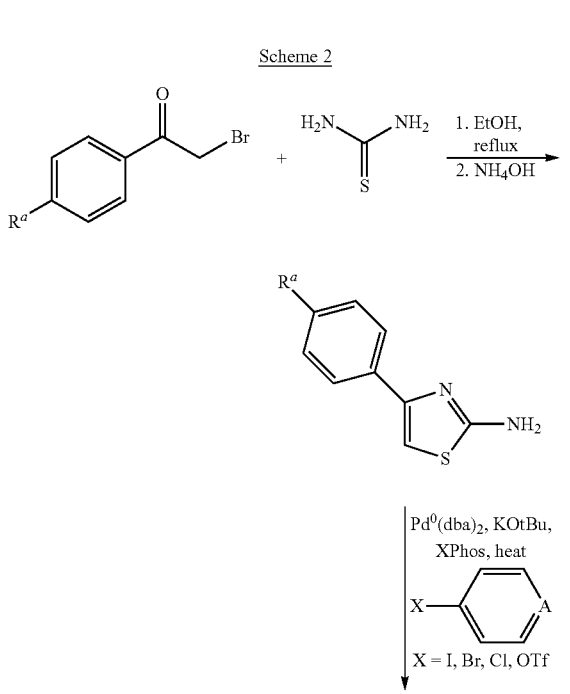
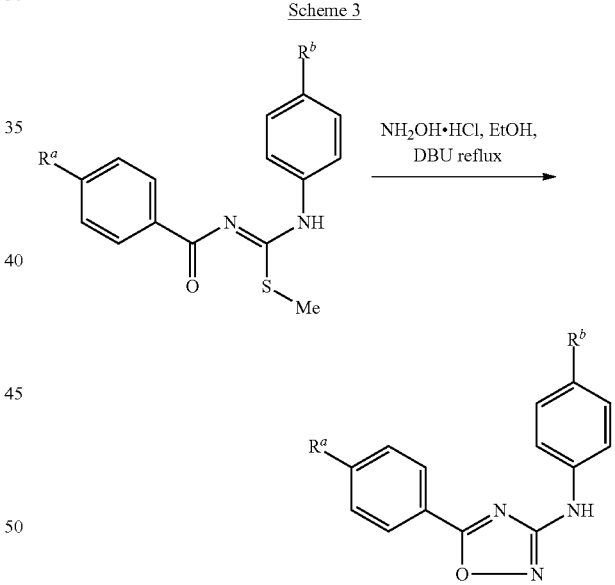
Compounds where Q is (d) and L is NH and —NH—NH— may be prepared according to Scheme 4:
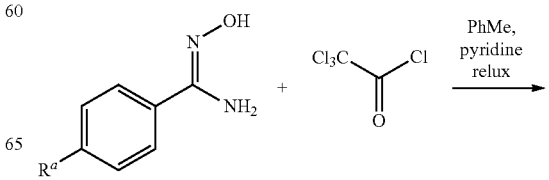

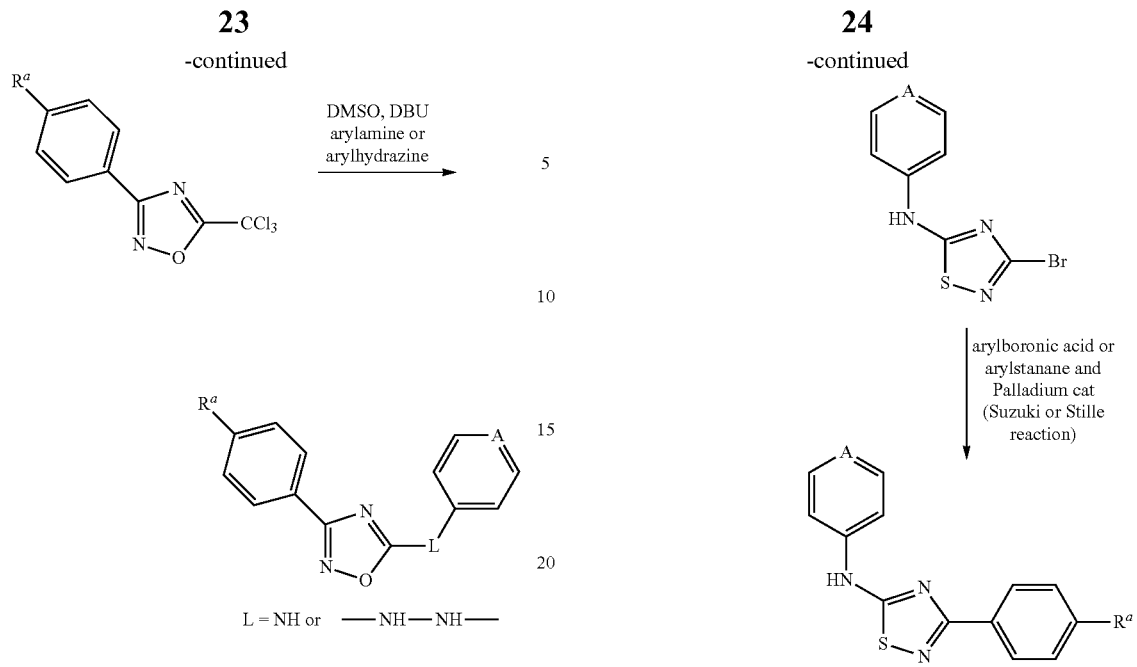
Compounds where Q is (k) or (p) and L is NH or —NH—NH— may be prepared according to Scheme 5:
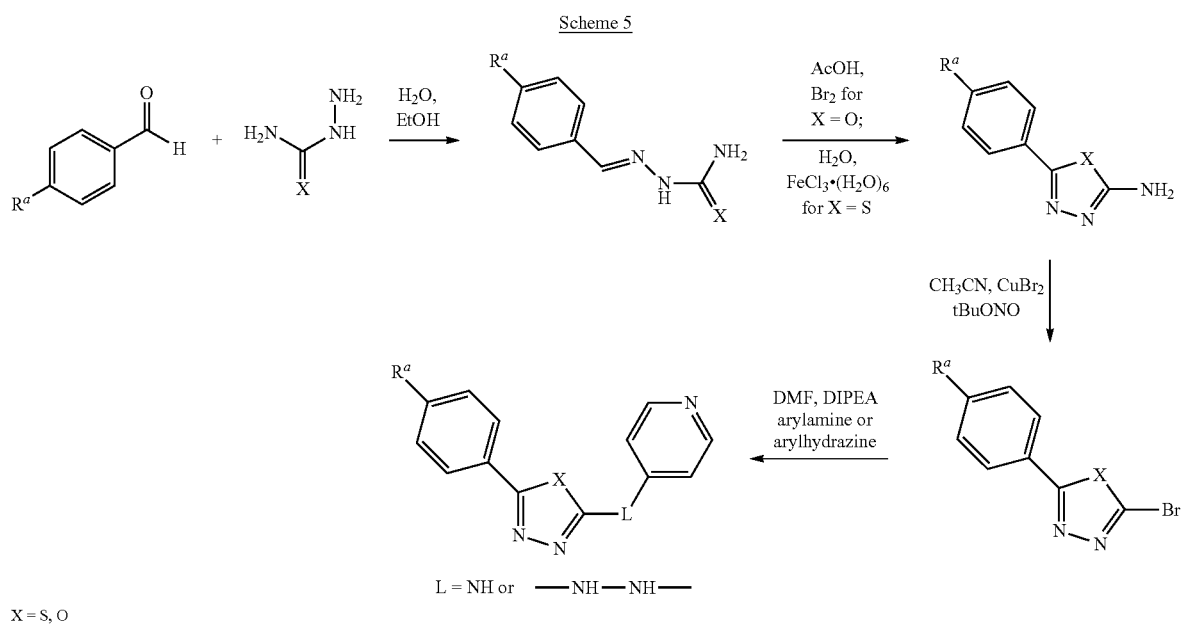
Compounds where Q is (h) and L is NH may be prepared according to Scheme 7:
Compounds where Q is (g) and L is NH or —NH—NH— may be prepared according to Scheme 8:

-continued
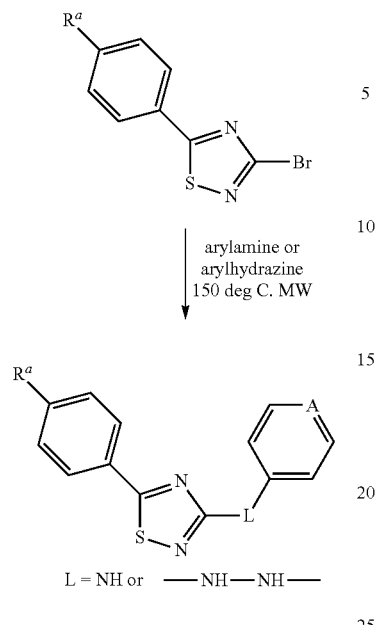
Compounds where Q is (f) and L is *C(=O)—NH may be prepared according to Scheme 9:
Scheme 9
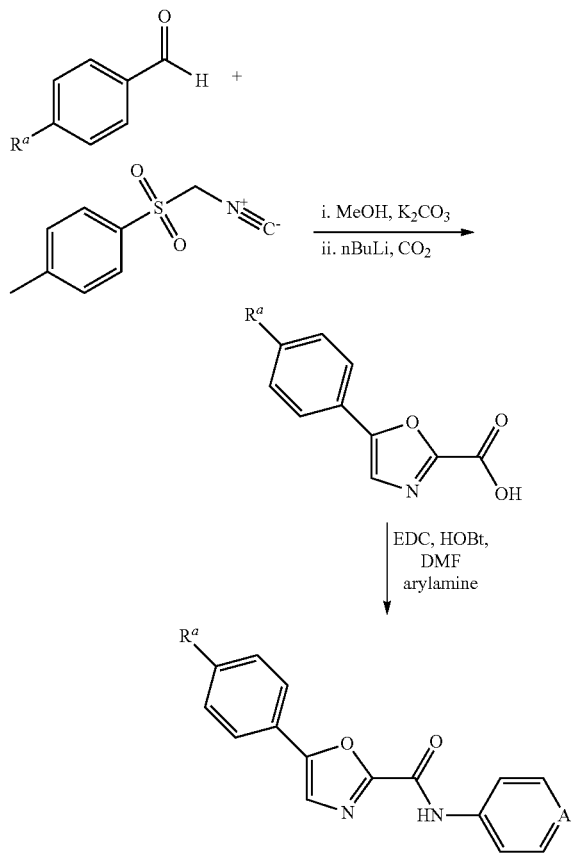
Compounds where Q is (k) and L is *C(=O)—NH may be prepared according to Scheme 10:
Scheme 10
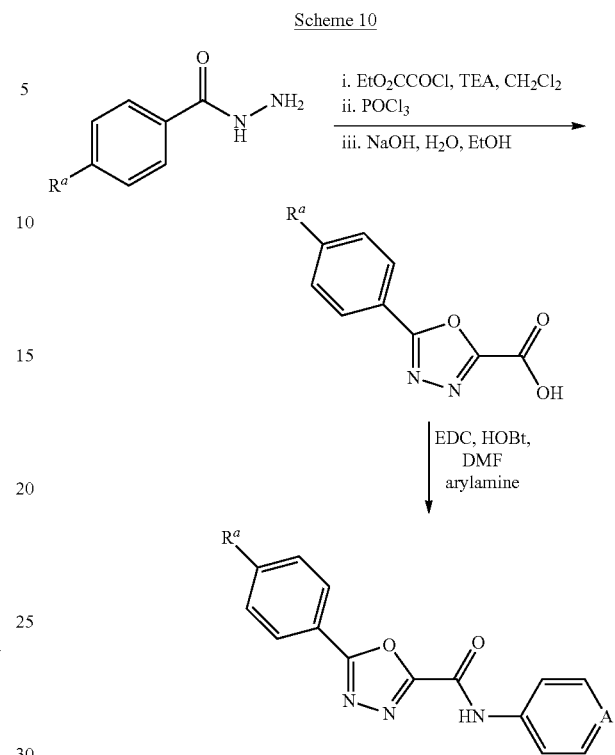
Compounds where Q is (d) and L is *C(=O)NH may be prepared according to Scheme 11:
Scheme 11
Compounds where Q is (c) and L is *C(=O)NH may be prepared according to Scheme 12:

Scheme 12

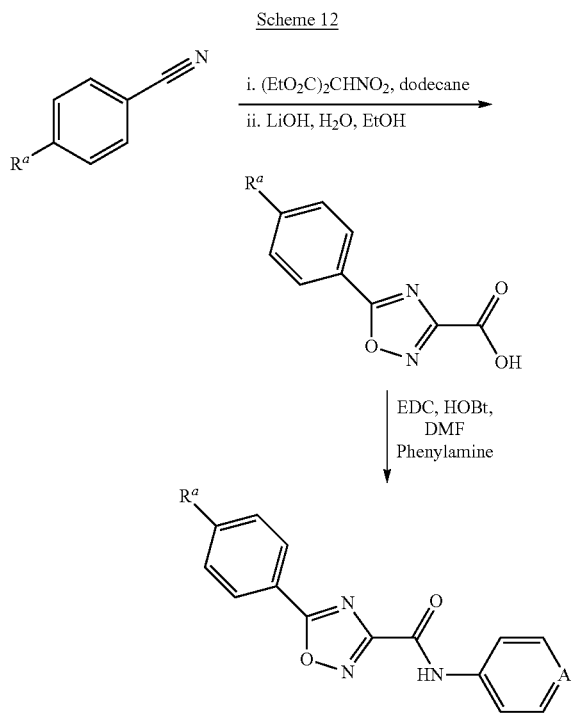

Compounds where Q is (h) and L is *C(=O)—NH may be prepared according to Scheme 13:

Scheme 13

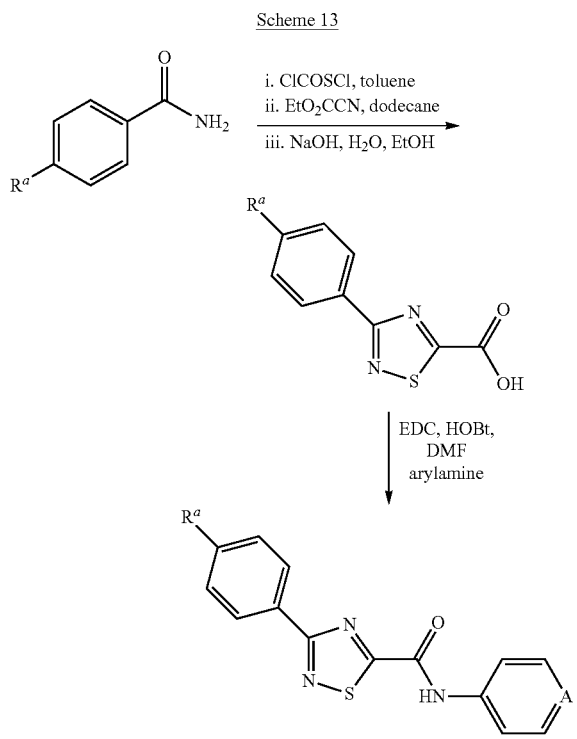

It will be recognised that during the processes for the preparation of compounds contemplated by the present invention, it may be necessary or desirable to protect certain functional groups which may be reactive or sensitive to the reaction or transformation conditions undertaken. Examples of such groups include: OH (including diols), $NH_2$, $CO_2H$, SH and C=O. Suitable protecting groups for such functional groups are known in the art and may be used in accordance with standard practice. As used herein, the term "protecting group", refers to an introduced functionality which temporarily renders a particular functional group inactive under certain conditions. Such protecting groups and methods for their installation and subsequent removal at an appropriate stage are described in *Protective Groups in Organic Chemistry*, $3^{rd}$ Edition, T. W. Greene and P. G. Wutz, John Wiley and Sons, 1999, the entire contents of which are incorporated herein by reference. Exemplary forms of protected groups include:

for amino ($NH_2$)-carbamates (such as Cbz, Boc, Fmoc), benzylamines, acetamides (e.g. acetamide, trifluoroacetamide);

for carbonyl-acetals, ketals, dioxanes, dithianes, and hydrazones;

for hydroxy-ethers (e.g. alkyl ethers, alkoxylalkyl ethers, allyl ethers, silyl ethers, benzyl ethers, tetrahydropyranyl ethers), carboxylic acid esters, acetals (e.g. acetonide and benzylidene acetal);

for thio (SH)-ethers (e.g. alkyl ethers, benzyl ethers), esters; and for $CO_2H$-esters (e.g. alkyl esters, benzyl esters).

It will also be recognised that certain compounds of the disclosure may possess asymmetric centres and are therefore capable of existing in more than one stereoisomeric form, such as enantiomers and diastereomers. The invention thus also relates to optically active compounds and compounds in substantially pure isomeric form at one or more asymmetric centres, e.g., enantiomers having greater than about 90% ee, such as about 95% or 97% ee or greater than 99% ee, as well as mixtures, including racemic mixtures, thereof. Such isomers may be prepared by asymmetric synthesis, for example using chiral intermediates, enzymes, or mixtures may be resolved by conventional methods, e.g., chromatography, recrystallization, or use of a resolving agent.

Without limiting the disclosure by theory, the compounds described herein may target one or more enzymes in the sphingolipid biosynthetic pathway, also referred to herein as sphingolipid enzymes, such as the sphingosine kinases SphK1 and SphK2, and Des1, that is to say they interact with the enzyme. As used herein, the term "interact" when used at least in the context of the compounds of the disclosure and sphingolioid enzymes includes an association of the compound with the enzyme so as to partially or fully initiate, promote or enhance, or, alternatively, inhibit, retard or prevent biochemical activity of the enzyme, (e.g. phosphorylation of sphingosine to generate S1P or introduction of the Δ4 double bond into dihydroceramide to generate ceramide). This may occur through any means such as chemically or associatively binding at one or more sites of the enzyme, promoting reaction with other endogenous molecules or associating in such a manner so as to cause degradation or a conformational change in the enzyme. In certain embodiments, one or more compounds may be capable of inhibiting the activity of the enzyme through binding at the binding domain of the endogenous compound, (orthosteric site) or binding at another site (allosteric site), such as the site of S1P-mediated auto-inhibition. Compounds may be capable of interaction with one or both binding sites. Determination of the interaction of the compounds with one or more enzymes may be determined in accordance with any suitable methods of the art, including methods which measure enzyme activity inhibition, such as the procedures described in the Examples. In some embodiments, a compound may be considered to interact with an enzyme if, in accordance with the procedure used, it demonstrates at least a measurable or otherwise determinable level of enzyme activity inhibition. Selective interaction, e.g. selective inhibition, refers to the interaction of a compound with an enzyme and/or binding site thereof in complete or partial preference over another enzyme and/or binding site.

Without limiting the disclosure by theory, one or more compounds of Formula (I) may interact with only one, two or three of Des1, SphK1 and SphK2. Interaction may be selectively in preference to one enzyme over another. For example a compound may interact selectively with one of Des1, SphK1 and SphK2, but not with the others, or interact to a greater extent with one, such that the activity thereof is inhibited to a greater extent than the others. In other embodiments, one or more compounds of the disclosure may interact selectively with two sphingolipid enzymes in preference to another. For example, a compound may interact selectively with two of Des1, SphK1 and SphK2, but not with the other, or interact with two enzymes such that their activities are inhibited to a greater extent than the other.

One or more compounds of Formula (I) may demonstrate inhibitory activity of SphK1 and/or SphK2 and/or Des1, and/or demonstrate antiproliferative activity and/or demonstrate anti-fibrotic activity.

One or more compounds of Formula (I), or groups of compounds as described in embodiments above, may have selective interacting activity with one of SphK1 or SphK2 over the other, that is to say demonstrate selective interaction with SphK1 over SphK2, or selective interaction with SphK2 over SphK1.

In some embodiments, one or more compounds of formula (I) demonstrate inhibitory activity of SphK1. In some embodiments, certain compounds of formula I demonstrate inhibitory activity of SphK2. In further embodiments certain compounds of formula (I) demonstrate inhibitory activity of SphK1 and SphK2. In other embodiments, certain compounds of formula I demonstrate selective inhibitory activity of SphK1 over SphK2. In still other embodiments, certain compounds of formula I demonstrate selective inhibitory activity of SphK2 over SphK1.

In some embodiments, one or more compounds of Formulae (I), (IA) and (Ia) demonstrate antiproliferative activity. In still further example, the antiproliferative activity may be observed against a single cell line or type, or may be observed in two or more different cell lines or cancer types. Thus, one or more compounds of the disclosure may be useful in therapy against a single cancer type or two or more cancer types. In some further embodiments, certain compounds of Formulae (I), (IA) and (Ia) demonstrate antiproliferative activity without inhibitory activity against SphK1 and SphK2, that is to say they are selective antiproliferative agents. In further embodiments thereof, one or more compounds of Formulae (I), (IA) and (Ia) may also demonstrate inhibitory activity of SphK1 and/or SphK2 as described above.

Without limiting the disclosure by theory, where a compound interacts with SphK1 and or SphK2, disclosure compound may interact with one or more of the orthosteric and allosteric sites of SphK1 and SpK2. In some embodiments, one or more compounds of the disclosure may interact selectively with one or other of the orthosteric and allosteric sites of SphK1/2. Thus, in some embodiments, one or more compounds of the disclosure may interact selectively with the orthosteric site of SphK1 and/or SphK2, and inhibit kinase activity. In other embodiments, one or more compounds of the disclosure may interact selectively with the allosteric site of SphK1 and/or SphK2, and inhibit kinase activity Further the interaction may be selective for one of SphK1 and SphK2 over the other. Compounds which inhibit kinase activity may have utility in the therapy of diseases or conditions such as inflammation, asthma and pain.

In some embodiments, one or more compounds of the disclosure may interact selectively with one or other of the allosteric sites of SphK1 and SpK2. Without limiting the disclosure by theory, such interaction may result in degradation of the kinase. Compounds which interact in such a manner may have utility in the therapy of diseases and conditions in which undesirable cell proliferation or metastasis is implicated or involved.

In some embodiments, one or more compounds of the disclosure may interact with both sites of SphK1 and/or SpK2.

In some embodiments, one or more compounds of the disclosure may interact with Des1. In further embodiments, one or more compounds of the disclosure may interact with Des1 and at least one of SphK1 and SpK2. In further embodiments one or more compounds of the disclosure may interact with Des1 and SphK1. In still further embodiments, one or more compounds of the disclosure may interact with Des1 and SpK2. In still further embodiments, one or more compounds of the disclosure may interact with Des1 and SphK1 and SphK2. In the embodiments, where a compound interacts with Des1 and also with at least one of SphK1 and SpK2, that interaction may be at any one of the sites for the enzyme, for example, the orthosteric site of SphK1 or SpK2, the allosteric site of SphK1 or SpK2, the orthosteric sites of both SphK1 and SpK2, the allosteric sites of both SphK1 and SpK2, the orthosteric site of SphK1 and the allosteric site of SphK2, or the allosteric site of SphK1 and the orthosteric site of SphK2.

In some embodiments, one or more compounds may interact with Des1 and SphK2, and demonstrate antiproliferative and/or antifibrotic activity.

Subjects to be treated include mammalian subjects: humans, primates, livestock animals (including cows, horses, sheep, pigs and goats), companion animals (including dogs, cats, rabbits, guinea pigs), and captive wild animals. Laboratory animals such as rabbits, mice, rats, guinea pigs and hamsters are also contemplated as they may provide a convenient test system. Non-mammalian species such as birds, amphibians and fish may also be contemplated in certain embodiments of the invention.

The compounds of the disclosure may be useful in treating a disease or condition in which excessive or undesirable sphingolipid enzyme activity is implicated, such as where undesirable cell proliferation is involved, including the treatment or inhibition of cancer and/or metastases, or the treatment of fibrotic diseases, and may be administered to a subject in a treatment or inhibiting effective amount. A treatment or inhibiting effective amount is intended to include an amount which, when administered according to the desired dosing regimen, at least partially attains the desired therapeutic treatment or inhibiting effect, and may include one or more of: alleviating, eliminating or reducing the frequency of occurrence of one or more symptoms of, preventing or delaying the onset of, inhibiting the progression of, or halting or reversing (partially or altogether) the onset or progression of the particular disorder or condition, or pathology thereof, being treated. As used herein, "inhibiting undesirable cell proliferation", includes preventing, arresting, retarding the rate or extent of, or otherwise delaying or reversing excessive, uncontrolled, detrimental or otherwise undesirable cell proliferation, such as may occur in cancer growth or metastasis.

The compounds of the disclosure or their salts or solvates may therefore be useful as anti-proliferative agents e.g. in treating undesirable cell proliferation as, such as found in cancerous conditions, including hormone-related cancers, such as breast cancer and prostate cancer, and their metastasis. Other cancerous conditions which may be amenable to treatment by the compounds described herein include lung, colon, pancreatic and brain cancer as well as lymphoma. The compounds described herein may have utility in treating primary cancers and/or treating or inhibiting metastases (i.e. secondary cancers).

It has now been demonstrated that some compounds of Formula (I) which inhibit the enzyme Des1 also have anti-fibrotic activity. Therefore, in some embodiments, compounds, which inhibit Des 1, including their pharmaceutically acceptable salts and solvates, may be useful in the treatment of fibrosis and fibrotic diseases, such as, pulmonary (lung) fibrosis, including idiopathic pulmonary fibrosis and cystic fibrosis; liver fibrosis, such as cirrhosis; cardiac (heart) fibrosis, including endomyocardial fibrosis, atrial fibrosis, and fibrosis resulting from myocardial infarction heart attack); kidney fibrosis, such as resulting from diabetic nephropathy; gall bladder fibrosis, skin or dermal fibrosis, such as scleroderma, hypertrophic scarring and keloids; bone marrow fibrosis, and intestinal fibrosis, such as Crohn's disease.

One or more compounds contemplated herein may advantageously demonstrate one or more of increased efficacy or potency (for example, as a sphingosine kinase inhibitor, Des1 inhibitor, anti-proliferative agent or anticancer agent or anti-fibrotic agent) and reduced metabolic and/or toxophoric liability when compared to other known sphingolipid enzyme inhibitors, such as SKI-II as described herein.

Suitable dosage amounts and dosing regimens can be determined by the attending physician and may depend on the particular condition being treated, the severity of the condition as well as the general age, health and weight of the subject. Suitable dosage amounts may lie in the range of from 1 μg to 1 g of compound, salt or solvate, for example, 1 μg-1 mg (such as 100 μg, 250 μg, 500 μg, 750 μg), 1 mg-10 mg (such as 2, 5 or 7 mg), 10 mg-50 mg (such as 15, 20, 25, 30, or 40 mg), 50 mg-100 mg (such as 60, 70, 80, 90 mg) or 100 mg-500 mg (such as 200, 250, 300, 400 mg). Dosages may be administered once, or multiple times daily (e.g. 2, 3, or 4 times), or one or more times weekly, fortnightly or monthly. Administration may be over a limited period of time to treat an acute disorder or condition, for example 1, 2, 3, or 4 weeks, or 2 or 3 months, or may occur over extended periods to treat a chronic disorder or condition, for example greater than 3 months, e.g. 6 or 12 months, 1-2 years or longer.

The active ingredient may be administered in a single dose or a series of doses. While it is possible for the active ingredient to be administered alone, it is preferable to present it as a composition, preferably as a pharmaceutical composition, with one or more pharmaceutically acceptable additives. The compounds may also be packaged or presented as a combination with one or more other therapeutic agents and/or anti-proliferative or anti-cancer agents. The components of the combinations may be administered in conjunction with each other, either contemporaneously or at separate times, as a single composition or separate compositions, as appropriate. Thus, the compositions contemplated herein may contain the compounds of the disclosure, or a pharmaceutically acceptable salt or solvate thereof, as the only therapeutic agent or anti-proliferative/anti-cancer or anti-fibrotic agent, or may further contain one or more additional therapeutic or anti-proliferative/anti-cancer or anti-fibrotic agents. Thus, the present disclosure also relates to the use of a compound of Formula (I), (IA) or (Ia) or a pharmaceutically acceptable salt or solvate thereof in the manufacture of a medicament for treating a disease or condition in which excessive or undesirable sphingosine kinase activity is implicated, or inhibiting undesirable cell proliferation, e.g. in treating cancer or inhibiting or preventing metastasis, or treating fibrotic diseases.

The formulation of such compositions is well known to those skilled in the art, see for example, *Remington's Pharmaceutical Sciences*, 21$^{st}$ Edition, Mack Publishing, 2005. The composition may contain any suitable additives, carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents.

The additive must be pharmaceutically acceptable in the sense of being compatible with the other ingredients of the composition and not injurious to the subject. Compositions include those suitable for oral, rectal, nasal, topical (including dermal, buccal and sublingual), vaginal or parental (including subcutaneous, intramuscular, intravenous and intradermal) administration. The compositions may conveniently be presented in unit dosage form and may be prepared by any methods well known in the art of pharmacy. Such methods include the step of bringing into association the active ingredient with the additive which constitutes one or more accessory ingredients. In general, the compositions are prepared by uniformly and intimately bringing into association the active ingredient with liquid additive or finely divided solid additive or both, and then if necessary shaping the product.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. inert diluent), preservative disintegrant (e.g. sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured base, usually sucrose and acacia or tragacanth gum; pastilles comprising the active ingredient in an inert basis such as gelatin and glycerin, or sucrose and acacia gum; and mouthwashes comprising the active ingredient in a suitable liquid carrier.

Compositions suitable for topical administration to the skin may comprise the compounds dissolved or suspended in any suitable carrier or base and may be in the form of lotions, gel, creams, pastes, ointments and the like. Suitable carriers include mineral oil, propylene glycol, polyoxyethylene, polyoxypropylene, emulsifying wax, sorbitan monostearate, polysorbate 60, cetyl esters wax, cetearyl alcohol, 2-octyldodecanol, benzyl alcohol and water. Devices for transdermal delivery, such as patches, may also be used to administer the compounds of the invention.

Compositions for rectal administration may be presented as a suppository with a suitable base comprising, for example, cocoa butter, glycerin, gelatin or polyethylene glycol.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as herein above described, or an appropriate fraction thereof, of the active ingredient.

It should be understood that in addition to the active ingredients particularly mentioned above, the compositions of this disclosure may include other additives or agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

The present disclosure also relates to prodrugs of Formula (I). Any compound that is a prodrug of a compound of Formula (I) is within the scope and spirit of the invention. The term "prodrug" is used in its broadest sense and encompasses those derivatives that are converted in vivo, either enzymatically or hydrolytically, to the compounds of the invention. Such derivatives would readily occur to those skilled in the art, and include, for example, compounds where a free thiol or hydroxy group is converted into an ester, such as phosphonate, sulphonate and carboxy esters, such as an acetate, or thioester or where a free amino group is converted into an amide such as a carboxy, phosphonate or sulphonate amide. Procedures for acylating the compounds of the invention, for example to prepare ester and amide prodrugs, are well known in the art and may include treatment of the compound with an appropriate carboxylic acid, anhydride or chloride in the presence of a suitable catalyst or base. Esters of carboxylic acid (carboxy) groups are also contemplated. Suitable esters $C_{1-6}$alkyl esters; $C_{1-6}$alkoxymethyl esters, for example methoxymethyl or ethoxymethyl; $C_{1-6}$alkanoyloxymethyl esters, for example, pivaloyloxymethyl; phthalidyl esters; $C_{3-8}$cycloalkoxycarbonyl$C_{1-6}$alkyl esters, for example, 1-cyclohexylcarbonyloxyethyl; 1,3-dioxolen-2-onylmethyl esters, for example, 5-methyl-1,3-dioxolen-2-onylmethyl; and $C_{1-6}$alkoxycarbonyloxyethyl esters, for example, 1-methoxycarbonyloxyethyl. Prodrugs of amino functional groups include amides (see, for example, *Adv. BioSci.*, 1979, 20, 369, Kyncl, J. et al), enamines (see, for example, *J. Pharm. Sci.*, 1971, 60, 1810, Caldwell, H. et al), Schiff bases (see, for example, U.S. Pat. No. 2,923,661 and *Antimicrob. Agents Chemother.*, 1981, 19, 1004, Smyth, R. et al), oxazolidines (see, for example, *J. Pharm. Sci,* 1983, 72, 1294, Johansen, M. et al), Mannich bases (see, for example, *J. Pharm. Sci.* 1980, 69, 44, Bundgaard, H. et al and *J. Am. Chem. Soc.*, 1959, 81, 1198, Gottstein, W. et al), hydroxymethyl derivatives (see, for example, *J. Pharm. Sci,* 1981, 70, 855, Bansal, P. et al) and N-(acyloxy)alkyl derivatives and carbamates (see, for example, *J. Med. Chem.*, 1980, 23, 469, Bodor, N. et al, *J. Med. Chem.*, 1984, 27, 1037, Firestone, R. et al, *J. Med. Chem.*, 1967, 10, 960, Kreiger, M. et al, U.S. Pat. No. 5,684,018 and *J. Med. Chem.*, 1988, 31, 318-322, Alexander, J. et al). Other conventional procedures for the selection and preparation of suitable prodrugs are known in the art and are described, for example, in WO 00/23419; *Design of Prodrugs*, H. Bundgaard, Ed., Elsevier Science Publishers, 1985; *Methods in Enzymology,* 42: 309-396, K. Widder, Ed, Academic Press, 1985; *A Textbook of Drug Design and Development*, Krogsgaard-Larsen and H. Bundgaard, Eds, Chapter 5, p 113-191 (1991); *Advanced Drug Delivery Reviews,* 8; 1-38 (1992); *Journal of Pharmaceutical Sciences,* 77; 285 (1988), H. Bundgaard, et al; *Chem Pharm Bull,* 32692 (1984), N. Kakeya et al and *The Organic Chemistry of Drug Design and Drug Action*, Chapter 8, pp 352-401, Academic press, Inc., 1992.

Suitable pharmaceutically acceptable salts of compounds of Formula (I), (IA) or (Ia) may include, but are not limited to salts of pharmaceutically acceptable inorganic acids such as hydrochloric, sulphuric, phosphoric nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, tannic, ascorbic, fendizoic, 4-4'-methylenebis-3-hydroxy-2-naphthoic acid, o-(p-hydroxybenzoyl)benzoic, 4'-4"-dihydroxytriphenylmethane-2-carboxylic acid and valeric acids. Base salts include, but are not limited to, those formed with pharmaceutically acceptable cations, such as sodium, potassium, lithium, calcium, magnesium, ammonium and alkylammonium. Basic nitrogen-containing groups may be quaternised with such agents as lower alkyl halide, such as methyl, ethyl, propyl, and butyl chlorides, bromides and iodides or dialkyl sulfates such as dimethyl and diethyl sulfate.

An example of a pharmaceutically acceptable salt of any of the compounds described herein in any of the aspects, embodiments or examples is the hydrochloride salt.

The compounds of the disclosure may be in crystalline form either as the free compounds or as solvates and it is intended that both forms are within the scope of the present invention. The term "solvate" refers to a complex or aggregate formed by one or more molecules of a solute, i.e. compounds of the disclosure, and one or more molecules of a solvent. Suitable solvents are well understood in the art and include for example, of water, i.e. to form hydrates, and common organic solvents such as alcohols (methanol, ethanol, isopropanol) and acetic acid. Methods of solvation are generally known within the art, for example, recrystallization from an appropriate solvent.

The compounds of the disclosure may also be presented for use in veterinary compositions. These may be prepared by any suitable means known in the art. Examples of such compositions include those adapted for:

oral administration, external application (e.g. drenches including aqueous and non-aqueous solutions or suspensions), tablets, boluses, powders, granules, pellets for admixture with feedstuffs, pastes for application to the tongue;

parenteral administration, e.g. subcutaneous, intramuscular or intravenous injection as a sterile solution or suspension;

topical application e.g. creams, ointments, gels, lotions etc.

Some embodiments of the disclosure are now further demonstrated by the following examples which are included for the purpose of illustration and are not intended to limit the generality of the disclosure hereinbefore described.

EXAMPLES

Example 1

Preparation of Test Compounds 1. 5-(4-Chlorophenyl)-N-(4-hydroxyphenyl)-1,3,4-oxadiazol-2-amine (E-1)

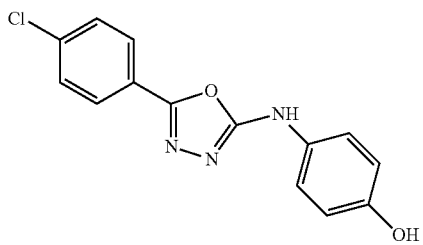 [SMILES: Oc1ccc(Nc2nnc(-c3ccc(Cl)cc3)o2)cc1]

2-Bromo-5-(4-chlorophenyl)-1,3,4-oxadiazole (Vachal, P.; Toth, L. M. *Tetrahedron Letters* 2004, 45, 7157-7161) (0.1 g, 0.385 mmol), 4-aminophenol (0.105 g, 0.963 mmol) and DIPEA (164 µL, 0.963 mmol) in DMF (1.5 mL) were heated at 70° C. for 3 h. The cooled solution was partitioned between EtOAc (150 mL) and water (100 mL). The aqueous layer was removed and the organic layer was washed with water (3×100 mL), then brine (20 mL). The organic layer was dried (MgSO$_4$), filtered and then concentrated to a black residue that filtered through a silica plug eluting with EtOAc and concentrated to a residue that was chromatographed on silica gel eluting with 50% EtOAc:petroleum spirit. The appropriate fractions were pooled and concentrated to a solid that was triturated with EtOAc providing the title compound as a beige solid (0.031 g, 28% yield). Mp 252° C. dec. $^1$H NMR (400 MHz, DMSO) δ 10.31 (s, 1H), 9.16 (s, 1H), 7.87 (d, J=8.6 Hz, 2H), 7.63 (d, J=8.6 Hz, 2H), 7.39 (d, J=8.9 Hz, 2H), 6.77 (d, J=8.9 Hz, 2H). $^{13}$C NMR (101 MHz, DMSO) δ 160.4, 156.7, 152.6, 135.3, 130.3, 129.5, 127.1, 122.9, 119.0, 115.5. LCMS R$_f$ (min)=5.44. MS m/z 288.0 (M+H). HR-ESI calcd for C$_{14}$H$_{11}$ClN$_3$O$_2^+$ (M+H) 288.0534, found 288.0534.

2. 4-((5-(4-Chlorophenyl)-1,3,4-thiadiazol-2-yl)amino)phenol (E-2)

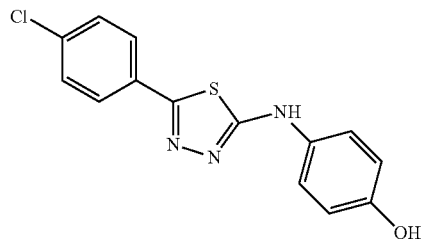 [SMILES: Oc1ccc(Nc2nnc(-c3ccc(Cl)cc3)s2)cc1]

2-Bromo-5-(4-chlorophenyl)-1,3,4-thiadiazole (commercially available) (0.53 g, 1.925 mmol), 4-methoxyaniline (0.595 g, 4.815 mmol) and DIPEA (820 µL, 4.815 mmol) in DMF (1 mL) were heated at 100-105° C. for 2 days. The cooled solution was partitioned between EtOAc (150 mL) and dilute HCl (100 mL). The aqueous layer was removed and the organic layer was washed with water (3×100 mL), then brine (20 mL). The organic layer was dried (MgSO4), filtered and then concentrated to a semi-solid that was triturated with DCM providing the intermediate methyl ether as a golden coloured solid that was filtered and washed with DCM (0.132 g, 22% yield). $^1$H NMR (400 MHz, DMSO) δ 10.36 (s, 1H), 7.90-7.81 (m, 2H), 7.61-7.51 (m, 4H), 7.00-6.91 (m, 2H), 3.74 (s, 3H). A portion of the methyl ether (0.05 g, 0.157 mmol) was suspended in dry DCM (5 mL) in an N$_2$ atm and neat BBr$_3$ (19 µL, 0.2 mmol) was added at 0° C. and stirred at this temperature for 3 h. Then saturated bicarbonate (1 mL) was added to the mixture dropwise, followed by EtOAc (20 mL) and vigorously stirred for 2 min. Then water (5 mL) was added to the stirred solution followed by 6M HCl until pH 2 was reached. The aqueous layer was removed and the organic layer was washed with water (3×30 mL), then brine (20 mL). The organic layer was dried (MgSO4), filtered and then concentrated to a solid that was triturated with EtOAc that was filtered and washed with EtOAc and finally CHCl$_3$ providing the title compound as a light brown powder (0.013 g, 27% yield). Mp 252° C. dec. $^1$H NMR (400 MHz, DMSO) δ 10.22 (s, 1H), 9.23 (s, 1H), 7.84 (d, J=8.7 Hz, 2H), 7.55 (d, J=8.7 Hz, 2H), 7.41 (d, J=8.9 Hz, 2H), 6.77 (d, J=8.9 Hz, 2H). $^{13}$C NMR (101 MHz, DMSO) δ 165.5, 155.2, 153.1, 134.4, 132.5, 129.4, 129.2, 128.2, 120.0, 115.6. LCMS R$_f$ (min)=5.66. MS m/z 304.0 (M+H). HR-ESI calcd for C14H11ClN3O2+(M+H) 288.0534, found 288.0534.

3. 4-((5-(4-Chlorophenyl)-1,2,4-oxadiazol-3-yl)amino)phenol (E-3)

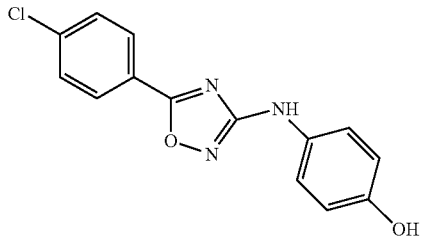 [SMILES: Oc1ccc(Nc2noc(-c3ccc(Cl)cc3)n2)cc1]

Methyl (Z)—N-(4-chlorobenzoyl)-N-(4-hydroxyphenyl)carbamimidothioate (Rasmussen, C. R. et al *Synthesis* 1988, 1988, 456-459) (0.5 g, 1.559 mmol) was added to a mixture of $NH_2$—OH.HCl (0.542 g, 7.795 mmol) and DBU (1.63 mL, 10.913 mmol) in EtOH (20 mL) in which the mixture was refluxed for 4 h. The cooled solution was concentrated to a residue that was taken up in water (30 mL) and neutralised with 6M HCl. The resultant solid was filtered and washed with water providing a white solid (0.308 g). The solid was dissolved in DCM (300 mL) and filtered through a short silica column eluting with 50% EtOAc:petroleum spirit. The solid obtained from concentration of the appropriate fractions was recrystallised from EtOH providing the title compound as a white solid (0.092 g, 21% yield). Mp 119-122° C. $^1$H NMR (400 MHz, DMSO) δ 9.65 (s, 1H), 9.05 (s, 1H), 8.06 (d, J=8.8 Hz, 2H), 7.71 (d, J=8.8 Hz, 2H), 7.30 (d, J=9.0 Hz, 2H), 6.74 (d, J=8.9 Hz, 2H). $^{13}$C NMR (101 MHz, DMSO) δ 171.6, 165.7, 151.9, 137.8, 131.8, 129.7, 129.4, 122.6, 118.7, 115.4. LCMS $R_f$ (min)= 5.80. MS m/z 288.0 (M+H). HR-ESI calcd for $C_{14}H_{11}ClN_3O_2^+$ (M+H) 288.0534, found 288.0532.

4. 4-((3-(4-Chlorophenyl)-1,2,4-oxadiazol-5-yl)amino)phenol (E-4)

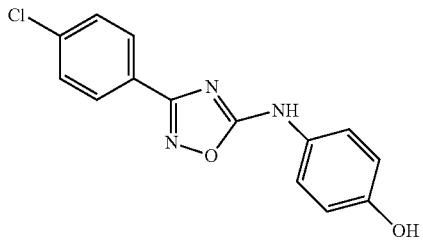 [SMILES: Oc1ccc(Nc2nc(-c3ccc(Cl)cc3)no2)cc1]

3-(4-Chlorophenyl)-5-(trichloromethyl)-1,2,4-oxadiazole (Layton, M. E., et al, *ACS Chemical NeuroScience* 2011, 2, 352-62) (0.613 g, 2.057 mmol) was dissolved in DMSO (9.2 mL) followed by 4-aminophenol (0.748 g, 6.859 mmol) and DBU (1.04 mL, 6.909 mmol) at rt. The mixture was stirred at for 3 h then diluted with EtOAc (50 mL) and washed with 1M HCl (20 mL), then water (4×20 mL) and finally brine (20 mL). The organic layer was dried (MgSO$_4$) and then filtered through a silica plug eluting with EtOAc and concentrated to a black/brown semi-solid. The crude was triturated with DCM (5 mL) providing a dark brown powder (0.164 g, 85-90% pure). The powder was chromatographed on silica gel eluting with 30% EOAc:petroleum spirit. The solid obtained from concentration of appropriate fractions as a light brown solid that was recrystallized from iPrOH-petroleum spirit providing the title compound as an off-white solid (0.058 g, 10% yield). Mp 238-241° C. $^1$H NMR (400 MHz, DMSO) δ 10.75 (s, 1H), 9.28 (s, 1H), 7.97 (d, J=8.7 Hz, 2H), 7.61 (d, J=8.7 Hz, 2H), 7.42 (d, J=8.9 Hz, 2H), 6.79 (d, J=8.9 Hz, 2H). $^{13}$C NMR (101 MHz, DMSO) δ 168.6, 166.6, 153.5, 135.8, 129.5, 129.2, 128.6, 126.1, 120.1, 115.6. LCMS $R_f$ (min)=5.80. MS m/z 288.0 (M+H). HR-ESI calcd for $C_{14}H_{11}ClN_3O_2^+$ (M+H) 288.0534, found 288.0531.

5. 4-(4-Chlorophenyl)-N-(4-hydroxyphenyl)thiazole-2-carboxamide (E-5)

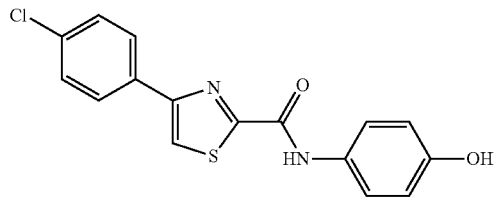 [SMILES: O=C(Nc1ccc(O)cc1)c1nc(-c2ccc(Cl)cc2)cs1]

Formamide (7.75 g, 172 mmol) in 250 mL of dry THF was cooled to in an ice-bath and $P_4S_{10}$ (13.2 g, 30 mmol) was added at once with vigorous stirring. After the addition the ice-bath was removed and the reaction was stirred at 30° C. for 3 h. The mixture was cooled to rt and then filtered directly into a 500 mL rb containing 2-Bromo-1-(4-chlorophenyl)ethan-1-one (3.76 g, 16.2 mmol) in THF (10 mL). The mixture was heated to 40-50° C. for 3 h. The mixture was then refluxed for 5 h and then left to stand at rt overnight. The THF was removed under vacuum and the residue taken up in EtOAc (200 mL) and vigorously stirred with saturated bicarbonate (100 mL) diluted with water (50 mL) for 10 min. The aqueous layer was separated and the organic layer was washed with water (3×200 mL) and finally with brine (20 mL). The organic layer was dried (MgSO4), filtered and then concentrated to a light yellow oil (5.48 g). The crude was then filtered through a silica plug eluting with DCM providing a solid upon concentration (3.6 g). The solid was recrystallized from petroleum spirit providing 4-(4-chlorophenyl)thiazole as white needles (2.36 g, 74% yield). $^1$H NMR (400 MHz, CDCl$_3$) δ 8.88 (d, J=2.0 Hz, 1H), 7.87 (d, J=8.7 Hz, 2H), 7.53 (d, J=2.0 Hz, 1H), 7.41 (d, J=8.8 Hz, 2H). A portion of 4-(4-chlorophenyl)thiazole was dissolved in dry THF (20 mL) in a N$_2$ atmosphere and was cooled to −78° C. with an iPrOH/CO$_2$(s) bath. Then nBuLi (2M, 0.511 mL, 1.022 mmol) was added dropwise to the mixture. After the addition the mixture was allowed to stir at −78° C. for 20 minutes. Then CO$_2$(g) was bubbled into the mixture for 15 minutes and stirred a further 15 minutes thereafter at −78° C. The iPrOH/CO$_2$(s) bath was removed and allowed to stir for 1.5 h. The mixture was quenched with saturated NH$_4$Cl solution (10 mL) and then diluted with EtOAc (25 mL). To this stirred solution was added 6M HCl (1 mL). The aqueous layer was discarded and the organic layer was washed with water (2×50 mL) and finally brine (10 mL). The organic layer was dried (MgSO$_4$), filtered and concentrated to a solid (0.219 g). The solid is partitioned between 1M NaOH (15 mL) and ether (50 mL). The organic layer is discarded and the aqueous layer washed with ether (50 mL). The aqueous layer was chilled on ice and then acidified with 6M HCl to pH 1-2. The resultant precipitate was collected on a Buchner funnel/flask and washed with water and then vacuum desiccated over KOH providing 0.150 g of 4-(4-chlorophenyl) thiazole-2-carboxylic acid that was contaminated with 4-(4-chlorophenyl)thiazole-2,5-dicarboxylic acid. This crude material was used without purification in the next step.

50 mg of the crude acid (0.209 mmol) was dissolved in DMF (2 mL) and HBTU (0.119 g, 0.313 mmol) was added, followed by p-anisidine (0.077 g, 0.626 mmol). To this stirred solution was added triethylamine (0.116 mL, 0.834 mmol) and then left to stir overnight. The mixture was slowly diluted with water and a precipitate resulted. The precipitate was collected on a Buchner funnel/flask and washed with water and suction dried (0.076 g). The solid was recrystallised from EtOH (0.048 g, 67%). The amidated product was taken up in $CH_2Cl_2$ (5 mL) in an $N_2$ atmosphere cooled in an ice bath and neat $BBr_3$ (0.04 mL, 0.418 mmol) and stirred with ice cooling for 2 h. Then a further aliquot of $BBr_3$ (0.04 mL, 0.418 mmol) was added dropwise and the ice bath removed and stirred a further 2 h. The mixture was diluted with EtOAc (20 mL) and slowly quenched with saturated $NH_4Cl$ solution (10 mL). The aqueous layer was removed and the organic layer washed with brine (10 mL). The organic layer was dried ($MgSO_4$), filtered and concentrated to a solid that was chromatographed on silica gel column eluting with 10% v/v EtOAc/petroleum spirit to and triturated in DCM to provide the title compound as a white solid (0.017 g, 37%). Mp 178-180° C. $^1$H NMR (400 MHz, DMSO) δ 10.43 (s, 1H), 9.37 (s, 1H), 8.51 (s, 1H), 8.19 (d, J=8.6 Hz, 2H), 7.61 (d, J=8.9 Hz, 2H), 7.57 (d, J=8.6 Hz, 2H), 6.78 (d, J=8.9 Hz, 2H). $^{13}$C NMR (101 MHz, DMSO) δ 164.0, 157.1, 154.4, 154.0, 133.2, 132.3, 129.2, 128.8, 128.2, 122.7, 120.5, 115.1. LCMS $R_f$ (min)=5.93. MS m/z 331.0 (M+H). HR-ESI calcd for $C_{16}H_{12}ClN_2O_2S^+$ (M+H) 331.0303, found 331.0301.

6. 2-(4-Chlorophenyl)-N-(4-hydroxyphenyl)thiazole-4-carboxamide (E-6)

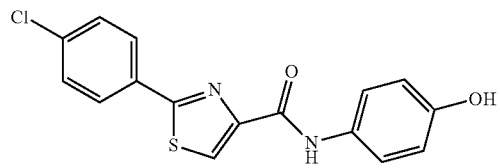 [SMILES: O=C(Nc1ccc(O)cc1)c1csc(-c2ccc(Cl)cc2)n1]

Ethyl 2-bromothiazole-4-carboxylate (Kelly, T. R.; Lang, F. *J. Org. Chem.* 1996, 3263, 4623-4633) (0.1 g, 0.424 mmol) was taken up in DMF (2.5 mL) containing $K_3PO_4.H_2O$ (0.293 g, 1.271 mmol) and (4-chlorophenyl)boronic acid (0.132 g, 0.847 mmol) and was degassed by bubbling $N_2$ through the stirred solution for 10 min. Then $Pd[PPh_3]_2Cl_2$ (0.014 g, 0.0212 mmol, 5 mol %) was added to the mixture and then heated to 110° C. for 5 h in an $N_2$ atmosphere. The mixture was cooled to rt and diluted with EtOAc (50 mL) and washed with 0.5M HCl (10 mL), then water (3×20 mL) and finally brine (10 mL). The organic layer was dried ($MgSO_4$), filtered and concentrated to a solid that was taken up in DCM (10 mL) and filtered through a silica plug eluting with DCM (50 mL) and concentrated to a residue (0.102 g). This reaction was repeated on an identical scale but the crude material obtained upon work-up was not filtered through a silica plug providing a further 0.22 g of crude (total of 0.302 g). The crude Suzuki product (0.302 g) was taken up in MeOH (20 mL) and water (5 mL) and to this mixture was added NaOH (≈0.2 g, 1 pellet) and stirred at rt overnight. The mixture was concentrated and then partitioned between water (100 mL) and ether (100 mL). The ether layer was discarded and the aqueous layer was washed with ether (2×50 mL) and then finally with EtOAc (50 mL). The aqueous layer was acidified with 6M HCl to pH≈2 and extracted with EtOAc (2×50 mL). The combined EtOAc layers were washed with water (20 mL) and finally with brine (10 mL). The organic layer was dried ($MgSO_4$), filtered and concentrated to a solid (0.159 g) that was contaminated with (4-chlorophenyl)boronic acid. The crude material (0.159 g) was dissolved in DMF (2 mL) was added HBTU (0.377 g, 0.995 mmol), p-anisidine (0.245 g, 1.99 mmol) and finally $Et_3N$ (368 μL, 2.654 mmol). The mixture was stirred at rt overnight and then the mixture was partitioned between EtOAc (30 mL) and water (60 mL). The aqueous was removed and the organic layer was washed with dilute HCl (20 mL), saturated bicarbonate (30 mL), water (20 mL) and finally brine (20 mL). The organic layer was dried ($MgSO_4$), filtered and concentrated to a dark brown residue (0.187 g). The crude material was chromatographed on silica gel eluting with 10-20% EtOAc:petroleum ether. The appropriate fractions were polled and concentrated to a solid (0.088 g, 30% yield from 0.848 mmol of ethyl 2-bromothiazole-4-carboxylate). $^1$H NMR (400 MHz, $CDCl_3$) δ 9.14 (s, 1H), 8.19 (s, 1H), 7.94 (d, J=8.7 Hz, 2H), 7.65 (d, J=9.0 Hz, 2H), 7.47 (d, J=8.8 Hz, 2H), 6.93 (d, J=9.0 Hz, 2H), 3.83 (s, 3H). The above material (0.088 g, 0.255 mmol) was dissolved in DCM (8 mL) and cooled in an ice-bath in an $N_2$ atmosphere and neat $BBr_3$ (121 μL, 1.276 mmol) was added to the mixture while stirring on an ice-bath for 3 h. The mixture was partitioned between EtOAc (20 mL) and saturated bicarbonate (10 mL). The aqueous was removed and the organic layer was washed with saturated bicarbonate (10 mL), water (10 mL) and finally with brine (10 mL). The organic layer was dried ($MgSO_4$), filtered and concentrated to a yellow solid that was recrystallized from EtOH providing the title compound as an off-white solid (0.028 g, 33% yield). Mp 217-220° C. $^1$H NMR (400 MHz, DMSO) δ 10.06 (s, 1H), 9.30 (s, 1H), 8.43 (s, 1H), 8.18 (d, J=8.7 Hz, 2H), 7.63 (d, J=8.7 Hz, 2H), 7.60 (d, J=8.9 Hz, 2H), 6.76 (d, J=8.9 Hz, 2H). $^{13}$C NMR (101 MHz, DMSO) δ 165.8, 158.5, 154.0, 150.8, 135.4, 131.3, 129.8, 129.3, 128.4, 125.1, 122.4, 115.0. LCMS $R_f$ (min)=6.06. MS m/z 331.0 (M+H). HR-ESI calcd for $C_{16}H_{12}ClN_2O_2S^+$ (M+H) 331.0303, found 331.0300.

7. N-((5-(4-Chlorophenyl)-1,3,4-oxadiazol-2-yl)methyl)-4-hydroxybenzenaminium chloride (E-7)

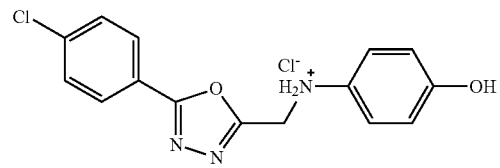 [SMILES: Oc1ccc([NH2+]Cc2nnc(-c3ccc(Cl)cc3)o2)cc1 ; [Cl-]]

2-(Chloromethyl)-5-(4-chlorophenyl)-1,3,4-oxadiazole (0.1 g, 0.437 mmol) was dissolved in DMSO (440 μL) and to the mixture was added p-anisidine (0.062 g, 0.5 mmol) followed by $K_2CO_3$ (0.175 g, 1.264 mmol) and stirred at rt overnight. The mixture was diluted with EtOAc (20 mL) and washed with water (4×30 mL) and then brine (10 mL). The organic layer was dried ($MgSO_4$), filtered and concentrated to a brown/amber resin (0.139 g). The resin was chromatographed on silica gel eluting with 0-5% EtOAc:DCM providing the product as an off-white solid (0.057 g, 41% yield). $^1$H NMR (400 MHz, CDCl$_3$) δ 7.98 (d, J=8.8 Hz, 2H), 7.50 (d, J=8.8 Hz, 2H), 6.83 (d, J=9.1 Hz, 2H), 6.76 (d, J=9.1 Hz, 2H), 4.63 (s, 2H), 4.09 (s, 1H), 3.77 (s, 3H). The methyl ether above (0.057 g, 0.181 mmol) was dissolved in DCM (5 mL) and cooled in an ice-bath in an N$_2$ atmosphere and neat BBr$_3$ (85 μL, 0.903 mmol) was added dropwise and stirred ice-cold for 3 h. The mixture was partitioned between EtOAc (20 mL) and saturated bicarbonate (10 mL). The aqueous was removed and the organic layer was washed with saturated bicarbonate (10 mL), water (10 mL) and finally with brine (10 mL). The organic layer was dried (MgSO$_4$), filtered and concentrated solid that was taken up in EtOAc (10 mL) and 4M HCl in dioxane (300 μL) providing a precipitate that was filtered and washed with EtOAc providing the title compound as a white solid (0.037 g, 61% yield). Mp 206° C. dec. $^1$H NMR (400 MHz, DMSO) δ 7.97 (d, J=8.7 Hz, 2H), 7.69 (d, J=8.7 Hz, 2H), 6.77 (d, J=8.7 Hz, 2H), 6.63 (d, J=8.8 Hz, 2H), 4.63 (s, 2H). $^{13}$C NMR (101 MHz, DMSO) δ 163.8, 162.8, 153.7, 137.0, 129.76, 128.4, 124.4, 124.1, 121.9, 119.4, 115.9, 41.4. LCMS R$_f$(min)=5.84. MS m/z 302.1 (M+H). HR-ESI calcd for C$_{15}$H$_{13}$ClN$_3$O$_2^+$ (M+H) 302.0691, found 302.0697.

8. 4-((5-(4-chlorophenyl)-1,3,4-oxadiazol-2-yl)amino)benzamide (E-8)

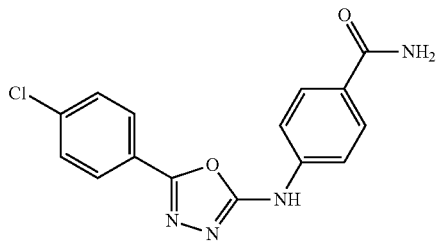

4-Chlorobenzohydrazide (0.532 g, 3.121 mmol) and 4-isothiocyanatobenzonitrile (0.5 g, 3.121 mmol) were combined in THF (15 mL) and stirred at rt overnight. To this mixture was added tosyl chloride (0.714 g, 3.748 mmol) was added followed by pyridine (530 μL, 6.554 mmol). The mixture was refluxed with stirring for 6 h and then stirred at rt overnight. The mixture was diluted with water (50 mL) and the resulting solid was filtered, washed consecutively with water (20 mL), EtOH (5 mL) and finally DCM (20 mL) providing the 4-((5-(4-Chlorophenyl)-1,3,4-oxadiazol-2-yl)amino)benzonitrile as a pale yellow solid (0.45 g, 49% yield). Mp 274-276° C. $^1$H NMR (400 MHz, DMSO) δ 11.34 (s, 1H), 7.92 (d, J=8.8 Hz, 2H), 7.84 (d, J=9.0 Hz, 2H), 7.77 (d, J=9.0 Hz, 2H), 7.67 (d, J=8.8 Hz, 2H).

4-((5-(4-Chlorophenyl)-1,3,4-oxadiazol-2-yl)amino)benzonitrile (0.05 g, 0.169 mmol) was dissolved in conc. H$_2$SO$_4$ (≈2 mL) at rt for 18 h. The mixture was chilled in an ice bath and crushed ice (50 g) was added to the stirred solution providing a solid. The mixture was neutralized with saturated bicarbonate and the solid was filtered and washed with plenty of water providing the title compound as a white solid (0.05 g, 94% yield). Mp>300° C. $^1$H NMR (400 MHz, DMSO) δ 11.03 (s, 1H), 7.94-7.88 (m, 4H), 7.86 (s, 1H), 7.70-7.62 (m, 4H), 7.23 (s, 1H). $^{13}$C NMR (101 MHz, DMSO) δ 167.4, 159.7, 157.3, 141.1, 135.7, 129.5, 128.8, 127.6, 127.4, 122.6, 116.3. HR-ESI calcd for C$_{15}$H$_{12}$ClN$_4$O$_2^+$ (M+H) 315.0643, found 315.0643.

9. (Z)-4-((5-(4-Chlorophenyl)-1,3,4-oxadiazol-2-yl)amino)-N'-hydroxybenzimidamide (E-9)

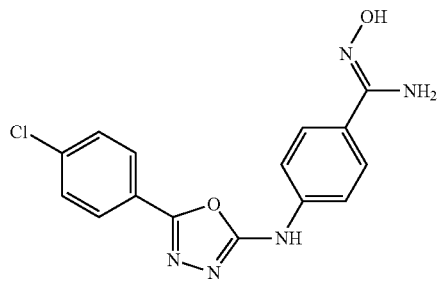 [SMILES: N/C(=N\O)c1ccc(Nc2nnc(-c3ccc(Cl)cc3)o2)cc1]

4-Chlorobenzohydrazide (0.532 g, 3.121 mmol) and 4-isothiocyanatobenzonitrile (0.5 g, 3.121 mmol) were combined in THF (15 mL) and stirred at rt overnight. To this mixture was added tosyl chloride (0.714 g, 3.748 mmol) was added followed by pyridine (530 μL, 6.554 mmol). The mixture was refluxed with stirring for 6 h and then stirred at rt overnight. The mixture was diluted with water (50 mL) and the resulting solid was filtered, washed consecutively with water (20 mL), EtOH (5 mL) and finally DCM (20 mL) providing the 4-((5-(4-Chlorophenyl)-1,3,4-oxadiazol-2-yl)amino)benzonitrile as a pale yellow solid (0.45 g, 49% yield). Mp 274-276° C. $^1$H NMR (400 MHz, DMSO) δ 11.34 (s, 1H), 7.92 (d, J=8.8 Hz, 2H), 7.84 (d, J=9.0 Hz, 2H), 7.77 (d, J=9.0 Hz, 2H), 7.67 (d, J=8.8 Hz, 2H).

4-((5-(4-Chlorophenyl)-1,3,4-oxadiazol-2-yl)amino)benzonitrile (0.15 g, 0.506 mmol) was added to a solution of hydroxylamine hydrochloride (0.039 g, 0.556 mmol), NaHCO$_3$ (0.047 g, 0.556 mmol) in EtOH (5 mL) and water (1 mL). The mixture was refluxed for 18 h, then cooled to rt and a lemon colored precipitate was filtered washed with EtOH and water (0.132 g). The solid was recrystallized from EtOH providing the title compound as a white solid (0.12 g, 66% yield). Mp>300° C. $^1$H NMR (400 MHz, DMSO) δ 10.85 (s, 1H), 9.51 (s, 1H), 7.91 (d, J=8.8 Hz, 2H), 7.68 (d, J=6.5 Hz, 2H), 7.66 (d, J=6.3 Hz, 2H), 7.60 (d, J=8.9 Hz, 2H), 5.75 (s, 2H). $^{13}$C NMR (101 MHz, DMSO) δ 159.9, 157.1, 150.5, 139.0, 135.6, 129.5, 127.4, 127.0, 126.3, 122.7, 116.6. LCMS R$_f$(min)=4.71. MS m/z 330.1 (M+H). HR-ESI calcd for C$_{15}$H$_{13}$ClN$_5$O$_2^+$ (M+H) 330.0752, found 330.0754.

10. 5-(4-Chlorophenyl)-N-(4-(5-methyl-1,2,4-oxadiazol-3-yl)phenyl)-1,3,4-oxadiazol-2-amine (E-10)

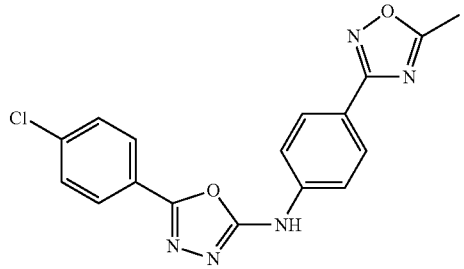 [SMILES: Cc1nc(-c2ccc(Nc3nnc(-c4ccc(Cl)cc4)o3)cc2)no1]

(Z)-4-((5-(4-Chlorophenyl)-1,3,4-oxadiazol-2-yl)amino)-N'-hydroxybenzimidamide E-9 (0.05 g, 0.152 mmol) in AcOH (2 mL) was added acetic anhydride (15.8 µL, 0.167 mmol) and stirred at rt for 0.5 h, then heated to 70° C. overnight. The cooled solution was diluted with water (5 mL) providing a precipitate which was collected and washed with bicarbonate then water giving a grey/green solid (0.033 g). The solid was recrystallized from AcOH providing the title compound (0.014 g, 26% yield). Mp>300° C. $^1$H NMR (400 MHz, DMSO) δ 11.14 (s, 1H), 8.01 (d, J=8.9 Hz, 2H), 7.92 (d, J=8.7 Hz, 2H), 7.78 (d, J=8.9 Hz, 2H), 7.67 (d, J=8.7 Hz, 2H), 2.65 (s, 3H). $^{13}$C NMR (101 MHz, DMSO) δ 177.2, 167.3, 159.7, 157.4, 141.2, 135.8, 129.6, 128.2, 127.5, 122.6, 119.6, 117.4, 12.0. LCMS R$_f$ (min)=5.89. MS m/z 354.1 (M+H). HR-ESI calcd for $C_{17}H_{13}ClN_5O_2^+$ (M+H) 354.0752, found 354.0751. 11.5-(4-Chlorophenyl)-N-(4-hydroxyphenyl)-1,3,4-oxadiazole-2-carboxamide (E-11)

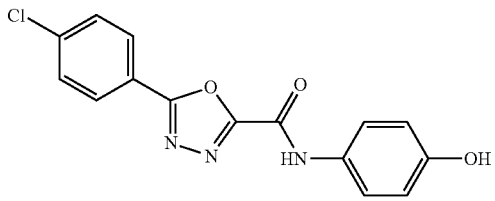 [SMILES: O=C(Nc1ccc(O)cc1)c1nnc(-c2ccc(Cl)cc2)o1]

Ethyl 5-(4-chlorophenyl)-1,3,4-oxadiazole-2-carboxylate (Bartroli, J. et al. *J. Med. Chem.* 1998, 41, 1855-68 (1 g, 3.958 mmol) was dissolved in THF (20 mL) and MeOH (39 mL) and cooled in an ice bath. To the mixture was added LiOH.H$_2$O (0.332 g, 7.916 mmol) in water (4 mL) and the mixture was stirred overnight. The mixture was concentrated to a solid and triturated with 20% EtOAc:petroleum ether. The solid was collected and washed with ether providing lithium 5-(4-chlorophenyl)-1,3,4-oxadiazole-2-carboxylate as an off-white solid (0.852 g, 93% yield). $^1$H NMR (400 MHz, D$_2$O) δ 7.93 (dd, J=8.4, 1.2 Hz, 1H), 7.55 (dd, J=8.5, 1.1 Hz, 1H). The lithium salt (0.15 g, 6.507 mmol) was added to DMF (5 mL), followed by 4-aminophenol (0.092 g<0.846 mmol), HATU (0.371 g, 0.976 mmol) and finally Et$_3$N (272 µL, 1.952 mmol). The mixture was left to stir overnight at rt, then diluted with water until a precipitate formed. The solid was recrystallised from EtOH providing the title compound as an off-white solid (0.048 g, 23% yield). Mp 259° C. dec. $^1$H NMR (400 MHz, DMSO) δ 11.02 (s, 1H), 9.46 (s, 1H), 8.13 (d, J=8.8 Hz, 2H), 7.74 (d, J=8.8 Hz, 2H), 7.59 (d, J=9.0 Hz, 2H), 6.78 (d, J=9.0 Hz, 2H). $^{13}$C NMR (101 MHz, DMSO) δ 164.4, 158.8, 154.7, 150.9, 137.5, 129.8, 129.0, 129.0, 122.6, 121.8, 115.2. LCMS R$_f$(min)=6.03. MS m/z 316.0 (M+H). HR-ESI calcd for $C_{15}H_{11}ClN_3O_3^+$ (M+H) 316.0483, found 316.0482.

12. (2S,3S)-2-((4-(5-(4-chlorophenyl)-1,3,4-oxadiazol-2-yl)phenyl)carbamoyl)-3-hydroxypyrrolidin-1-ium chloride (E-12)

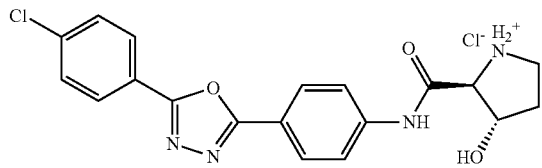

(2S,3S)-1-(tert-Butoxycarbonyl)-3-hydroxypyrrolidine-2-carboxylic acid (0.0765 g, 0.331 mmol) was placed in a dry three neck flask in an N$_2$ atmosphere and dissolved in anhydrous THF (3.3 mL). The flask was cooled in an ice-salt bath (≈−15° C.) and N-methylmorpholine (40.2 µL, 0.365 mmol) was added in one portion followed by isobutylchloroformate (47.1 µL, 0.365 mmol) dropwise and allowed to stir for 20 min (the ice-salt bath was not recharged during this period and warmed to −10° C. at 20 min). Then LA-3-126 (0.09 g, 0.331 mmol) was added in one portion and left to stir overnight without recharging the cooling bath. The solution was diluted with EtOAc (50 mL) and washed with water (20 mL) and then with brine. The organic layer was dried (MgSO$_4$), filtered and concentrated to a yellow semi-solid (0.233 g). The semi-solid was triturated with a minimum of ice-cold EtOAc filtered and the filter cake washed with ice-cold EtOAc providing the intermediate Boc protected product as a white solid (0.07 g, 43% yield, can be recrystallized from EtOAc). Mp 218° C. dec. $^1$H NMR (400 MHz, CDCl$_3$) δ 9.86 (s, 1H), 8.16-7.97 (m, 4H), 7.69 (d, J=8.5 Hz, 2H), 7.51 (d, J=8.6 Hz, 2H), 5.00-4.82 (m, 1H), 4.50-4.35 (m, 1H), 3.75-3.46 (m, 2H), 2.26-1.96 (m, 2H), 1.52 (s, 9H), 1.25 (s, 1H). HR-ESI calcd for $C_{24}H_{26}ClN_4O_5^+$ (M+H) 485.1586, found 485.1585.

A portion of the Boc derivative (0.05 g, 0.103 mmol) was dissolved in anhydrous dioxane (2 mL) in an N$_2$ atmosphere and 4M HCl in dioxane (2 mL) was added to the mixture and stirred at rt for 3 h. The mixture was concentrated to a solid that was triturated with EtOAc and filtered, providing the title compound as an off-white solid (0.041 g, 94% yield). Mp 280° C. dec. $^1$H NMR (400 MHz, DMSO) δ 11.40 (s, 1H), 9.96 (s, 1H), 8.79 (s, 1H), 8.22-8.05 (m, 4H), 7.91 (d, J=8.9 Hz, 2H), 7.72 (d, J=8.7 Hz, 2H), 5.99 (d, J=3.3 Hz, 1H), 4.62-4.46 (m, 1H), 4.34 (d, J=1.4 Hz, 1H), 3.49-3.39 (m, 2H), 2.17-1.83 (m, 2H). $^{13}$C NMR (101 MHz, DMSO) δ 165.8, 163.9, 163.1, 141.5, 136.7, 129.6, 128.4, 127.8, 122.3, 119.9, 118.6, 73.9, 67.4, 44.5, 32.3. LCMS R$_f$(min)= 4.69. MS m/z 385.2 (M+H). HR-ESI calcd for $C_{19}H_{18}ClN_4O_3^+$ (M+H) 385.1062, found 385.1063.

13. 2-(4-(2H-tetrazol-5-yl)phenyl)-5-(4-chlorophenyl)-1,3,4-oxadiazole (E-13)

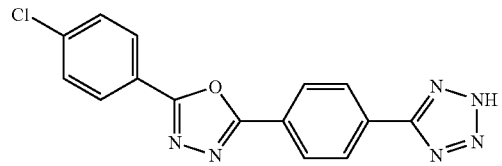 [SMILES: Clc1ccc(-c2nnc(-c3ccc(-c4nn[nH]n4)cc3)o2)cc1]

Ethyl 5-(4-chlorophenyl)-1,3,4-oxadiazole-2-carboxylate (Bartroli, J. et al. *Med. Chem.* 1998, 41, 1855-68 (2.13 g, 8.431 mmol) was dissolved in THF (42 mL) and MeOH (84 mL) and cooled in an ice bath. To the mixture was added LiOH.H$_2$O (1.77 g, 42.153 mmol) in water (8.4 mL) and the mixture was stirred for 3-4 h without recharging the ice-bath. The mixture was concentrated to a solid and dissolved in water (100 mL). The solution was filtered through celite and then acidified to pH≈1-2 precipitating 2-(4-chlorophenyl)-1,3,4-oxadiazole as a white solid that was collected and washed with water (1.14 g, 75% yield). Mp 127-131° C. $^1$H NMR (400 MHz, CDCl$_3$) δ 8.47 (s, 1H), 8.03 (d, J=8.8 Hz, 2H), 7.51 (d, J=8.8 Hz, 2H).

A portion of the oxadiazole (0.595 g, 3.293 mmol) was taken up in DMSO (6.6 mL) and to this solution was added consecutively CuI (0.06 g, 0.659 mmol, 20 mol %), 1,10-phenanthroline (0.238 g, 1.318 mmol, 40 mol %), Cs$_2$CO$_3$ (1.07 g, 3.293 mmol) and finally 4-iodobenzonitrile (1.51 g, 6.589 mmol). The mixture was heated at 100° C. for 4 h, and then cooled to rt. The resulting mixture was diluted with water (30 mL) and extracted with EtOAc (2×30 mL), and the combined organic layers were dried (MgSO$_4$), filtered and concentrated to a semi-solid (2.82 g). The semi-solid was chromatographed on silica gel eluting 20% EtOAc:petroleum ether, providing 4-(5-(4-chlorophenyl)-1,3,4-oxadiazol-2-yl)benzonitrile as a solid that was recrystallized from EtOH (0.603 g, 65% yield). Mp 247-249° C. $^1$H NMR (400 MHz, CDCl$_3$) δ 8.26 (d, J=8.7 Hz, 1H), 8.10 (d, J=8.8 Hz, 1H), 7.85 (d, J=8.7 Hz, 1H), 7.55 (d, J=8.8 Hz, 1H).

A portion of nitrile (0.3 g, 1.065 mmol) was dissolved in a DMF (1.5 mL) and to this mixture was added NaN$_3$ (0.083 g, 1.278 mmol) and NH$_4$Cl (0.068 g, 1.278 mmol). The mixture was heated to 100° C. for 18 h. The cooled solution was diluted with water (10 mL) and acidified with 6M HCl (1 mL) providing a precipitate that was collected and washed with water. The solid was then suspended in 2.5M NaOH (10 mL) and stirred for 0.5 h at rt. The solution was filtered and the filter cake was washed with 0.25M NaOH (5 mL). The combined filtrate was acidified with 6M HCl and the precipitate was collected and washed with water. The solid was triturated with boiling EtOH (10 mL) collected on the funnel and washed with EtOH and finally ether, providing the title compound as a white solid (0.273 g, 79% yield). Mp 270° C. dec. $^1$H NMR (400 MHz, DMSO) δ 8.38 (d, J=8.5 Hz, 1H), 8.29 (d, J=8.6 Hz, 1H), 8.19 (d, J=8.6 Hz, 1H), 7.74 (d, J=8.6 Hz, 1H). $^{13}$C NMR (101 MHz, DMSO) δ 163.6, 163.5, 155.3, 136.9, 129.6, 128.5, 127.8, 127.6, 127.4, 125.3, 122.1. LCMS R$_f$(min)=5.80. MS m/z 325.0 (M+H). HR-ESI calcd for C$_{15}$H$_{10}$ClN$_6$O$^+$ (M+H) 325.0599, found 325.0598.

14. (Z)-4-(5-(4-Chlorophenyl)-1,3,4-oxadiazol-2-yl)-N'-hydroxybenzimidamide (E-14)

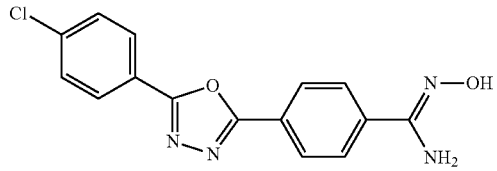 [SMILES: N/C(=N\O)c1ccc(-c2nnc(-c3ccc(Cl)cc3)o2)cc1]

4-(5-(4-Chlorophenyl)-1,3,4-oxadiazol-2-yl)benzonitrile (0.37 g, 1.314 mmol) was added to a solution of hydroxylamine hydrochloride (0.274 g, 3.941 mmol), Et$_3$N (546 µL, 3.941 mmol) in EtOH (13 mL). The mixture was refluxed for 16 h, then cooled to rt and the precipitate was filtered washed with water, EtOH and finally ether (0.38 g). The solid was recrystallized from EtOH providing the title compound as a white solid (0.215 g, 52% yield). Mp 239-241° C. $^1$H NMR (400 MHz, DMSO) δ 9.93 (s, 1H), 8.17 (d, J=8.7 Hz, 2H), 8.14 (d, J=8.7 Hz, 2H), 7.93 (d, J=8.7 Hz, 2H), 7.73 (d, J=8.7 Hz, 2H), 5.99 (s, 2H). $^{13}$C NMR (101 MHz, DMSO) δ 164.0, 163.3, 150.0, 136.8, 136.6, 129.6, 128.5, 126.6, 126.1, 123.3, 122.2. LCMS R$_f$(min)=4.41. MS m/z 315.1 (M+H). HR-ESI calcd for C$_{15}$H$_{12}$ClN$_4$O$_2^+$ (M+H) 315.0643, found 315.0640.

15. 3-(4-(5-(4-Chlorophenyl)-1,3,4-oxadiazol-2-yl)phenyl)-1,2,4-oxadiazol-5(4H)-one (E-15)

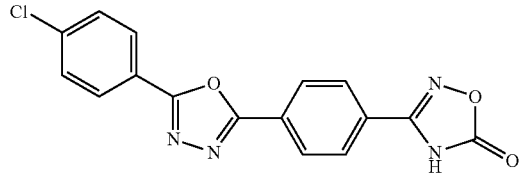 [SMILES: O=c1[nH]c(-c2ccc(-c3nnc(-c4ccc(Cl)cc4)o3)cc2)no1]

(Z)-4-(5-(4-Chlorophenyl)-1,3,4-oxadiazol-2-yl)-N'-hydroxybenzimidamide (0.26 g, 0.826 mmol) was suspended in THF (10 mL). To this mixture was added CDI (0.201 g, 1.239 mmol) and the mixture was refluxed for 16 h with stirring. The cooled solution was diluted with water (≈80 mL) and NaOH (0.2 g) was added to the mixture and stirred for 1 h. The mixture was filtered and the filtrate was acidified with 6M HCl to pH≈2. The precipitate was filtered and washed with water and finally with ether providing the title compound as a white solid that can be recrystallized from DMSO (0.23 g, 82% yield).). Mp>300° C. $^1$H NMR (400 MHz, DMSO) δ 13.19 (s, 1H), 8.35 (d, J=8.7 Hz, 2H), 8.19 (d, J=8.7 Hz, 2H), 8.06 (d, J=8.7 Hz, 2H), 7.74 (d, J=8.7 Hz, 2H). $^{13}$C NMR (101 MHz, DMSO) δ 163.7, 163.4, 160.1, 156.9, 137.0, 129.6, 128.6, 127.5, 127.0, 126.4, 126.2, 122.1. LCMS R$_f$(min)=5.74. MS m/z 341.1 (M+H). HR-ESI calcd for C$_{16}$H$_{10}$ClN$_4$O$_3^+$ (M+H) 341.0436, found 341.0436.

16. 3-(4-((5-(4-Chlorophenyl)-1,3,4-oxadiazol-2-yl)amino)phenyl)-1,2,4-oxadiazol-5(4H)-one (E-16)

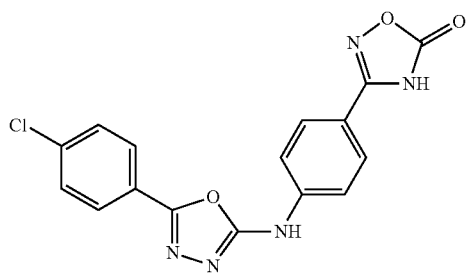 [SMILES: O=c1[nH]c(-c2ccc(Nc3nnc(-c4ccc(Cl)cc4)o3)cc2)no1]

(Z)-4-((5-(4-Chlorophenyl)-1,3,4-oxadiazol-2-yl)amino)-N'-hydroxybenzimidamide E-9 (0.3 g, 0.91 mmol) was dissolved in a mixture of DMF (5 mL) and THF (11 mL). To this mixture was added CDI (0.221 g, 1.365 mmol) and refluxed overnight. The mixture was cooled and concentrated to a semi-solid that was diluted with water (25 mL) and NaOH (≈0.2 g) was added and the mixture was stirred until all solids dissolved. The aqueous layer was washed with EtOAc (30 mL) and the aqueous layer was filtered and then acidified with 6M HCl providing a gelatinous precipitate. The precipitate was filtered washed with water and then ether. The gelatinous material was boiled in EtOH (50 mL) that provided the title compound upon cooling as a white powder. The powder was collected on the funnel and washed with EtOH and finally ether (0.226 g, 70% yield). Mp>300° C. $^1$H NMR (400 MHz, DMSO) δ 12.88 (s, 1H), 11.22 (s, 1H), 7.92 (d, J=8.7 Hz, 2H), 7.83 (d, J=9.0 Hz, 2H), 7.78 (d, J=9.0 Hz, 2H), 7.67 (d, J=8.7 Hz, 2H). $^{13}$C NMR (101 MHz, DMSO) δ 160.0, 159.5, 157.5, 157.0, 141.8, 135.8, 129.5, 127.4, 127.3, 122.5, 117.2, 116.3. LCMS $R_f$(min)=5.18. MS m/z 356.1 (M+H). HR-ESI calcd for $C_{16}H_{11}ClN_5O_3^+$ (M+H) 356.0545, found 356.0548.

17. Amino(4-(5-phenyl-1,3,4-oxadiazol-2-yl)phenyl)methaniminium chloride (E-17)

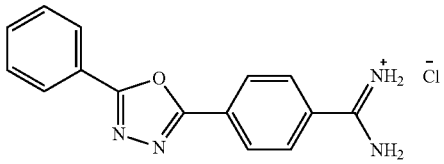

3-(4-(5-(4-Chlorophenyl)-1,3,4-oxadiazol-2-yl)phenyl)-1,2,4-oxadiazol-5(4H)-one E-15 (0.1 g, 0.294 mmol) was taken up in AcOH (18 mL) and water (2 mL) and to this mixture was added 10% Pd/C (0.1 g). The mixture was hydrogenated in a H₂(g) atmosphere at rt for ≈16 h, then filtered through celite and concentrated to a solid that was triturated with ether and collected on the funnel (0.083 g). The solid was taken up in dry dioxane (5 mL) and 4M HCl in dioxane (1 mL) was added to the mixture and stirred for 0.5 h. The mixture was concentrated to ≈1 mL and then diluted with EtOAc (15 mL) precipitating a solid that was filtered washed with EtOAc and finally ether providing the title compound as a light yellow solid (0.06 g, 68%). Mp 276-281° C. ¹H NMR (400 MHz, DMSO) δ 9.67 (s, 2H), 9.46 (s, 2H), 8.35 (d, J=8.4 Hz, 2H), 8.27-8.14 (m, 2H), 8.09 (d, J=8.4 Hz, 2H), 7.76-7.55 (m, 3H). ¹³C NMR (101 MHz, DMSO) δ 164.9, 164.6, 163.1, 132.3, 130.9, 129.5, 129.3, 127.7, 127.0, 126.9, 123.1. LCMS $R_f$(min)=3.99. MS m/z 265.2 (M+H). HR-ESI calcd for $C_{15}H_{13}N_4O^+$ (M+H) 265.1084, found 265.1080.

18. (2S,3S)-2-((4-(5-(4-chlorophenyl)-1,3,4-oxadiazol-2-yl)benzyl)carbamoyl)-3-hydroxypyrrolidin-1-ium chloride (E-18)

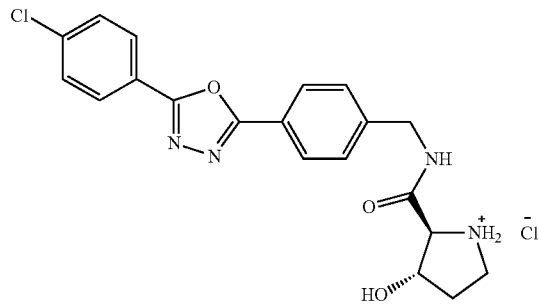 [SMILES: O=C(NCc1ccc(-c2nnc(-c3ccc(Cl)cc3)o2)cc1)[C@H]1[NH2+]CC[C@@H]1O ; [Cl-]]

(4-(5-(4-Chlorophenyl)-1,3,4-oxadiazol-2-yl)phenyl)methanaminium chloride (0.1 g, 0.3104 mmol), (2S,3S)-1-(tert-butoxycarbonyl)-3-hydroxypyrrolidine-2-carboxylic acid (0.072 g, 0.3104 mmol) and HOBt (0.05 g, 0.373 mmol) were stirred in DMF (3 mL) and DIPEA (53 µL, 0.3104 mmol) was added to the stirred mixture at rt. To the mixture was added EDC (0.065 g, 0.3414 mmol) and then stirred overnight at rt. The mixture was slowly diluted with water (≈20 mL) and stirred at rt for 2 h. The precipitate was collected and washed with water and suck dried providing the crude Boc protected product as an off-white powder (0.145 g). ¹H NMR (400 MHz, CDCl₃) δ 8.15-8.00 (m, 4H), 7.52 (d, J=8.8 Hz, 2H), 7.43 (d, J=8.3 Hz, 2H), 4.89-4.07 (m, 4H), 3.84-3.38 (m, 2H), 2.28-1.88 (m, 2H), 1.45 (s, 9H). A portion of the Boc compound (0.1 g, 0.201 mmol) was dissolved in 4M HCl in dioxane (3 mL) and stirred at rt for 3 h. The mixture was diluted with EtOAc (10 mL) and filtered. The solid was washed with EtOAc and finally ether providing the title compound as an off-white solid (0.082 g, 94% yield). Mp 294° C. dec. ¹H NMR (400 MHz, DMSO) δ 9.85 (s, 1H), 9.38 (t, J=5.9 Hz, 1H), 8.69 (s, 1H), 8.15 (d, J=8.7 Hz, 2H), 8.12 (d, J=8.4 Hz, 2H), 7.72 (d, J=8.7 Hz, 2H), 7.55 (d, J=8.4 Hz, 2H), 5.90 (d, J=3.7 Hz, 1H), 4.47 (d, J=5.9 Hz, 2H), 4.45-4.38 (m, 1H), 4.13 (s, 1H), 2.02-1.85 (m, 2H). ¹³C NMR (101 MHz, DMSO) δ 166.7, 164.1, 163.2, 142.9, 136.8, 129.6, 128.5, 128.2, 126.9, 122.3, 122.0, 73.8, 66.3, 44.1, 42.4, 32.3. LCMS $R_f$(min)=4.83. MS m/z 399.1 (M+H). HR-ESI calcd for $C_{20}H_{20}ClN_4O_3^+$ (M+H) 399.1218, found 399.1215.

19. Amino(4-(5-(4-chlorophenyl)-1,3,4-oxadiazol-2-yl)phenyl)methaniminium chloride (E-19)

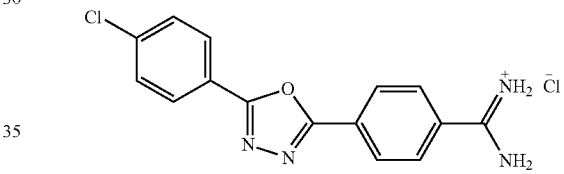

4-(5-(4-Chlorophenyl)-1,3,4-oxadiazol-2-yl)benzonitrile (0.12 g, 0.426 mmol) was suspended in THF (5 mL) and cooled in an ice-bath in an N₂ atmosphere and LiHMDS (1M in THF, 900 µL, 0.9 mmol) was added dropwise and left to stir in an ice-bath for 4 h and then at rt overnight for 12 h. The mixture was re-cooled in an ice-bath and 4M HCl in dioxane (852 µL, 3.408 mmol) and stirred in an ice-bath for 4 h and hen rt for 20 min. The precipitate was filtered and washed with EtOAc then ether providing a white solid (0.182 g). The solid was dissolved in MeOH (≈5 mL) and warmed to dissolve. The solution was filtered, diluted with water (≈10 mL) and 1M NaOH added dropwise until a precipitate results. The precipitate was collected, washed with water and finally ether (0.092 g). The solid was stirred in 4M HCl in dioxane (1 mL) and EtOAc (4 mL) and stirred overnight. The precipitate was filtered and washed with EtOAc and finally ether providing the title compound as an off-white solid (0.094 g, yield 66%). Mp>300° C. ¹H NMR (400 MHz, DMSO) δ 9.63 (s, 2H), 9.40 (s, 2H), 8.36 (d, J=8.7 Hz, 2H), 8.20 (d, J=8.8 Hz, 2H), 8.08 (d, J=8.7 Hz, 2H), 7.73 (d, J=8.8 Hz, 2H). ¹³C NMR (101 MHz, DMSO) δ 164.9, 163.9, 163.2, 137.1, 131.0, 129.6, 129.3, 128.7, 127.6, 127.0, 122.0. LCMS $R_f$(min)=4.23. MS m/z 299.1 (M+H). HR-ESI calcd for $C_{15}H_{12}ClN_4O^+$ (M+H) 299.0694, found 299.0695.

20. Amino(4-((5-phenyl-1,3,4-oxadiazol-2-yl)amino)phenyl)methaniminium chloride (E-20)

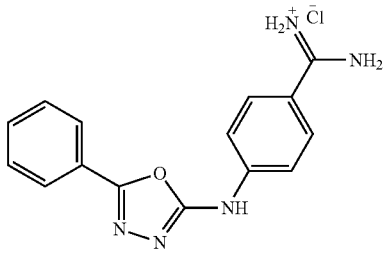 [SMILES: Cl ; N=C(N)c1ccc(Nc2nnc(-c3ccccc3)o2)cc1]

3-(4-((5-(4-Chlorophenyl)-1,3,4-oxadiazol-2-yl)amino)phenyl)-1,2,4-oxadiazol-5(4H)-one (0.104 g, 0.294 mmol) was suspended in AcOH (18 mL) and water (2 mL). To the mixture was added 10% Pd/C (0.1 g) and then hydrogenated in a H$_2$ atmosphere for 36 h. The mixture was filtered through celite and then concentrated to a residue that was stirred with 4M HCl in dioxane (3 mL) overnight. The precipitate was filtered and washed with EtOAc and finally ether providing the title compound as a white solid (0.038 g, 41% yield). Mp>300° C. $^1$H NMR (400 MHz, DMSO) δ 11.47 (s, 1H), 9.28 (s, 2H), 9.04 (s, 2H), 7.94-7.89 (m, 4H), 7.85-7.80 (m, 2H), 7.62-7.56 (m, 3H). $^{13}$C NMR (101 MHz, DMSO) δ 164.7, 159.4, 158.3, 143.6, 131.3, 129.6, 129.4, 125.7, 123.6, 120.3, 116.7. LCMS R$_f$ (min)=4.52. MS m/z 280.1 (M+H). HR-ESI calcd for C$_{15}$H$_{14}$N$_5$O$^+$ (M+H) 280.1193, found 280.1190.

21. (2S,3S)-2-((4-(5-(4-Chlorophenyl)-1,2,4-oxadiazol-3-yl)benzyl)carbamoyl)-3-hydroxypyrrolidin-1-ium chloride (E-21)

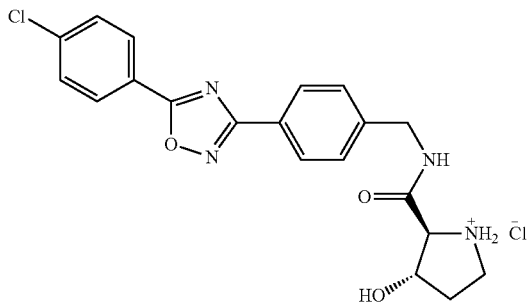 [SMILES: O=C(NCc1ccc(-c2noc(-c3ccc(Cl)cc3)n2)cc1)[C@H]1NCC[C@@H]1O ; Cl]

(Z)-4-(Azidomethyl)-N'-hydroxybenzimidamide (Weber, L. et al PCT Int. Appl., WO 2001014320 A1 20010301) (0.5 g, 2.615 mmol) was stirred in xylene (10 mL) and pyridine (1.5 mL) was added to the stirred solution. The resultant clear solution was treated with 4-chlorobenzoyl chloride (332 µL, 2.615 mmol) at rt. After the addition the mixture was refluxed for 2 h and then cooled to rt. The cooled mixture was diluted with EtOAc (100 mL) and washed with 1M HCl (30 mL), water (50 mL), saturated bicarbonate (50 mL) and finally brine (30 mL). The organic layer was dried (MgSO$_4$), filtered and then concentrated to a solid (0.8 g, 98% yield). $^1$H NMR (400 MHz, CDCl$_3$) δ 8.25-8.12 (m, 4H), 7.55 (d, J=8.8 Hz, 2H), 7.48 (d, J=8.5 Hz, 2H), 4.44 (s, 2H). A portion of the oxadiazole (0.2 g, 0.642 mmol) was suspended in MeOH (17 mL) and ammonium formate (0.303 g, 4.812 mmol) was added to the mixture followed by freshly activated zinc dust (0.315 g, 4.812 mmol) and stirred at rt for 3 h. The mixture was diluted with water (50 mL) and DCM (50 mL) and vigorously stirred. Then three pellets of NaOH (≈0.6 g) were added and vigorous stirring continued for a further 30 min. The mixture was then filtered through celite, the organic layer was separated, dried (MgSO$_4$), filtered and then concentrated to provide (4-(5-(4-chlorophenyl)-1,2,4-oxadiazol-3-yl)phenyl)methanamine as a solid (0.181 g, 98% yield). $^1$H NMR (400 MHz, CDCl$_3$) δ 8.17 (d, J=8.8 Hz, 2H), 8.13 (d, J=8.3 Hz, 2H), 7.54 (d, J=8.8 Hz, 2H), 7.47 (d, J=8.5 Hz, 2H), 3.97 (s, 2H), 1.55 (bs, 2H).

(4-(5-(4-chlorophenyl)-1,2,4-oxadiazol-3-yl)phenyl)methanamine (0.18 g, 0.629 mmol) was dissolved in DMF (5 mL) followed by (2S,3S)-1-(tert-butoxycarbonyl)-3-hydroxypyrrolidine-2-carboxylic acid (0.146 g, 0.629 mmol), HATU (0.359 g, 0.945 mmol) and finally DIPEA (429 µL, 2.519 mmol). The mixture was stirred overnight at rt and then diluted with water (100 mL) and extracted with (2×50 mL). The combined organics were washed with water (20 mL), 0.5M HCl (50 mL), saturated bicarbonate (30 mL) and finally brine (30 mL). The organic layer was dried (MgSO$_4$), filtered and then concentrated to provide Boc protected product as a solid (0.36 g). The solid was recrystallised from MeOH providing an off-white solid (0.16 g, 51% yield). $^1$H NMR (400 MHz, CDCl$_3$) δ 8.16 (d, J=8.8 Hz, 2H), 8.11 (d, J=8.1 Hz, 2H), 7.54 (d, J=8.7 Hz, 2H), 7.40 (d, J=8.3 Hz, 2H), 4.83-4.19 (m, 4H), 3.77-3.43 (m, 2H), 2.23-1.27 (m, 13H). A portion of the Boc derivative (0.11 g, 0.221 mmol) was dissolved in EtOAc (1 mL) and 4M HCl in dioxane was added to the stirring mixture a rt overnight. The resulting precipitate was filtered and washed with EtOAc and finally ether providing the title compound as an off-white solid (0.85 g, 89% yield). Mp 278° C. dec. $^1$H NMR (400 MHz, DMSO) δ 9.98 (bs, 1H), 9.41 (t, J=5.9 Hz, 1H), 8.68 (bs, 1H), 8.19 (d, J=8.8 Hz, 2H), 8.06 (d, J=8.4 Hz, 2H), 7.75 (d, J=8.8 Hz, 2H), 7.52 (d, J=8.4 Hz, 2H), 5.92 (bs, 1H), 4.55-4.34 (m, 3H), 4.14 (s, 1H), 3.40 (s, 2H), 2.03-1.85 (m, 2H). $^{13}$C NMR (101 MHz, DMSO) δ 174.6, 168.1, 166.6, 142.4, 138.2, 129.8, 129.7, 128.1, 127.2, 124.7, 122.2, 73.9, 66.3, 44.1, 42.4, 32.3. LCMS R$_f$ (min)=4.97. MS m/z 399.1 (M+H). HR-ESI calcd for C$_{20}$H$_{20}$ClN$_4$O$_3^+$ (M+H) 399.1218, found 399.1217.

22. (2S,3S)-2-((4-(3-(4-Chlorophenyl)-1,2,4-oxadiazol-5-yl)benzyl)carbamoyl)-3-hydroxypyrrolidin-1-ium chloride (E-22)

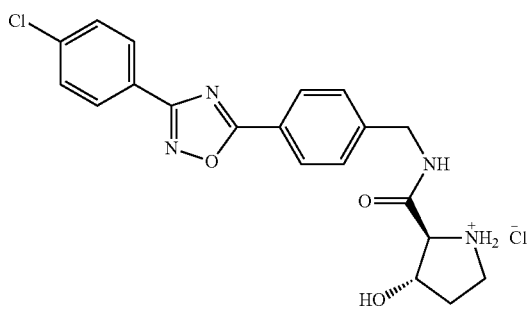 [SMILES: O=C(NCc1ccc(-c2nc(-c3ccc(Cl)cc3)no2)cc1)[C@H]1NCC[C@@H]1O ; Cl]

4-(((tert-Butoxycarbonyl) amino)methyl)benzoic acid (0.628 g, 2.5 mmol) was dissolved in dioxane (25 mL) and N-methylmorpholine (275 µL, 2.5 mmol) was added and then cooled with an ice-bath. Isobutylchloroformate was added dropwise and left to stir on ice for 5 min and then the ice-bath was removed and allowed to stir a further 5 min. (Z)-4-chloro-N'-hydroxybenzimidamide (0.427 g, 2.5 mmol) was added and stirred for 2 h at rt and then refluxed for 2 h. The cooled solution was concentrated to a solid and then taken up in EtOAc (150 mL) and washed consecutively with water (50 mL), saturated bicarbonate (50 mL), water (50 mL), 0.5M HCl (50 mL) and finally brine (30 mL). The organic layer was dried (MgSO$_4$), filtered and then concentrated to a solid (0.94 g). The solid was chromatographed on silica gel eluting with 20% EtOAc:petroleum ether providing the Boc protected product as a white solid (0.48 g, 50% yield). $^1$H NMR (400 MHz, CDCl$_3$) δ 8.18 (d, J=8.4 Hz, 2H), 8.12 (d, J=8.7 Hz, 2H), 7.51-7.44 (m, 4H), 5.06-4.88 (m, 1H), 4.42 (d, J=5.7 Hz, 2H), 1.48 (s, 9H). A portion of the oxadiazole (0.2 g, 0.518 mmol) was dissolved in EtOAc (2 mL) and 4M HCl in dioxane (2 mL) was added to the mixture and stirred at rt overnight. The resultant precipitate was filtered and washed with EtOAc and finally ether (0.12 g, yield 72%). $^1$H NMR (400 MHz, DMSO) δ 8.36 (bs, 3H), 8.26 (d, J=8.4 Hz, 2H), 8.11 (d, J=8.7 Hz, 2H), 7.76 (d, J=8.4 Hz, 2H), 7.70 (d, J=8.7 Hz, 2H), 4.18 (s, 2H).

A portion of the oxadiazole (0.1 g, 0.3104 mmol) was suspended in DMF (2.5 mL) and to this mixture was added HATU (0.177 g, 0.466 mmol), (2S,3S)-1-(tert-butoxycarbonyl)-3-hydroxypyrrolidine-2-carboxylic acid (0.072 g, 0.3104 mmol) and finally DIPEA (264 μL, 1.552 mmol) and stirred at rt overnight. The mixture was partitioned between EtOAc (50 mL) and water (30 mL). The aqueous layer was removed and the organic layer was dried (MgSO$_4$), filtered and then concentrated to a residue (0.191 g). The residue was crystallised from a small amount of EtOAc (0.15 g, 97% yield). $^1$H NMR (400 MHz, CDCl$_3$) δ 8.16 (d, J=8.1 Hz, 2H), 8.11 (d, J=8.8 Hz, 2H), 7.49 (d, J=8.7 Hz, 2H), 7.45 (d, J=8.3 Hz, 2H), 4.92-4.17 (m, 4H), 3.79-3.42 (m, 2H), 2.27-1.86 (m, 4H), 1.57-1.32 (m, 9H).

The Boc protected derivative (0.15 g, 0.3 mmol) was suspended in EtOAc (2 mL) and 4M HCl in dioxane (3 mL) was added providing a clear solution. The mixture was stirred at rt overnight and the resultant precipitate was filtered and washed sequentially with small portions of EtOAc, iPrOH, EtOAc and finally ether providing the title compound as an off-white solid (0.117 g, 90% yield). Mp 284° C. dec. $^1$H NMR (400 MHz, DMSO) δ 10.10 (bs, 1H), 9.51 (t, J=6.0 Hz, 1H), 8.67 (bs, 1H), 8.15 (d, J=8.4 Hz, 2H), 8.09 (d, J=8.7 Hz, 2H), 7.68 (d, J=8.7 Hz, 2H), 7.59 (d, J=8.4 Hz, 2H), 5.97 (bs, 1H), 4.49 (d, J=5.9 Hz, 2H), 4.43 (bs, 1H), 4.16 (d, J=1.8 Hz, 1H), 3.43-3.24 (m, 4H), 2.03-1.85 (m, 2H). $^{13}$C NMR (101 MHz, DMSO) δ 175.5, 167.5, 166.8, 144.4, 136.4, 129.5, 128.9, 128.3, 128.1, 125.0, 121.9, 73.9, 66.3, 44.1, 42.3, 32.4. LCMS R$_f$(min)=4.98. MS m/z 399.1 (M+H). HR-ESI calcd for C$_{20}$H$_{20}$ClN$_4$O$_3^+$ (M+H) 399.1218, found 399.1217.

23. Amino(4-((5-(4-chlorophenyl)-1,3,4-oxadiazol-2-yl)amino)phenyl)methaniminium chloride (E-23)

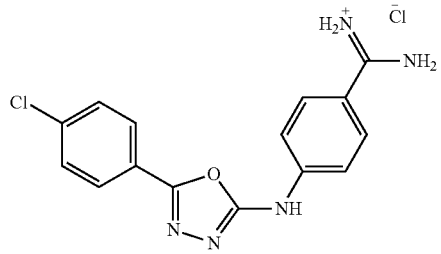 [SMILES: Cl ; N=C(N)c1ccc(Nc2nnc(-c3ccc(Cl)cc3)o2)cc1]

4-Chlorobenzohydrazide (0.532 g, 3.121 mmol) and 4-isothiocyanatobenzonitrile (0.5 g, 3.121 mmol) were combined in THF (15 mL) and stirred at rt overnight. To this mixture was added tosyl chloride (0.714 g, 3.748 mmol) was added followed by pyridine (530 μL, 6.554 mmol). The mixture was refluxed with stirring for 6 h and then stirred at rt overnight. The mixture was diluted with water (50 mL) and the resulting solid was filtered, washed consecutively with water (20 mL), EtOH (5 mL) and finally DCM (20 mL) providing the 4-((5-(4-Chlorophenyl)-1,3,4-oxadiazol-2-yl)amino)benzonitrile as a pale yellow solid (0.45 g, 49% yield). Mp 274-276° C. $^1$H NMR (400 MHz, DMSO) δ 11.34 (s, 1H), 7.92 (d, J=8.8 Hz, 2H), 7.84 (d, J=9.0 Hz, 2H), 7.77 (d, J=9.0 Hz, 2H), 7.67 (d, J=8.8 Hz, 2H).

4-((5-(4-Chlorophenyl)-1,3,4-oxadiazol-2-yl)amino)benzonitrile (0.5 g, 1.685 mmol) was suspended in dioxane (0.5 mL) and DMAP (10.3 mg, 0.0843 mmol) was added followed by Boc$_2$O (1.1 g, 5.055 mmol) and the mixture was stirred in an oil bath (≈60° C.) for approximately 20 min (the evolution of gas ceases). The cooled solution was diluted with EtOAc (30 mL) and filtered through a short silica pad and concentrated to an oily residue (1.17 g). The oil was triturated with 20% EtOAc:petroleum ether providing a white solid that was filtered and washed with 20% EtOAc: petroleum ether (0.495 g, 74% yield,). $^1$H NMR (400 MHz, CDCl$_3$) δ 7.96 (d, J=8.8 Hz, 2H), 7.71 (d, J=8.8 Hz, 2H), 7.52 (d, J=6.3 Hz, 2H), 7.50 (d, J=6.3 Hz, 2H), 1.51 (s, 9H). A portion of the Boc derivative (0.15 g, 0.378 mmol) was dissolved in anhydrous THF (4.5 mL) and cooled in an ice-bath in an N$_2$ atmosphere. 1M LiHMDS in THF (799 μL, 0.799 mmol) was added dropwise to the stirred solution and continued to be stirred ice-cold for 4 h then rt overnight. The next day 4M HCl in dioxane was added dropwise to the ice-cold solution and allowed to stir for 2 h. The mixture was partitioned between 1M HCl (40 mL) and EtOAc (30 mL). The aqueous layer was neutralised with bicarbonate and left to stand for ≈50 h. The precipitate was filtered and washed with water providing a yellow/brown solid (0.038 g). The solid was powdered and then suspended in EtOAc (10 mL) and 4M HCl in dioxane (1 mL) was added to the mixture and stirred for 2 h at rt. The hydrochloride was filtered and washed with plenty of EtOAc and finally ether providing the title compound as a light brown solid (0.036 g, 27% yield). Mp>300° C. $^1$H NMR (400 MHz, DMSO) δ 11.46 (s, 1H), 9.25 (bs, 2H), 8.97 (bs, 2H), 7.92 (d, J=8.7 Hz, 2H), 7.90 (d, J=8.8 Hz, 2H), 7.82 (d, J=8.9 Hz, 2H), 7.68 (d, J=8.7 Hz, 2H). $^{13}$C NMR (101 MHz, DMSO) δ 164.7, 159.4, 157.6, 143.5, 135.8, 129.5, 129.5, 127.4, 122.4, 120.3, 116.7. LCMS R$_f$(min)=4.72. MS m/z 314.1 (M+H). HR-ESI calcd for C$_{15}$H$_{13}$ClN$_5$O$^+$ (M+H) 314.0803, found 314.0799.

24. 4-((5-(4-Iodophenyl)-1,3,4-oxadiazol-2-yl)amino)phenol (E-24)

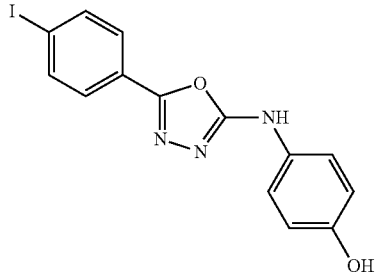 [SMILES: Oc1ccc(Nc2nnc(-c3ccc(I)cc3)o2)cc1]

4-Iodobenzahydride (3.79 g, 14.478 mmol) and 1-isothiocyanato-4-methoxy benzene (2 mL, 14.4784 mmol) in THF (100 mL) were left to stir overnight at rt during which time the mixture formed a white precipitate. On formation of the intermediate, tosyl chloride (3.312 g, 17.374 mmol) and pyridine (2.44 mL, 30.405 mmol) were added and the mixture refluxed to 70° C. for 20 h. H$_2$O (120 mL) was added to the mixture and allowed to stir for 10 mins. The gold precipitate formed was then filtered and recrystallised in hot EtOH (450 mL) to produce 5-(4-iodophenyl)-N-(4-methoxyphenyl)-1,3,4-oxadiazol-2-amine as gold crystalline solid (4.9373 g, 89% yield). Mp=269° C. $^1$H NMR (400 MHz, DMSO) δ 10.49 (s, 1H, NH), 7.95 (d, J=8.6 Hz, 2H, CH), 7.64 (d, J=8.6 Hz, 2H, CH), 7.52 (d, J=9.1 Hz, 2H, CH), 6.95 (d, J=9.1 Hz, 2H, CH), 3.73 (s, 3H, CH$_3$). $^{13}$C NMR (101 MHz, DMSO) δ 160.68 (C), 157.37 (C), 154.95 (C), 138.62 (CH), 132.19 (C), 127.57 (CH), 123.71 (C), 119.09 (CH), 114.78 (CH), 98.28 (C), 55.67 (CH$_3$). LCMS R$_f$(min)=3.510 MS m/z 394.0 (M+H).

To 5-(4-iodophenyl)-N-(4-methoxyphenyl)-1,3,4-oxadiazol-2-amine (1.0 g, 2.543 mmol) in DCM (25 mL) was added BBr$_3$ (2.20 mL, 7.629 mmol) drop wise at 0° C. The mixture was then left to stir at rt for 2 h. On reaction completion, the mixture was quenched with sat. NaHCO$_3$ solution (4 mL) drop wise at 0° C. H$_2$O (100 mL) was then added and the mixture left to stir for 15 mins. The solution was then extracted with EtOAc (3×70 mL) before being dried (MgSO$_4$), filtered and concentrated (0.940 g). Due to the presence of boronate impurities, a second work up was performed. Crude material was dissolved in EtOAc (70 mL) and washed with sat. NaHCO$_3$ (50 mL). The aqueous layer was then collected and extracted with EtOAc (3×50 mL). Combined organic layers were then washed with H$_2$O (50 mL) before being dried (MgSO$_4$), filtered and concentrated to a yellow crystalline solid (0.713 g, 74% yield). Mp=279° C. $^1$H NMR (400 MHz, DMSO) δ 10.34 (s, 1H, NH), 9.18 (s, 1H, OH), 7.95 (d, J=8.6 Hz, 2H, CH), 7.63 (d, J=8.6 Hz, 2H, CH), 7.39 (d, J=8.9 Hz, 2H, CH), 6.76 (d, J=8.9 Hz, 2H, CH). $^{13}$CNMR (101 MHz, DMSO) δ 160.41 (C), 156.95 (C), 152.64 (C), 138.18 (CH), 130.26 (C), 127.11 (CH), 123.43 (C), 118.98 (CH), 115.54 (CH), 97.75 (C). LCMS R$_f$(min)=3.271 MS m/z 258.3 (M+H). HR-ESI calcd for C$_{14}$H$_{10}$IN$_3$O$_2$$^+$ (M+H) 379.9890, found 379.9900.

25. 4-((5-Phenyl-1,3,4-oxadiazol-2-yl)amino)phenol (E-25)

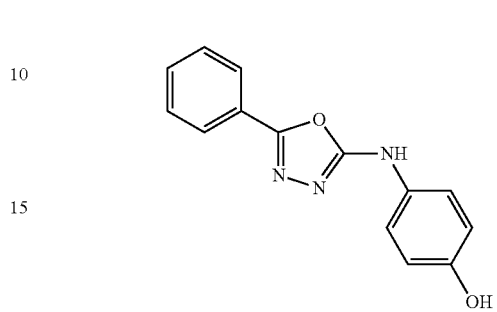

To 5-(4-Iodophenyl)-N-(4-methoxyphenyl)-1,3,4-oxadiazol-2-amine (0.150 g, 0.382 mmol) in EtOAc/MeOH (13.5 mL/4.5 mL) was added Pd/C 10% (0.080 g). To create anhydrous conditions the mixture was subject to vacuum suction and alternated with H$_2$ gas×4. The mixture was then left to stir at rt overnight. On reaction completion, the solution was filtered to remove Pd/C 10% catalyst before being concentrated to form a grey solid. The solid was triturated with DCM and filtered to produce a white crystalline solid (0.053 g). The filtrate was then purified by dissolving it in DCM (50 mL) and washing with sat. NaHCO$_3$ (30 mL). The organic layer was then collected, dried (MgSO$_4$) and filtered before being concentrated to a white solid (0.021 g). Both solid samples of 5-(4-iodophenyl)-N-(4-methoxyphenyl)-1,3,4-oxadiazol-2-amine were combined (74.2 mg, 73% yield). Mp=210° C. $^1$H NMR (400 MHz, DMSO) δ 10.46 (s, 1H, NH), 7.89 (m, 2H, CH), 7.58 (m, J=5.1, 1.9 Hz, 3H, CH), 7.54 (d, J=9.1 Hz, 2H, CH), 6.97 (d, J=9.1 Hz, 2H, CH), 3.75 (s, 3H, CH$_3$). $^{13}$C NMR (101 MHz, DMSO) δ 160.21 (C), 157.56 (C), 154.51 (C), 131.92 (C), 130.91 (C), 129.38 (CH), 125.49 (CH), 123.92 (CH), 118.64 (CH), 114.39 (CH), 55.28 (CH$_3$). LCMS R$_f$ (min) =3.647 MS m/z 268.2 (M+H).

To N-(4-methoxyphenyl)-5-phenyl-1,3,4-oxadiazol-2-amine (0.050 g, 0.187 mmol) in DCM (3 mL) was added BBr$_3$ (0.0710 mL, 0.748 mmol) drop wise at 0° C. The mixture was then left to stir at rt for 2 h. On reaction completion, the mixture was quenched with sat. NaHCO$_3$ (1 mL) drop wise at 0° C. H$_2$O (20 mL) was then added to the mixture which was then allowed to stir for 15 mins. The solution was then extracted with EtOAc (3×50 mL). The combined organic layers were then washed with H$_2$O (50 mL) before being dried (MgSO$_4$), filtered and concentrated to a cream solid. A second workup was performed by dissolving the solid and EtOAc (50 mL) and washing with sat. HCO$_3$ (30 mL). The organic layer was dried (MgSO$_4$), filtered and concentrated to give 4-((5-phenyl-1,3,4-oxadiazol-2-yl)amino)phenol as a cream solid (45.1 mg, 95% yield). Mp=231° C. $^1$H NMR (400 MHz, DMSO) δ 10.29 (s, 1H, NH), 9.15 (s, 1H, OH), 7.87 (m, 2H, CH), 7.56 (m, 3H, CH), 7.40 (d, 2H, CH), 6.75 (d, 2H, CH). $^{13}$C NMR (101 MHz, DMSO) δ 160.37 (C), 157.46 (C), 152.61 (C), 130.83 (C), 130.43 (C), 129.38 (CH), 125.41 (CH), 123.96 (CH), 118.95 (CH), 115.59 (CH). LCMS R$_f$(min)=3.065 MS m/z 254.2 (M+H). HR-ESI calcd for C$_{14}$H$_{11}$N$_3$O$_2$+(M+H) 254.0924, found 254.0928.

26. 4-((5-(4-(Trifluoromethyl)phenyl)-1,3,4-oxadi-azol-2-yl)amino)phenol (E-26)

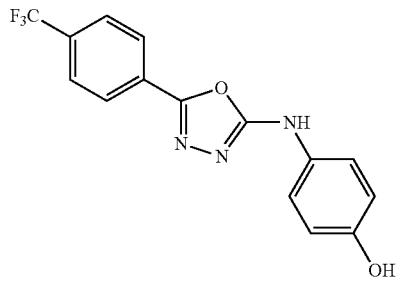 [SMILES: Oc1ccc(Nc2nnc(-c3ccc(C(F)(F)F)cc3)o2)cc1]

4-(trifluoromethyl)benzohydrazine (Chen, Y.; et al. *PloS One*. 2012, 7, e35186) (0.5 g, 2.449 mmol) and 1-isothio-cyanato-4-methoxybenzene (0.338 mL, 2.449 mmol) in THF (20 mL) were left to stir at rt overnight. On formation of the intermediate, tosyl chloride (0.560 g, 2.939 mmol) and pyridine (0.414 mL, 5.143 mmol) were then added and the mixture refluxed to 70° C. for 20 h. H$_2$O (50 mL) was added to the mixture and allowed to stir for 10 mins. The resultant cream precipitate was filtered. The crude material was chromatographed on silica gel eluting with 10% EtOAc: petroleum spirits. The appropriate fractions were collected and concentrated to an off-white solid. The solid was further purified through two recrystallisation steps using hot ethanol to produce N-(4-methoxyphenyl)-5-(4-(trifluoromethyl) phenyl)-1,3,4-oxadiazol-2-amine as a white crystalline solid (0.155 g, 19% yield). Mp=258° C. $^1$H NMR (400 MHz, DMSO) δ 10.58 (s, 1H, NH), 8.09 (d, J=8.2 Hz, 2H, CH), 7.96 (d, J=8.2 Hz, 2H, CH), 7.54 (d, 2H, CH), 6.98 (d, 2H, CH), 3.75 (s, 3H, CH$_3$). $^{13}$C NMR (101 MHz, DMSO) δ 160.84 (C), 156.77 (C), 154.86 (C), 131.88 (C), 130.48 (C), 127.88 (C), 126.57 (CF$_3$), 126.37 (CH), 126.37 (CH), 125.45 (CH), 119.02 (CH), 119.02 (CH), 114.60 (CH), 114.60 (CH), 55.47 (CH$_3$). LCMS R$_f$(min)=3.480 MS m/z 336.1 (M+H).[23] Note: CH adjacent to CF$_3$ group doesn't appear in $^{13}$CNMR due to effects caused by fluorine.

To N-(4-methoxyphenyl)-5-(4-(trifluoromethyl)phenyl)-1,3,4-oxadiazol-2-amine (0.050 g, 0.141 mmol) in DCM (3 mL) was added BBr$_3$ (0.0566 mL, 0.597 mmol) drop wise at 0° C. The mixture was then left to stir at rt for 2 h. On reaction completion, the mixture was quenched with sat. NaHCO$_3$ solution (2 mL) drop wise at 0° C. H$_2$O (20 mL) was then added and the mixture left to stir for 15 mins. The solution was then extracted with EtOAc (3×50 mL). The combined organic layers were then washed with H$_2$O (2×50 mL), sat. NaHCO$_3$ (2×50 mL) and brine (1×30 mL) before being dried (MgSO$_4$), filtered and concentrated to a cream solid. Crude material was recrystallised using a hot EtOH: petroleum spirit combination to produce 4-((5-(4-(trifluoromethyl)phenyl)-1,3,4-oxadiazol-2-yl)amino)phenol as a white solid (0.014 g, 31% yield). Mp=265° C. $^1$H NMR (400 MHz, DMSO) δ 10.42 (s, 1H, NH), 9.20 (s, 1H, OH), 8.07 (d, J=8.2 Hz, 2H, CH), 7.94 (d, J=8.2 Hz, 2H, CH), 7.41 (d, J=8.8 Hz, 2H, CH), 6.78 (d, J=8.8 Hz, 2H, CH). $^{13}$C NMR (101 MHz, DMSO) δ 160.81 (C), 156.50 (C), 152.81 (C), 130.58 (C), 130.19 (C), 127.74 (C), 126.39 (CF$_3$), 126.15 (CH), 119.17 (CH), 115.62 (CH). LCMS R$_f$(min)=3.267 MS m/z 322.1 (M+H). HR-ESI calcd for C$_{15}$H$_{10}$F$_3$N$_3$O$_2$$^+$ (M+H) 322.0798, found 322. 0802. Note: CH adjacent to CF$_3$ group doesn't appear in $^{13}$CNMR due to effects caused by fluorine.

27. 5-(4-Chlorophenyl)-N-[4-(1H-tetrazol-5-yl)phe-nyl]-1,3,4-oxadiazol-2-amine (E-27)

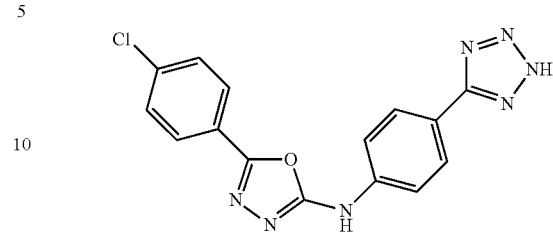

2-Bromo-5-(4-chlorophenyl)-1,3,4-oxadiazole (80.5 mg, 0.310 mmol) and 4-(2H-tetrazol-5-yl) aniline (60 mg, 0.3721 mmol) were dissolved in DMF (1.6 mL). To this, triethylamine (0.20 mL) was added and heated at 90° C. for 4 h. To the reaction mixture was added water and acidified with 10% HCl until pH ~1. The precipitate was filtered and washed with water to give a brown solid. The filtrate was extracted with 75 mL water and 3×50 mL Ethyl acetate and backwashed with 10 mL brine. The organic layer was dried with MgSO4 and reduced in vacuo to leave a yellow solid. Both solids were combined and run through a flash column with straight EA. Fractions were reduced to give a yellow solid. This was recrystallised in EtOH and filtered to give brown crystals (30.6 mg, 29.0%). Decomposes at 210° C. 1H NMR (400 MHz, DMSO): 8.12 (d, 2H, Ar), 7.79 (d, 2H, Ar), 7.75 (d, 2H, Ar), 6.72 (d, 2H, Ar), 5.72 (b, 2H). 13C NMR (101 MHz, DMSO): 164.78, 160.01, 150.93, 142.02, 138.11, 129.74, 128.82, 126.44, 122.05, 113.70, 112.16.

28. 5-(4-Chlorophenyl)-N-[4-(2-oxido-3H-1,2,3,5-oxathiadiazol-4-yl)phenyl]-1,3,4-oxadiazol-2-amine (E-28)

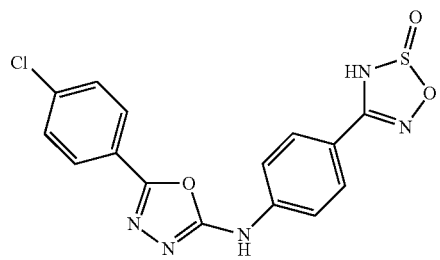 [SMILES: O=S1NC(c2ccc(Nc3nnc(-c4ccc(Cl)cc4)o3)cc2)=NO1]

(Z)-4-((5-(4-Chlorophenyl)-1,3,4-oxadiazol-2-yl)amino)-N'-hydroxybenzimidamide E-9 (50.0 mg, 0.152 mmol) was dissolved in pyridine (24.43 uL, 0.303 mmol) and dry THF (2 mL) which was then purged with N2 gas and cooled to 0° C. Thionyl chloride (17 uL, 0.227 mmol) was dissolved in 0.5 mL dry THF and this solution was added slowly to the reaction mixture. Reaction mixture was stirred at rt for 20 h. This was then cooled on ice and another 100 uL of thionyl chloride was added slowly and then left to stir for 1 h. The reaction mixture was then cooled on ice/brine and water added, leaving to stir for 20 min. The resultant precipitate was filtered, washing with copious water and the ether to give a pale green solid. This was suspended in water, basified with 20% KOH to dissolve solid and filtered, keeping the filtrate. Filtrate was then acidified with 10% HCl and then made neutral with NaHCO3 and left to settle overnight. This was filtered to give a dark green/brown solid which was suspended in EtOH and heated. This was left to cool, sonicated, left to settle and then filtered to give a grey powder (7.8 mg, 12.1%). Decomposes at 211° C. 1H NMR (400 MHZ, DMSO): 10.66 (s, 1H, NH), 10.05 (b, 1H, NH), 7.89 (d, 2H, Ar), 7.65 (d, 2H, Ar), 7.59 (d, 2H, Ar), 6.98 (d, 2H, Ar). 13C NMR (101 MHz, DMSO): 160.06, 156.88, 135.44, 133.55, 133.21, 129.43, 127.20, 122.71, 118.71, 115.77, 112.59

29. 4-((5-(4-(2-Cyclohexylethyl)phenyl)-1,3,4-oxadiazol-2-yl)amino)phenol (E-29)

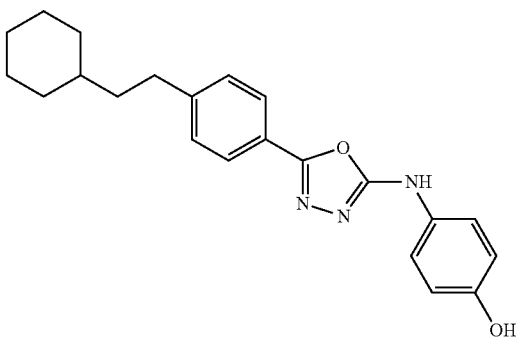 [SMILES: Oc1ccc(Nc2nnc(-c3ccc(CCC4CCCCC4)cc3)o2)cc1]

To 5-(4-iodophenyl)-N-(4-methoxyphenyl)-1,3,4-oxadiazol-2-amine (see synthesis of E-24) (0.2 g, 0.509 mmol) in DMF (3 mL) and $Et_3N$ (3 mL) was added 1-ethynylcyclohexene (0.09 mL, 0.763 mmol) drop wise at rt. $N_2$ was then bubbled through the mixture for 10 mins. $Pd(PPh_3)_2Cl_2$ (0.0179 g, 0.0254 mmol) and CuI (0.00242 g, 0.0127 mmol) were subsequently added while still bubbling through $N_2$. The mixture was left to stir for 18 h at rt. On reaction completion, the solution was diluted in EtOAc (20 mL) and washed with $H_2O$ (2×30 mL) and 1.0M HCl (2×30 mL). The organic layers were then collected and washed with $H_2O$ (1×30 mL) and brine (1×30 mL) before being dried ($MgSO_4$), filtered and concentrated to a brown-cream solid (0.284 g). The crude material was chromatographed on silica gel eluting with 13-30% EtOAc:DCM. The appropriate fractions were collected and concentrated affording 5-(4-(cyclohex-1-en-1-ylethynyl)phenyl)-N-(4-methoxyphenyl)-1,3,4-oxadiazol-2-amine as a gold crystalline solid (0.181 g, 96% yield). Mp=219° C. $^1$H NMR (400 MHz, CDCl3) δ 7.87 (d, J=8.6 Hz, 2H, CH), 7.50 (d, J=8.6 Hz, 2H, CH), 7.44 (d, J=9.0 Hz, 2H, CH), 7.02 (s, 1H), 6.94 (d, J=9.0 Hz, 2H, CH), 6.26 (m, 1H), 3.82 (s, 3H), 2.24 (m, J=2.2 Hz, 2H), 1.66 (m, J=23.9, 5.9, 2.1 Hz, 5H). LCMS $R_f$ (min)=3.867 MS m/z 372.2 (M+H).

To 5-(4-(cyclohex-1-en-1-ylethynyl)phenyl)-N-(4-methoxyphenyl)-1,3,4-oxadiazol-2-amine (0.160 g, 0.4308 mmol) in EtOAc:MeOH (7 mL: 3 mL) was added Pd/C 10% (0.160 g). To create anhydrous conditions the mixture was subject to vacuum suction and alternated with $H_2$ gas×4. The mixture was then left to stir at rt overnight. On reaction completion, the solution was filtered to remove Pd/C 10% catalyst before being concentrated to afford 5-(4-(2-cyclohexylethyl)phenyl)-N-(4-methoxyphenyl)-1,3,4-oxadiazol-2-amine as a white solid (0.105 g, 64% yield). $^1$H NMR (400 MHz, CDCl$_3$) δ 7.84 (d, J=8.3 Hz, 2H, CH), 7.43 (d, J=9.0 Hz, 2H, CH), 7.28 (d, 2H, CH), 6.93 (d, J=9.0 Hz, 2H, CH), 3.81 (s, 3H, $CH_3$), 2.66 (dd, J=9.2, 7.0 Hz, 2H, $CH_2$), 1.71 (m, 9H, $CH_2$), 1.52 (dd, J=16.3, 6.6 Hz, 4H, $CH_2$). $^{13}$C NMR (101 MHz, DMSO) δ 197.41 (C), 195.03 (C), 191.83 (C), 183.33 (C), 169.38 (C), 166.53 (CH), 162.88 (CH), 158.82 (C), 155.97 (CH), 151.77 (CH), 92.68 ($CH_3$), 75.89 ($CH_2$), 74.05 (CH), 70.12 ($CH_2$), 69.78 ($CH_2$), 63.59 ($CH_2$), 63.18 ($CH_2$). 63.18 ($CH_2$). LCMS $R_f$ (min)=4.127 MS m/z 394.3 (M+H).

To 5-(4-(2-cyclohexylethyl)phenyl)-N-(4-methoxyphenyl)-1,3,4-oxadiazol-2-amine (0.096 g, 0.2546 mmol) in DCM (4 mL) was added $BBr_3$ (0.1 mL, 1.0183 mmol) drop wise at 0° C. The mixture was then left to stir at rt for 2 h. On reaction completion, the mixture was quenched with sat. $NaHCO_3$ solution (2 mL) drop wise at 0° C. $H_2O$ (20 mL) was then added and the mixture left to stir for 15 mins. The solution was then extracted with EtOAc (3×50 mL). The combined organic layers were washed with $H_2O$ (1×50 mL) before being dried ($MgSO_4$), filtered and concentrated to a brown solid (0.221 g). The crude material was chromatographed on silica gel eluting with 25-50% EtOAc:DCM. The appropriate fractions were collected and concentrated to a light brown solid (0.109 g, 100% yield). Mp=260° C. $^1$H NMR (400 MHz, DMSO) δ 10.24 (s, 1H, NH), 9.14 (s, 1H, OH), 7.77 (d, J=8.2 Hz, 2H, CH), 7.38 (dd, J=8.5, 4.8 Hz, 4H, CH), 6.75 (d, J=8.9 Hz, 2H, CH), 2.66 (m, 3H, $CH_2$), 1.69 (dd, J=42.6, 11.9 Hz, 6H, $CH_2$), 1.49 (dd, J=15.4, 7.0 Hz, 2H), 1.17 (t, J=7.1 Hz, 2H, $CH_2$), 0.93 (t, J=12.0 Hz, 2H, $CH_2$). $^{13}$C NMR (101 MHz, DMSO) δ 160.12 (C), 157.48 (C), 152.48 (C), 145.79 (C), 130.38 (C), 129.16 (CH), 125.45 (CH), 121.45 (C), 118.82 (CH), 115.52 (CH), 38.44 ($CH_2$), 36.63 (CH), 32.70 ($CH_2$), 32.37 ($CH_2$), 26.17 ($CH_2$), 25.79 ($CH_2$). LCMS $R_f$ (min)=3.788 MS m/z 364.2 (M+H). HR-ESI calcd for $C_{22}H_{25}N_3O_2$+(M+H) 364.202, found 364.2029.

30. 5-(4-Chlorophenyl)-N-(pyridin-4-ylmethyl)-1,3,4-oxadiazol-2-amine (E-30)

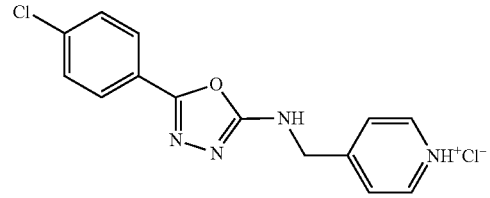

2-Bromo-5-(4-chlorophenyl)-1,3,4-oxadiazole (0.150 g, 0.578 mmol), 4-(aminomethyl)piperidine (0.176 mL, 1.734 mmol) and DIPEA (0.3 mL, 1.734 mmol) in DMF (3 mL) were heated to 70° C. for 3 h in which time the solution changed from yellow to orange. On reaction completion, the mixture was diluted in EtOAc (50 mL) and washed with $H_2O$ (30 mL). The organic layer was collected and washed with $H_2O$ (2×30 mL) and brine (1×30 mL) before being collected, dried ($MgSO_4$), filtered and concentrated to a yellow semi-solid (0.177 g). Crude material was then triturated in $Et_2O$ and filtered to produce an orange solid (0.143 g). To remove impurities, this solid was further dissolved in EtOAc (4 mL), and 2.0M HCl in diethyl ether (1 mL) was added at 0° C. The mixture was left to stir at rt overnight before being filtered and washed with EtOAc, forming a light brown solid (0.054 g, 43% yield). Mp=191° C. $^1$H NMR (400 MHz, DMSO) δ 9.01 (s, 1H, NH), 8.90 (d, J=6.7 Hz, 2H, CH), 8.08 (d, J=6.6 Hz, 2H, CH), 7.82 (d, J=8.7 Hz, 2H, CH), 7.62 (d, J=8.7 Hz, 2H, CH), 4.81 (s, 2H, $CH_2$). $^{13}$C NMR (101 MHz, DMSO) δ 163.35 (C), 159.92 (C), 157.82

(C), 141.45 (CH), 135.75 (C), 129.78 (CH), 127.42 (CH), 125.45 (CH), 123.03 (C), 45.61 (CH$_2$). LCMS R$_f$ (min) =3.185 MS m/z 287.1 (M+H). HR-ESI calcd for C$_{14}$H$_{16}$ClN$_3$O$_2^+$ (M+H) 287.0694, found 287.0706.

31. 4-((5-(4-chlorophenyl)-1,2,4-thiadiazol-3-yl)amino)phenol (E-31)

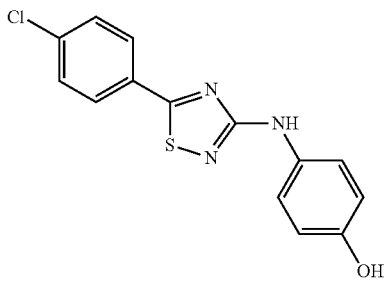 [SMILES: Oc1ccc(Nc2nsc(-c3ccc(Cl)cc3)n2)cc1]

To a solution of trimethyltin-4-chlorophenyl (0.730 g, 1.763 mmol) and 3-bromo-5-chloro 1, 2, 4-thiadiazole (0.17 mL, 1.763 mmol) in dry dioxane (5.5 mL) was added Pd(PPh$_3$)$_4$ (0.102 g, 0.0882 mmol) and CuTC (0.034 g, 0.176 mmol). N$_2$ gas was then bubbled through the mixture for 10 min to remove any oxygen. The mixture was then heated to 60° C. and left to stir overnight. On reaction completion, the mixture was partitioned in EtOAc (50 mL) and washed with H$_2$O (2×30 mL). The aqueous layers were then collected and back extracted with EtOAc (2×30 mL). The organic layers were then combined, before being dried (MgSO$_4$), filtered and concentrated to a brown solid (0.994 g). The crude material was then chromatographed on silica gel eluting with 5% EtOAc, 95% PS. The appropriate fractions were collected and concentrated to a yield 3-bromo-5-(4-chlorophenyl)-1,2,4-thiadiazole as a white solid (0.336 g, 69% yield). $^1$H NMR (400 MHz, CDCl$_3$) δ 7.89 (d, J=8.8 Hz, 2H), 7.50 (d, J=8.8 Hz, 2H). $^{13}$C NMR (101 MHz, CDCl$_3$) δ 189.1, 146.2, 139.3, 129.9, 128.7, 127.9. LCMS R$_f$ (min)=4.14. MS m/z 275.0 (M+2H).

A solution of 3-bromo-5-(4-chlorophenyl)-1,2,4-thiadiazole (0.129 g, 0.468 mmol) from above, p-anisidine (0.231 g, 1.873 mmol) and DIPEA (0.38 mL, 2.107 mmol) in dry NMP (2 mL) was heated to 160° C. in a microwave reactor for 3.5 h. On reaction completion, the mixture was diluted with EtOAc (50 mL) and washed with 0.5M HCl (20 mL), H$_2$O (2×20 mL) and brine (20 mL). The aqueous layers were then collected and back extracted with EtOAc (3×30 mL). The organic layers were then combined before being dried (MgSO$_4$), filtered and concentrated to a dark brown solid (0.09 g). Trituration with DCM lead to a crystalline gold solid being produced (0.022 g). The filtrate was then chromatographed on silica gel eluting with 10% EtOAc, 90% PS. The appropriate fractions were collected and concentrated to a gold crystalline material 5-(4-chlorophenyl)-N-(4-methoxyphenyl)-1,2,4-thiadiazol-3-amine (0.077 g, 51% yield). $^1$H NMR (400 MHz, DMSO) δ 10.20 (s, 1H), 7.98 (d, J=8.7 Hz, 2H), 7.67 (dd, J=8.9, 2.3 Hz, 4H), 6.90 (d, J=9.1 Hz, 2H), 3.72 (s, 3H). $^{13}$C NMR (101 MHz, DMSO) δ 183.8, 166.7, 154.0, 136.8, 133.9, 129.7, 128.7, 128.7, 118.5, 114.0, 55.2. LCMS R$_f$ (min)=7.03. MS m/z 318.0 (M+H).

To a solution of 5-(4-chlorophenyl)-N-(4-methoxyphenyl)-1,2,4-thiadiazol-3-amine (0.048 g, 0.151 mmol) from above in dry DCM (2.5 mL) was added BBr$_3$ (0.057 mL, 0.604 mmol) dropwise at 0° C. The mixture was then left to stir at room temperature for 2 h. On reaction completion, the mixture was quenched with sat. NaHCO$_3$ (5 mL). H$_2$O (20 mL) was then added and the mixture left to stir for ½ h. The solution was then extracted with EtOAc (3×20 mL). The organic layers were combined and washed with NaHCO$_3$ (2×20 mL) and brine (10 mL) before being dried (MgSO$_4$), filtered and concentrated to dark brown solid (0.037 g). The crude material was then chromatographed on silica gel eluting with 15% EtOAc: 85% PS. The appropriate fractions were collected and concentrated to give 4-((5-(4-chlorophenyl)-1,2,4-thiadiazol-3-yl)amino)phenol as a brown crystalline solid (0.019 g, 41% yield). $^1$H NMR (400 MHz, DMSO) δ 10.06 (s, 1H), 9.04 (s, 1H), 7.97 (d, J=8.6 Hz, 2H), 7.66 (d, J=8.6 Hz, 2H), 7.54 (d, J=8.9 Hz, 2H), 6.71 (d, J=8.9 Hz, 2H). $^{13}$C NMR (101 MHz, DMSO) δ 183.7, 166.9, 152.0, 136.7, 132.5, 129.7, 128.8, 128.7, 118.8, 115.2. LCMS R$_f$ (min)=6.36. MS m/z 304.0 (M+H). HR-ESI calcd for C$_{14}$H$_{10}$ClN$_3$OS$^+$ (M+H) 304.0306, found 304.0316.

32. 4-((3-(4-chlorophenyl)-1,2,4-thiadiazol-5-yl)amino)phenol (E-32)

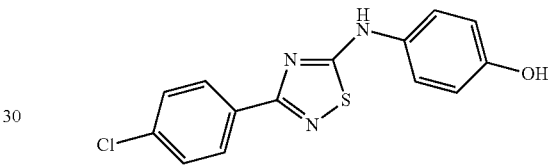

3-Bromo-N-(4-methoxyphenyl)-1,2,4-thiadiazol-5-amine (Barth J. A. *J. Prakt. Chem.* 1987, 329, 355-358) (0.05 g, 0.175 mmol), DMAP (0.002 g, 0.00875 mmol) and Boc$_2$O (0.115 g, 0.525 mmol) were suspended in dry dioxane (0.5 mL). The mixture was then heated to 60° C. for 20 min, at which point the evolution of gas ceased. After reaction completion, the cooled solution was diluted with EtOAc (30 mL) and filtered through a short silica plug. The solution was concentration under pressure to produce tert-butyl(3-bromo-1,2,4-thiadiazol-5-yl)(4-methoxyphenyl)carbamate as a pale yellow solid (0.068 g, 100% yield). $^1$H NMR (400 MHz, DMSO) δ 7.37 (d, J=9.0 Hz, 2H), 7.03 (d, J=9.0 Hz, 2H), 3.82 (s, 3H), 1.40 (s, 9H). $^{13}$C NMR (101 MHz, CDCl$_3$) δ 180.3, 159.6, 153.4, 146.8, 140.8, 130.1, 128.8, 114.6, 55.5, 27.9, 27.4. LCMS R$_f$ (min)=4.11. MS m/z 387.2 (M+H).

To tert-butyl (3-bromo-1,2,4-thiadiazol-5-yl)(4-methoxyphenyl)carbamate (0.140 g, 0.363 mmol) from above and trimethyltin-4-chlorophenyl (0.200 g, 0.725 mmol) in dry dioxane (5 mL) was added Pd(tBu$_3$P)$_2$ (0.010 g, 0.0181 mmol). N$_2$ gas was then bubbled through the mixture for 10 min to remove any oxygen. The mixture was then heated to reflux and left to stir overnight. On reaction completion, the mixture was diluted with EtOAc (50 mL) and washed with H$_2$O (2×20 mL). The aqueous layers were collected and back extracted with EtOAc (2×20 mL). The organic layers were then combined before being dried (MgSO$_4$), filtered and concentrated to a brown solid (0.254 g). The crude material was then chromatographed on silica gel eluting with 5% EtOAc: 95% PS. The appropriate fractions were collected and concentrated to give tert-butyl (3-(4-chlorophenyl)-1,2,4-thiadiazol-5-yl)(4-methoxyphenyl)carbamate as a light tan crystalline solid (0.069 g, 44% yield). $^1$H NMR (400 MHz, CDCl$_3$) δ 7.98 (d, J=8.7 Hz, 2H), 7.31 (d, J=8.7 Hz, 2H), 7.20 (d, J=9.0 Hz, 2H), 6.99 (d, J=9.0 Hz, 2H), 3.90

(s, 3H), 1.48 (s, 9H). $^{13}$C NMR (101 MHz, CDCl$_3$) δ 179.6, 166.6, 159.4, 153.6, 135.9, 131.8, 131.2, 129.4, 129.2, 128.7, 114.4, 85.0, 55.6, 31.1, 28.1. LCMS R$_f$(min)=4.761. MS m/z 418.1 (M+H).

To tert-butyl (3-(4-chlorophenyl)-1,2,4-thiadiazol-5-yl) (4-methoxyphenyl)carbamate (0.0224 g, 0.0536 mmol) from above in dry DCM (1 mL) was added TFA (0.1 mL) dropwise at 0° C. The mixture was then left to stir at room temperature for 2.5 h. On reaction completion, the mixture was then reduced under pressure to produce 3-(4-chlorophenyl)-N-(4-methoxyphenyl)-1,2,4-thiadiazol-5-amine as a light brown crystalline solid (0.017 g, 100% yield). $^1$H NMR (400 MHz, CDCl$_3$) δ 8.05 (d, J=8.6 Hz, 2H), 7.52 (d, J=8.6 Hz, 2H), 7.29-7.24 (m, 2H), 7.00 (d, J=8.9 Hz, 2H), 3.85 (s, 3H). $^{13}$C NMR (101 MHz, CDCl$_3$) δ 179.9, 160.5, 158.9, 138.7, 130.7, 129.7, 129.2, 126.7, 122.6, 115.6, 55.8. LCMS R$_f$(min)=6.97. MS m/z 318.0 (M+H).

To 3-(4-chlorophenyl)-N-(4-methoxyphenyl)-1,2,4-thiadiazol-5-amine (0.0284 g, 0.0894 mmol) from above in dry DCM (1 mL) was added BBr$_3$ (0.025 mL, 0.268 mmol) dropwise at 0° C. The mixture was then left to stir at room temperature for 2 h. On reaction completion, the mixture was quenched with sat. NaHCO$_3$ (3 mL). H$_2$O (15 mL) was then added and the mixture left to stir for ½ h. The solution was then extracted with EtOAc (3×20 mL). The organic layers were combined and washed with NaHCO$_3$ (2×20 mL) and brine (10 mL) before being dried (MgSO$_4$), filtered and concentrated to brown solid (0.024 g). The crude material was then chromatographed on silica gel eluting with 30% EtOAc: 70% PS. The appropriate fractions were collected and concentrated to give 4-((3-(4-chlorophenyl)-1,2,4-thiadiazol-5-yl)amino)phenol as a light brown crystalline solid (0.017 g, 62% yield). $^1$H NMR (400 MHz, CDCl$_3$) δ 8.12 (d, J=8.7 Hz, 2H), 7.42 (d, J=8.7 Hz, 2H), 7.21 (d, J=8.8 Hz, 2H), 6.91 (d, J=8.8 Hz, 2H). $^{13}$C NMR (101 MHz, DMSO) δ 167.5, 153.8, 134.8, 131.7, 129.3, 128.9, 120.3, 115.9. LCMS R$_f$(min)=6.31. MS m/z 304.0 (M+H). HR-ESI calcd for C$_{14}$H$_{10}$ClN$_3$OS$^+$ (M+H) 304.0306, found 304.0317.

Example 2

Inhibition of Sphingosine Kinases 1 and 2 and Des1, and Activity Against Cancer Cell Lines Some exemplary compounds of the disclosure were assessed for their enzyme inhibitory and anti-cancer activity, together with the reference compound SK-II. The compound SKI-II has been identified as a SphK1 inhibitor (French K. J. et al. *J. Pharmacol. Exp. Ther.* 2006, 318, 596-603), promoter of SphK1 degradation (Loveridge, C. et al. *J. Biol. Chem.* 2010, 285, 38841-38852) and, more recently, as a Des1 inhibitor (Cingolani, F. et al. *J. Lipid Res.* 2014, 55, 1711-1720). The results are depicted in Table 2.

SphK1/2 Activity Assay

The SphK assays employed, measure SphK activity through the production of $^{32}$P-labelled S1P following the addition of exogenous Sph and [γ$^{32}$P] ATP.

Activities of SphK1 and SphK2 were determined using identical assay conditions with the exception that SphK1 assays used 3 ng/assay recombinant his tagged human SphK1 (made in the lab in a baculovirus system using insect cells), while SphK2 assays used 30 ng/assay recombinant human SphK2 (purchased by Johnson and Johnson).

Solutions were prepared with analytical reagents using distilled water, and were stored at room temperature (unless otherwise indicated). All procedures using [γ$^{32}$P]ATP followed standard radiation safety techniques and were performed with protective perspex shielding. Radiation was monitored with a Geiger counter.

Compounds were dissolved in DMSO at 10 mM, the mixture was vortexed (and sonicated if necessary). Stock solutions were kept at 4° C. until used.

Aliquots were made containing 100 μM drug compound. These aliquots were then diluted in assay buffer: 100 mM tris/HCl pH 7.4, 100 mM NaCl, 1 mM sodium orthovanadate, 10 mM NaF to make up a 10 μM solution.

Sample Preparation

Recombinant enzyme was diluted in assay buffer (above) to make up a final concentration of 0.03 ng/μL (SphK1) or 0.33 ng/μL (SphK2).

Sphingosine Substrate Preparation

40 μL recombinant enzyme was added to an Eppendorf® Safe-Lock® microcentrifuge tube. This was followed by the addition of drug compound from prepared aliquots, before adding ATP, [γ$^{32}$P]ATP and Sph. Note: ATP stock is made up in 1M Tris pH 7.4 and 200 mM MgCl$_2$. This allows ATP to complex with Mg and be available as a substrate.

The solution was then sonicated on ice until becoming clear.

Prepared aliquots can then be stored at −20° C.

Incubation

The rest of the reaction mixture was then added to the enzyme sample (Table 1). All reactions were performed as triplicates.

TABLE 1

Example of assay set-up.

| Reagent | Volume per assay (μL) | |
|---|---|---|
| | SphK1 | SphK2 |
| Drug Compound | 10 | 10 |
| 20 mM Mg-ATP | 0.5 | 0.5 |
| 1 μCi [γ$^{32}$P]ATP | 0.1 | 0.1 |
| 2 mM Sph in 2% fatty acid-free BSA | 0.5 | 0.5 |
| Assay buffer | 48.9 | 48.9 |
| Recombinant SPHK1 protein | 40 | 0 |
| Recombinant SPHK2 protein | 0 | 40 |
| Total Volume | 100 | 100 |

Reaction mixture was prepared with sufficient volume to assay all of the required samples. To do this, each of the volumes shown was multiplied by n+1, where n is the number of samples to be assayed. Assay buffer used is made up of 100 mM tris/HCl pH 7.4, 100 mM NaCl, 1 mM sodium orthovanadate and 10 mM NaF.

The mixture was then incubated at 37° C. for 20 min (SphK1)/45 min (SphK2).

A tenfold serial dilution of the leftover reaction mixture in water was performed for later conversion of radioactive signal to phosphate concentration. 2 μL of the 1 in 10, 1 in 100, and 1 in 1,000 dilutions was spotted onto pre-marked Whatman paper.

Extraction

To the 100 μL assay mixture, add 270 μl of chloroform/methanol/conc. HCl (100:200:1).

20 μL of 5 M KCl was then added to the assay mixture. 70 μL of chloroform was added to create phase separation. The solution was vortexed to mix well.

The solution was then centrifuged for 5 min at 13,000×g to fully separate the phases.

The upper aqueous/methanol phase was separated by aspiration.

Thin-Layer-Chromatography

A 20×20-cm Silica TLC plate was then cut in half.

The TLC plate was measured 2 cm from the bottom and using pencil a line was drawn along the edge. Samples were then applied (the origin) to the line no closer than 1.5 cm from the edge of the plate and no closer than 1.3 cm to each other.

50 µL of the remaining lower chloroform phase of the lower chloroform phase was applied onto the TLC plate by repeatedly spotting a few microliters of liquid (<5 mm diameter circle) between each sample spot with the pipette tip. The liquid was then allowed to absorb into the plate before drying with a stream of air.

Resolution and Quantitation of SW

The TLC plate was developed in a glass TLC developing tank with 1-butanol/ethanol/glacial acetic acid/$H_2O$ (8:2:1:2) until the mobile phase is within 1 cm of the top of the TLC plate.

The TLC plate was removed from the developing tank with tweezers and air dried for 15 min. The TLC plate was then covered in cling wrap/placed in a zip-lock plastic bag.

The TLC plate was then exposed to a storage phosphor screen overnight. Storage phosphor screens work by capturing images produced by ionising radiation (e.g. $^{32}P$). The phosphorimager stimulates the screen which uses lasers to convert the latent signal to light. Light is proportional to the amount of radioactivity in the sample. The image is then quantified using standard quantification software (ImageQuant™). Whatman paper with the assay mixture dilutions, was included to assist quantification of the phosphor signal.

Once the storage phosphor screen was read using the phosphorimager, S1P spots, which have an $R_f$ of 0.7 with the mobile phase employed, were quantified.

Using a $[\gamma^{32}P]ATP$ standard curve, the sample protein concentrations, and a multiplication coefficient of 4.27, incomplete S1P extraction (~25%) and spotting of only part of the chloroform phase onto the TLC plate was accounted for. The S1P spot intensity can be converted to the amount of phosphate transferred/min/mg protein.

Measurement of Dihydroceramide Desaturase-1 (Des1) Activity:

Measurement of Des1 activity was performed by HPLC using intact Jurkat cells labeled with DhCer-C6-NBD as described previously (Munoz-Olaya, J. M. et al. *ChemMedChem* 2008, 3, 946-953) with modifications to enhance sensitivity and reproducibility. These modifications included the use of parental Jurkat cells, 0.5% serum in the culture media, and cell harvesting via centrifugation at 500×g to maximise ceramide extraction. Extracted samples (50 ul) were analysed on a Waters HPLC coupled to a fluorescence detector using a 30 cm C18 reverse-phase column eluted with 1 ml/min 20% $H_2O$ and 80% acetonitrile, both with a 0.1% of trifluoroacetic acid. NBD-labelled substrate and product were quantitated with an excitation and emission wavelengths of 465 nm and 530 nm, respectively.

Measurement of Anticancer Activity in PC3 Cell Line Assays

Routine Cell Culture

PC3 prostate cancer cell lines were cultured in DMEM (containing 10% fetal calf serum and penicillin-streptomycin).

A frozen aliquot of cells was resuspended in 5 mL of warm media and centrifuged for 5 mins at 200×g. The supernatant was aspirated and cell pellet resuspended in 5 mL media.

Cells were then grown in tissue culture flasks at 37° C. with 5% $CO_2$ and passaged when 80-90% confluent 4 times before use.

Plating

Cells were then incubated for 5 mins with Trypsin to separate from cell culture flanks. Enzymatic activity was then quenched with an equal volume of serum containing media.

The cell suspension was then centrifuged at 200×g for 5 mins and the pellet resuspended in 5 mL of media. Cells were exposed to Trypan blue (excludes dead cells) and counted with a haemocytometer.

Before treatment with drug compounds, cells were plated at 2,500 cells/well in 96 well plates and incubated at 37° C. with 5% $CO_2$ in a humidified incubator for 24 hours prior. Cells were only plated in columns 3-10 and rows C—F to ensure uniform humidity and warmth across all wells. The remaining wells were filled with 100 µL of phosphate buffered saline.

Drug Treatment

Drug stock solutions (50 or 10 mM) were diluted×1000 in media to a final concentration of either 50 µM or 10 µM with a DMSO vehicle concentration of 0.1%. Compounds are then serially diluted in media (containing 0.1% DMSO) to give 8 final concentrations, all at 0.1% DMSO.

Cell culture supernatants were aspirated and replaced with drug containing media. Drug treatments were performed in duplicate wells, while potential plate layout-specific variation in cell growth was accounted for by addition of a vehicle control (0.1% DMSO). An untreated control (media only) and active compound control (50 µM SK-II) was included in each assay.

Cells were then incubated with drug compounds at 37° C. with 5% $CO_2$ in a humidified incubator for 72 hours prior to assay.

Cell Viability Assay

Media was diluted with CellTitre $AQ_{ueous}$ One Solution (Promega, Australia; Cat # G3580) according to manufacturer's instructions to produce a final concentration of 317 µg/mL.

Cell culture supernatants were then aspirated from wells and replaced with 100 µL of CellTitre solution. Triplicate cell-free control wells containing only CellTitre solution were also included in each assay.

Cells were then incubated at 37° C. with 5% $CO_2$ in a humidified incubator for 1 hour at which time absorbance was read at 490 nm with an EnVision microplate reader (Perkin Elmer, Australia).

Data Analysis

When analysing data, background absorbance (taken from cell-free control wells) was subtracted from each reading. To determine percentage inhibition of cell viability, absorbance readings for each drug treatment were expressed as a fraction of the vehicle control (0.1% DMSO) readings. For each drug concentration the mean (±SEM) is calculated and graphed using GraphPad Prism (version 5). A sigmoidal curved is fitted to the data and used to calculate the $IC_{50}$ of each compound.

Measurement of Anticancer Activity in MCF7 Cell Lines

MCF7 breast cancer cells were treated with the test compounds and incubated at 37° C., 5% $CO_2$ in air for 72 hrs. The MTS assay was conducted with addition of prepared MTS solution followed by 2 hr incubation, an OD reading and the raw data recorded. The data was managed in tabular form, values adjusted for vehicle control, and the adjusted values graphed as a sigmoidal curve and the $EC_{50}$ value calculated.

TABLE 2

Des1, SphK1 and SphK 2 inhibition and cell line activity.

| Example (E-X) | Compound Structure | SphK1% activity at 10 μm[a] | SphK2% actvity at 10 μm[a] | Des 1 IC$_{50}$ μM | PC3 IC$_{50}$ μM[b] | MCF-7 IC$_{50}$ μM[b] |
|---|---|---|---|---|---|---|
| E-1 | 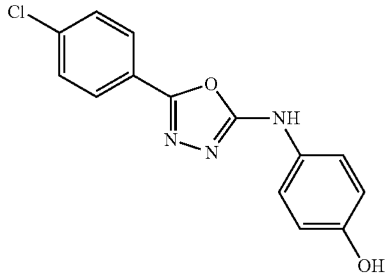 [SMILES: Oc1ccc(Nc2nnc(-c3ccc(Cl)cc3)o2)cc1] | 20-50 | 20-50 | 0.1-1 | 0.1-1.0 | 10-100 |
| E-2 | 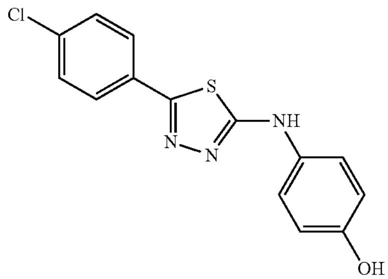 [SMILES: Oc1ccc(Nc2nnc(-c3ccc(Cl)cc3)s2)cc1] | ND | ND | 1-10 | 1-10 | >100 |
| E-3 | 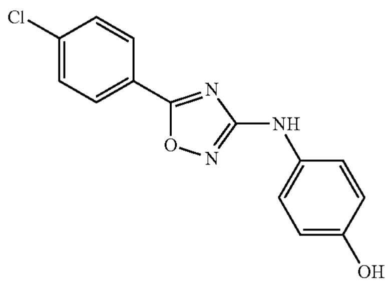 | 20-50 | 50-80 | 1-10 | 10-100 | 10-100 |
| E-4 | 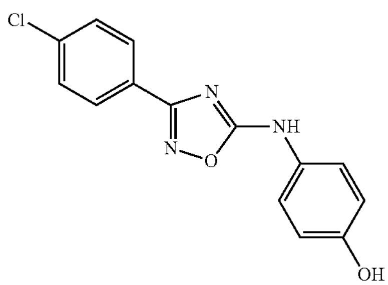 [SMILES: Oc1ccc(Nc2nc(-c3ccc(Cl)cc3)no2)cc1] | 20-50 | 50-80 | 1-10 | 1.0-10 | 10-100 |
| E-5 | 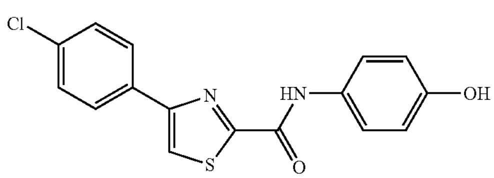 [SMILES: O=C(Nc1ccc(O)cc1)c1nc(-c2ccc(Cl)cc2)cs1] | ND | ND | — | 10-100 | 10-100 |
| E-6 | 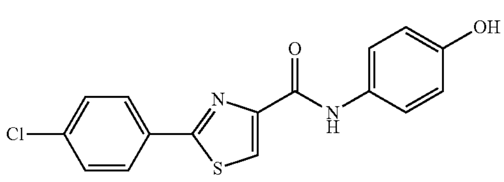 [SMILES: O=C(Nc1ccc(O)cc1)c1csc(-c2ccc(Cl)cc2)n1] | 20-50 | 50-80 | — | >100 | ND |

TABLE 2-continued

Des1, SphK1 and SphK 2 inhibition and cell line activity.

| Example (E-X) | Compound Structure | SphK1% activity at 10 μm$^a$ | SphK2% actvity at 10 μm$^a$ | Des 1 IC$_{50}$ μM | PC3 IC$_{50}$ μM$^b$ | MCF-7 IC$_{50}$ μM$^b$ |
|---|---|---|---|---|---|---|
| E-7 | 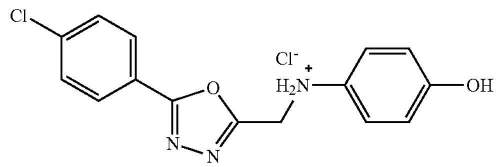 [SMILES: Oc1ccc([NH2+]Cc2nnc(-c3ccc(Cl)cc3)o2)cc1 ; [Cl-]] | 20-50 | 20-50 | — | 10-100 | >100 |
| E-8 | 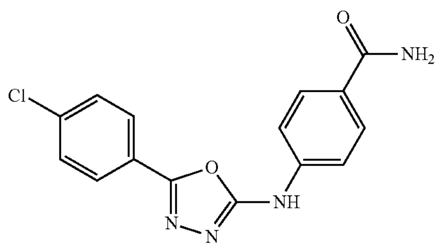 [SMILES: NC(=O)c1ccc(Nc2nnc(-c3ccc(Cl)cc3)o2)cc1] | 20-50 | 20-50 | — | >100 | ND |
| E-9 | 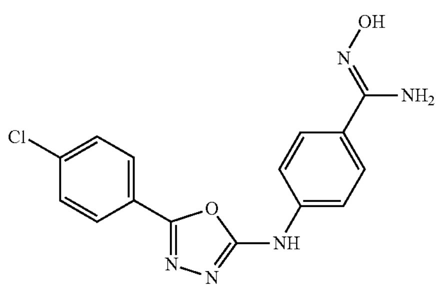 [SMILES: N/C(=N\O)c1ccc(Nc2nnc(-c3ccc(Cl)cc3)o2)cc1] | 80-100 | 100-150 | 1-10 | 0.1-1.0 | ND |
| E-10 | 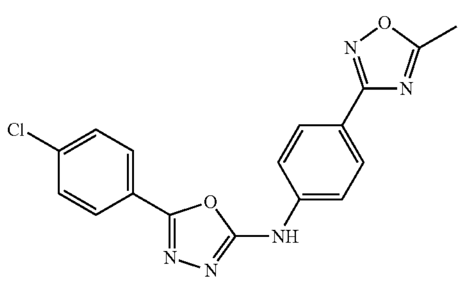 [SMILES: Cc1nc(-c2ccc(Nc3nnc(-c4ccc(Cl)cc4)o3)cc2)no1] | 80-100 | 50-80 | — | >100 | ND |
| E-11 | 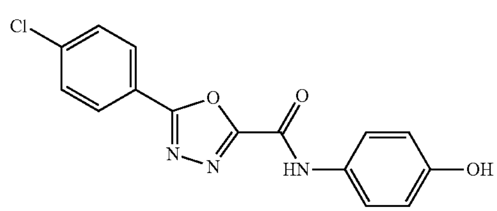 [SMILES: O=C(Nc1ccc(O)cc1)c1nnc(-c2ccc(Cl)cc2)o1] | 50-80 | 100-150 | — | 10-100 | ND |
| E-12 | 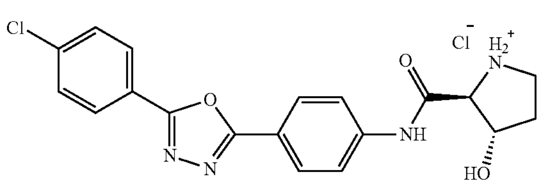 | 50-80 | 20-50 | — | >100 | ND |

TABLE 2-continued

Des1, SphK1 and SphK 2 inhibition and cell line activity.

| Example (E-X) | Compound Structure | SphK1% activity at 10 μm[a] | SphK2% actvity at 10 μm[a] | Des 1 IC$_{50}$ μM | PC3 IC$_{50}$ μM[b] | MCF-7 IC$_{50}$ μM[b] |
|---|---|---|---|---|---|---|
| E-13 | 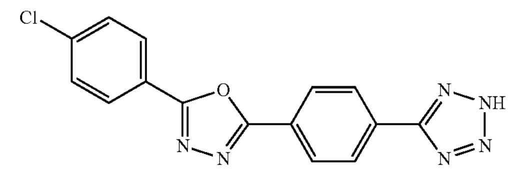 [SMILES: Clc1ccc(-c2nnc(-c3ccc(-c4nn[nH]n4)cc3)o2)cc1] | 100-150 | 5-20 | — | >100 | ND |
| E-14 | 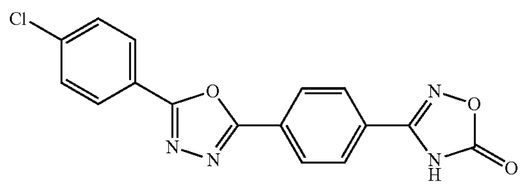 [SMILES: O=c1[nH]c(-c2ccc(-c3nnc(-c4ccc(Cl)cc4)o3)cc2)no1] | 100-150 | 80-100 | — | >100 | ND |
| E-15 | 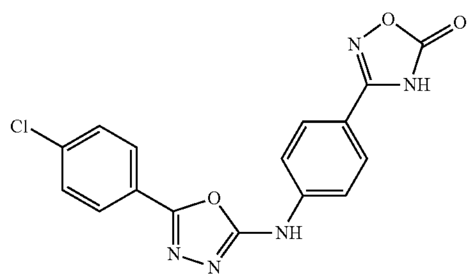 [SMILES: O=c1[nH]c(-c2ccc(Nc3nnc(-c4ccc(Cl)cc4)o3)cc2)no1] | 50-80 | 80-100 | — | 0.1-1.0 | ND |
| E-16 | 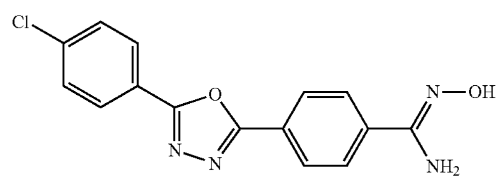 [SMILES: N/C(=N\O)c1ccc(-c2nnc(-c3ccc(Cl)cc3)o2)cc1] | 100-150 | 100-150 | inactive | 0.1-1.0 | ND |
| E-17 | 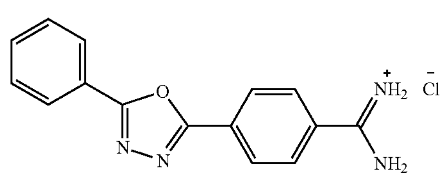 [SMILES: NC(=[NH2+])c1ccc(-c2nnc(-c3ccccc3)o2)cc1 ; [Cl-]] | 200-300 | 80-100 | — | >100 | ND |
| E-18 | 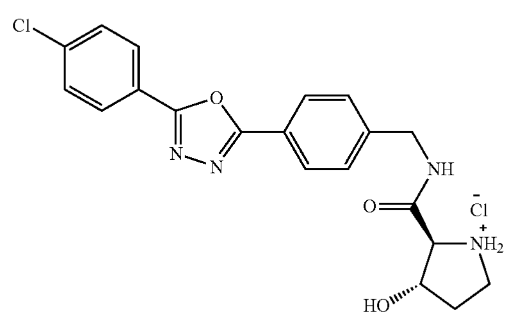 [SMILES: O=C(NCc1ccc(-c2nnc(-c3ccc(Cl)cc3)o2)cc1)[C@H]1[NH2+]CC[C@@H]1O ; [Cl-]] | 50-80 | 80-100 | — | >100 | ND |
| E-19 | 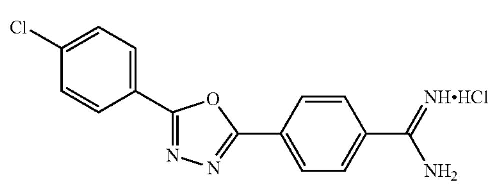 | 50-80 | 80-100 | — | >100 | ND |

TABLE 2-continued

Des1, SphK1 and SphK 2 inhibition and cell line activity.

| Example (E-X) | Compound Structure | SphK1% activity at 10 μm[a] | SphK2% actvity at 10 μm[a] | Des 1 IC$_{50}$ μM | PC3 IC$_{50}$ μM[b] | MCF-7 IC$_{50}$ μM[b] |
|---|---|---|---|---|---|---|
| E-20 | 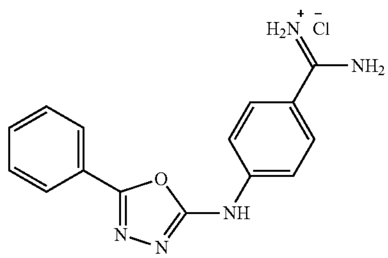 [SMILES: NC(=[NH2+])c1ccc(Nc2nnc(-c3ccccc3)o2)cc1 ; [Cl-]] | 80-100 | 20-50 | — | >100 | ND |
| E-21 | 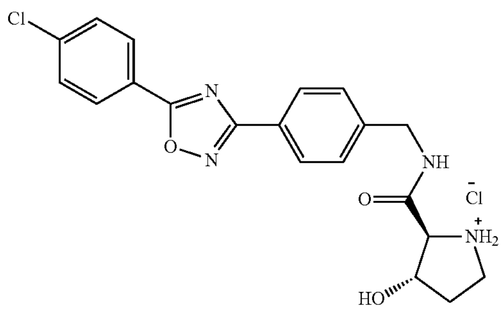 [SMILES: O=C(NCc1ccc(-c2noc(-c3ccc(Cl)cc3)n2)cc1)[C@H]1[NH2+]CC[C@@H]1O ; [Cl-]] | 50-80 | 100-150 | — | 10-100 | ND |
| E-22 | 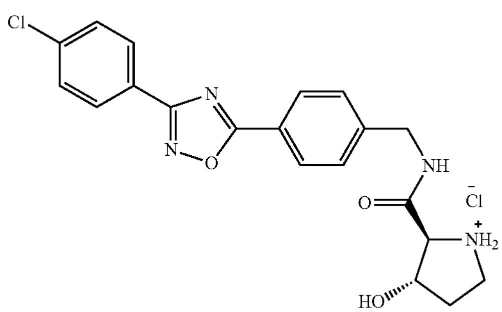 [SMILES: O=C(NCc1ccc(-c2nc(-c3ccc(Cl)cc3)no2)cc1)[C@H]1[NH2+]CC[C@@H]1O ; [Cl-]] | 20-50 | 100-150 | — | >100 | ND |
| E-23 | 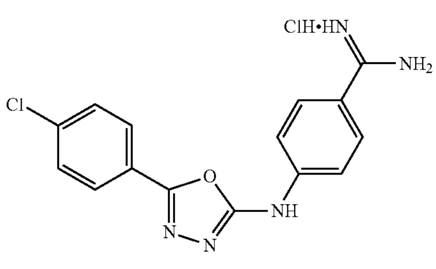 | 20-50 | 5-20 | inactive | >100 | ND |
| E-24 | 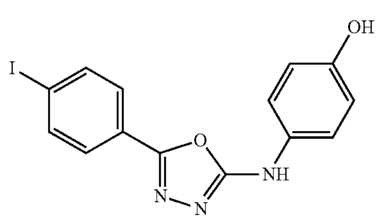 [SMILES: Oc1ccc(Nc2nnc(-c3ccc(I)cc3)o2)cc1] | 50-80 | 1-5 | 1-10 | 0.1-1.0 | ND |

TABLE 2-continued

Des1, SphK1 and SphK 2 inhibition and cell line activity.

| Example (E-X) | Compound Structure | SphK1% activity at 10 μm[a] | SphK2% actvity at 10 μm[a] | Des 1 IC$_{50}$ μM | PC3 IC$_{50}$ μM[b] | MCF-7 IC$_{50}$ μM[b] |
|---|---|---|---|---|---|---|
| E-25 | 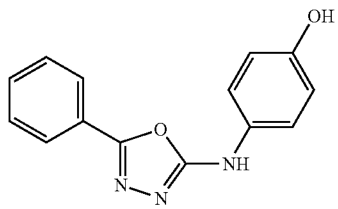 [SMILES: Oc1ccc(Nc2nnc(-c3ccccc3)o2)cc1] | 50-80 | 20-50 | 1-10 | 1.0-10 | ND |
| E26 | 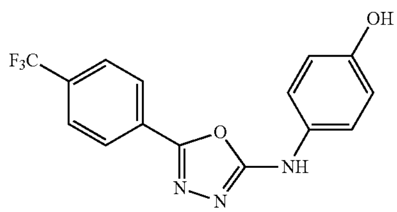 [SMILES: Oc1ccc(Nc2nnc(-c3ccc(C(F)(F)F)cc3)o2)cc1] | 20-50 | 5-20 | 0.1-1 | 1.0-10 | ND |
| E-27 | 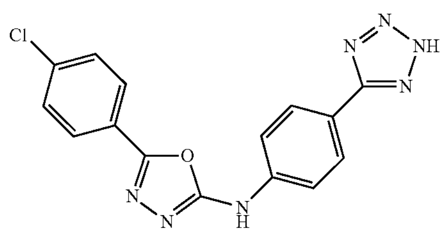 [SMILES: Clc1ccc(-c2nnc(Nc3ccc(-c4nn[nH]n4)cc3)o2)cc1] | 20-50 | 50-80 | inactive | 10-100 | ND |
| E-28 | 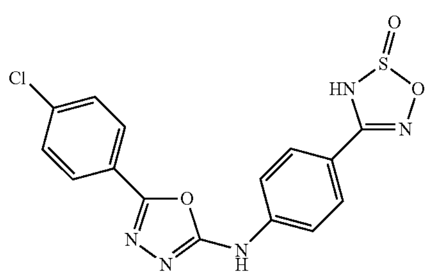 [SMILES: O=S1NC(c2ccc(Nc3nnc(-c4ccc(Cl)cc4)o3)cc2)=NO1] | <1 | 5-20 | 1-10 | 10-100 | ND |
| E-29 | 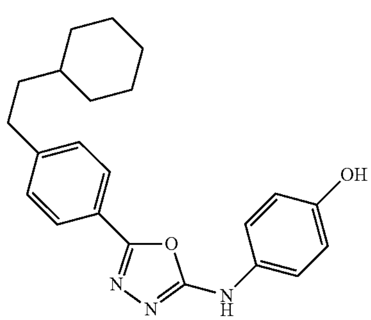 [SMILES: Oc1ccc(Nc2nnc(-c3ccc(CCC4CCCCC4)cc3)o2)cc1] | 50-80 | 100-150 | — | 10-100 | ND |
| E-30 | 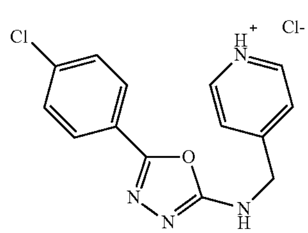 | 1-5 | 20-50 | — | >100 | ND |

TABLE 2-continued

Des1, SphK1 and SphK 2 inhibition and cell line activity.

| Example (E-X) | Compound Structure | SphK1% activity at 10 μm[a] | SphK2% actvity at 10 μm[a] | Des 1 IC$_{50}$ μM | PC3 IC$_{50}$ μM[b] | MCF-7 IC$_{50}$ μM[b] |
|---|---|---|---|---|---|---|
| E-31 | 4-Cl-C6H4-[1,2,4-thiadiazol-3-yl]-NH-C6H4-4-OH | 50-80 | 50-80 | 0.1-1 | ND | ND |
| E-32 | 4-Cl-C6H4-[1,3,4-thiadiazol-2-yl]-NH-C6H4-4-OH | 50-80 | 50-80 | 0.1-1 | ND | ND |
| (SKI-II) | 4-Cl-C6H4-[thiazol-2-yl]-NH-C6H4-4-OH | 50-80 | 80-100 | 0.1-1 | 1.0-10 | 10-100 |

[a]The % of activity compared to control (DMSO vehicle only). All compounds were run at 10 μM.
[b]Concentration of drug required to inhibit cell proliferation by 50%.
ND - not determined

Example 3

SphK1 proteasomal degradation studies

These studies were performed as previously described for the drug SKI-II (C. Loveridge et al. *J. Biol. Chem.* 2010, 285, 38891). Expression of wild-type SK1 and variants in Flp-In T-Rex HEK293 cells were induced with low concentrations of doxycycline hyuclate (50-200 ng/ml) that resulted in ~10-fold increases in SK1 activity above basal levels. After 24 h cells were treated with 10 μm test compound, 10 μm MG132, or both. DMSO was used as the vehicle control. After a further 24 h, cells were harvested, lysed, and subjected to SDS-PAGE and immunoblotting with anti-FLAG (Sigma), anti-ERK1/2 (Promega), or anti-a-tubulin (Abcam) antibodies. The results are depicted in Table 3. In all cases incorporation of MG132 blocked SphK1a degradation (0% degradation) by the test compound, indicating that degradation is proteasome dependent (C. Loveridge et al. *J. Biol. Chem.* 2010, 285, 38891).

TABLE 3

Level of degradation of SphK1a in Flpln-SphK1a cells

| Example (E-X) | % SphK1a degradation at 10 μM[b] |
|---|---|
| E-1 | 20 |
| E-9 | 60 |
| E-15 | 50 |
| E-19 | 80 |
| E-21 | 90 |
| E-22 | 100 |
| SKI-II | 100 |

[a]See Table 1.
[b]Level of degradation at 10 μM

Example 4

Inhibition of Collagen Synthesis in Neonatal Cardiac Fibroblasts (NCFs)

NCF collagen synthesis was determined by $^3$H-proline incorporation (Table 4).

Neonatal cardiac fibroblasts (NCFs) were isolated as previously reported (Lekawanvijit, S. Wang, B. H., Krum, H. Eur Heart J. 2010, 31(14), 1771-9). After isolation, NCF (passage 0) were placed into T75 cell culture flasks (BD Falcon, NSW, Australia) and maintained in high-glucose (25 mM) DMEM containing 5.33 mM KCl (Invitrogen, Mount Waverley, Vic, Australia) in the presence of 1% antibiotic/antimycotic (Invitrogen, Mount Waverley, Vic, Australia) and 10% fetal bovine serum (FBS) (JRH biosciences). Cells were incubated at 37° C. with 5% $CO_2$ for overnight and then the media were changed. NCF confluence was checked microscopically and NCF were sub-cultured. After removing media and 3× wash with warm 1×PBS, 2 ml of warm 0.05% trypsin-EDTA was added to each flask. Flasks were placed back into the 37° C. incubator for 1-2 minutes to allow cells to lift off the surface of the flasks. Trypsin was inactivated by adding 8 ml of DMEM containing 10% FBS. NCF (passage 1) were centrifuged for 6 minutes at 1300 rpm at RT. Cell pellets was washed 3× with DMEM+10% FBS and resuspended in DMEM+10% FBS. Cells were then placed into new flasks and incubated at 37° C. with 5% $CO_2$ for 48 hours.

To seed NCF, steps from trypsinization to resuspension were repeated as above. NCF (passage 2) were counted with the 'Countess' cell counter. NCF were seeded at a density of 50,000 cells/well in 12-well plates in DMEM+10% FBS and incubated at 37° C. with 5% $CO_2$ overnight. NCF were serum starved with media containing and 0.15 mM of vitamin C and 0.5% bovine serum albumin (BSA) for 48 hours.

A concurrent cell viability assay was performed to ascertain the degree to which reductions in $^3$H-proline can be attributed to inhibition of cell growth (see for example FIG. 1, below). Inhibition of NCF cell proliferation was measured using a 3-(4,5-dimethylthiazol-2-yl)-2,5-diphenyltetrazolium bromide (MTT) assay as previously described (Lekawanvijit, S. Wang, B. H., Krum, H. Eur Heart J. 2010, 31(14), 1771-9; Mosmann T. et al. J Immunol Methods 1983, 65, 55-63). In general, the extent of inhibition of proline incorporation cannot be accounted for on the basis of reduced cell growth, indicating that other mechanisms are operating (see sample data FIG. 1).

TABLE 4

Inhbition of NCF collagen synthesis

| Example (E-X)[a] | EC (μM)[b] |
|---|---|
| E-1 | 0.5-5 |
| E-2 | 5-10 |
| E-4 | 5-10 |
| E-9 | 0.5-5 |
| E-14 | 0.5-5 |
| E-25 | 5-10 |
| E-26 | 0.5-5 |
| E-27 | >10 |
| E-28 | 0.5-5 |
| E-30 | >10 |
| E-31 | 0.5-5 |
| E-32 | 0.5-5 |
| SKI-II | 0.5-5 |
| Fenretinide | 0.5-5 |

[a]See Table 2 for structures.
[b]EC = effective concentration, which is defined as the concentration required to reduce collagen synthesis to a level equal to or below unstimulated control.

The invention claimed is:

1. A compound of Formula (I);

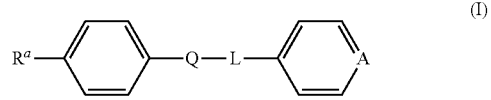

wherein

Q is a 5-membered heteroaromatic ring having 2 or 3 ring heteroatoms, at least one of which must be N and the remaining selected from N, O and S, selected from the group consisting of;

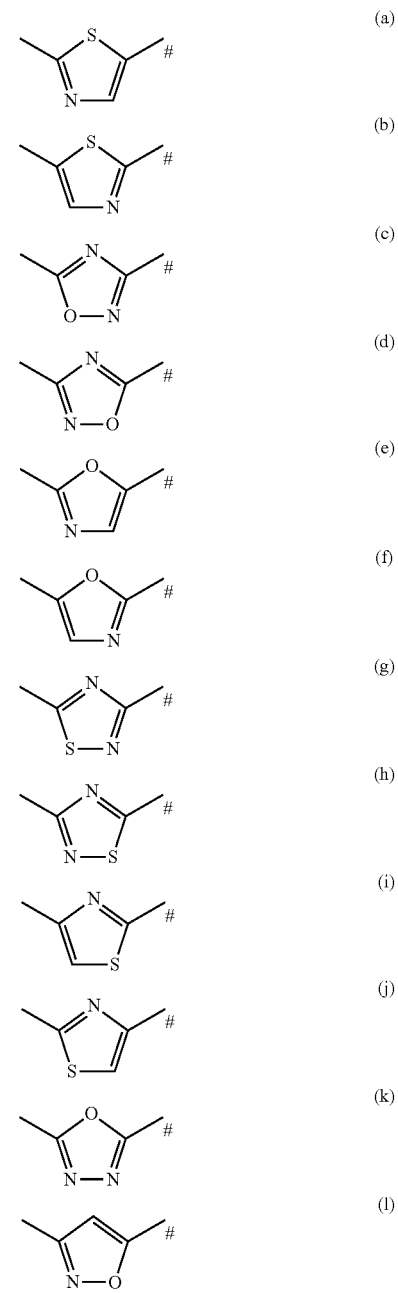

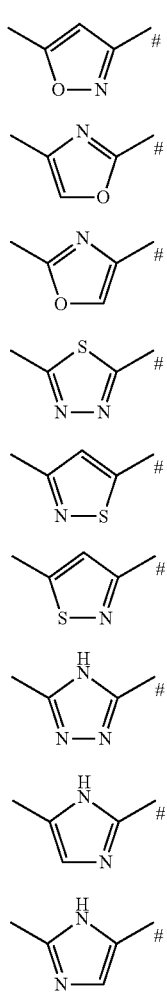

L is a bivalent linker group selected from —NH—, and —*NH—CH$_2$—, wherein the linker atom labelled * is bonded to Q;

R$^a$ is selected from hydrogen, halo, haloalkyl, haloalkoxy, alkyl, alkoxy, alkoxyalkyl, alkoxyalkoxy, carbocyclyl, carbocyclylalkyl, carbocyclyloxy, heterocyclyl, heterocyclylalkyl, heterocyclyloxy, aryl, arylalkyl, heteroaryl, heteroarylalkyl, aryloxy or heteroaryloxy, and wherein each of carbocyclyl, carbocyclylalkyl, carbocyclyloxy, heterocyclyl, heterocyclylalkyl, heterocyclyloxy, aryl, arylalkyl, heteroaryl, heteroarylalkyl, aryloxy or heteroaryloxy may be optionally substituted;

A is C—R$^b$, wherein R$^b$ is C(=NR$^c$)NHR$^d$;

wherein R$^c$ and R$^d$ are independently selected from hydrogen, hydroxy, alkyl, aryl, heteroaryl, carbocyclyl, heterocyclyl or acyl, each of which may be optionally substituted; or a pharmaceutically acceptable salt or solvate thereof.

2. The compound according to claim 1 wherein Q contains 2 ring heteroatoms.

3. The compound according to claim 1 wherein Q contains 3 ring heteroatoms.

4. The compound according to claim 3 wherein Q has at least 2 nitrogen ring atoms.

5. The compound according to claim 4 wherein Q is an oxadiazolyl group.

6. The compound according to claim 5 wherein Q is 1,3,4-oxadiazolyl.

7. The compound according to claim 1 wherein L is —NH—.

8. The compound according to claim 1 wherein R$^a$ is selected from hydrogen, halo (chloro, fluoro, bromo, iodo), C$_{1-6}$alkyl, haloC$_{1-6}$alkyl, C$_{1-6}$alkoxy, haloC$_{1-6}$alkoxy, C$_{1-6}$alkoxy C$_{1-6}$alkyl, C$_{1-6}$alkoxy C$_{1-6}$alkoxy, C$_{3-6}$cycloalkyl, C$_{3-6}$cycloalkylC$_{1-6}$alkyl, C$_{3-6}$cycloalkoxy, phenyl, phenylC$_{1-6}$alkyl, 5-6 membered heterocyclyl, and 5-6 membered heteroaryl.

9. A composition comprising a compound according to claim 1, or a pharmaceutically acceptable salt or solvate thereof, and a pharmaceutically acceptable additive.

10. A method of inhibiting undesirable cell proliferation in a subject in need thereof comprising administering to said subject, a compound according to claim 1, or a pharmaceutically acceptable salt or solvate thereof.

11. A method of treating a fibrotic disease in a subject in need thereof comprising administering to said subject, a compound according to claim 1, or a pharmaceutically acceptable salt or solvate thereof.

12. A method of treating a disease or condition in which excessive or undesirable sphingolipid enzyme activity is implicated in a subject in need thereof comprising administering to said subject, a compound according to claim 1, or a pharmaceutically acceptable salt or solvate thereof.

13. A method of inhibiting undesirable cell proliferation in a subject in need thereof comprising administering to said subject an amount of a compound according to claim 1, or a pharmaceutically acceptable salt or solvate thereof effective to inhibit undesirable cell proliferation.

14. A method of treating a fibrotic disease in a subject in need thereof comprising administering to said subject an amount of a compound according to claim 1, or a pharmaceutically acceptable salt or solvate thereof effective to treat said fibrotic disease.

15. The compound according to claim 1 wherein L is —*NH—CH$_2$—.

16. The compound of claim 1 wherein R$^b$ is selected from C(=NH)NH$_2$ and C(=NH—OH)NH$_2$.

17. The compound according to claim 1 selected from the group consisting of:

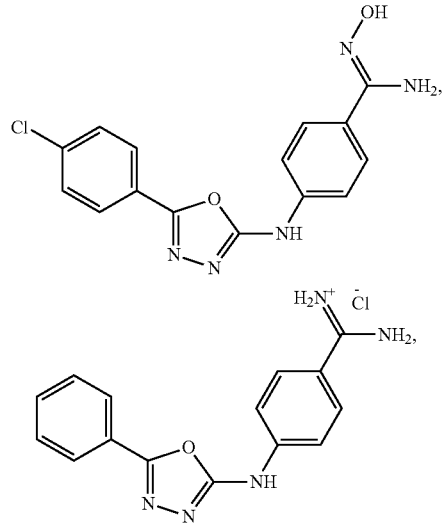

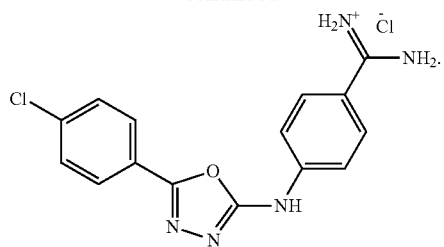
* * * * *